(12) United States Patent
Keil et al.

(10) Patent No.: US 7,655,679 B2
(45) Date of Patent: Feb. 2, 2010

(54) DERIVATIVES OF 2-AMINOTHIAZOLES AND 2-AMINO-OXAZOLES, PROCESSES FOR THEIR PREPARATION AND THEIR USE AS PHARMACEUTICAL COMPOSITIONS

(75) Inventors: Stefanie Keil, Frankfurt am Main (DE); Matthias Urmann, Frankfurt am Main (DE); Maike Glien, Frankfurt am Main (DE); Wolfgang Wendler, Frankfurt am Main (DE); Karen Chandross, Somerset, NJ (US); Lan Lee, Pluckemin Park, NJ (US)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/055,771

(22) Filed: Mar. 26, 2008

(65) Prior Publication Data
US 2008/0227834 A1 Sep. 18, 2008

Related U.S. Application Data

(63) Continuation of application No. PCT/EP2006/009302, filed on Sep. 26, 2006.

(30) Foreign Application Priority Data

Sep. 29, 2005 (EP) .................... 05021279

(51) Int. Cl.
*A61K 31/4025* (2006.01)
*C07D 413/10* (2006.01)

(52) U.S. Cl. ........................ 514/364; 548/129
(58) Field of Classification Search ............... 548/129
See application file for complete search history.

(56) References Cited

U.S. PATENT DOCUMENTS

| 5,641,796 | A | 6/1997 | Dominianni et al. |
| 6,653,334 | B1 | 11/2003 | Yamazaki et al. |

FOREIGN PATENT DOCUMENTS

| EP | 1586573 | 10/2005 |
| WO | WO 01/12612 | 2/2001 |
| WO | WO 03/074495 | 9/2003 |

OTHER PUBLICATIONS

Cecil Textbook of Medicine, 20$^{th}$ edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/indexhtml>.*
Anderluh, et al. European Journal of Medicinal Chemistry 40 (2005) 25-49.*

* cited by examiner

*Primary Examiner*—Rebecca L Anderson
*Assistant Examiner*—Shawquia Young
(74) *Attorney, Agent, or Firm*—Jiang Lin

(57) ABSTRACT

The present invention relates to derivatives of 2-aminothiazoles and 2-aminooxazoles in all its stereoisomeric forms, enantiomeric forms and mixtures in any ratio, and its physiologically acceptable salts and tautomeric forms showing peroxisome proliferators activator receptor (PPAR) delta agonist activity. These compounds are compounds of the formula I,

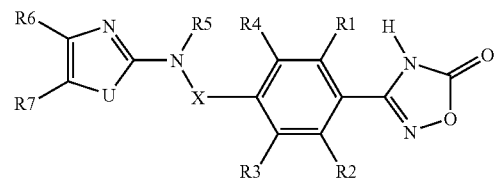

in which the radicals are as defined, and their physiologically acceptable salts and processes for their preparations. The compounds are suitable for the treatment and/or prevention of disorders of fatty acid metabolism and glucose utilization disorders as well as of disorders in which insulin resistance is involved and demyelinating and other neurodegenerative disorders of the central and peripheral nervous system.

10 Claims, No Drawings

DERIVATIVES OF 2-AMINOTHIAZOLES AND 2-AMINO-OXAZOLES, PROCESSES FOR THEIR PREPARATION AND THEIR USE AS PHARMACEUTICAL COMPOSITIONS

CROSS-REFERENCE TO RELATED APPLICATIONS

This application is a continuation of International Patent Application No. PCT/EP2006/009302 filed on Sep. 26, 2006 which is incorporated herein by reference in its entirety which also claims the benefit of priority of European Patent Application No. 05021279.4 filed on Sep. 15, 2005.

FIELD OF THE INVENTION

The present invention relates generally to pharmaceutical compositions for the treatment of metabolic disorders and the diseases and physiological problems resulting therefrom. More specifically, the present invention relates to compounds which are able to therapeutically modulate lipid and/or carbohydrate metabolism in mammals and are thus suitable for the prevention and/or treatment of diseases such as type-2 diabetes, atherosclerosis, cardiovascular disorders and the like. The inventive compounds of the present invention are also useful in the treatment of the demyelinating and other neurodegenerative disorders of the central and peripheral nervous systems.

BACKGROUND OF THE INVENTION

The present invention is directed to pharmaceutical compounds and compositions comprised of oxadiazolones and their physiologically acceptable salts and physiologically functional derivatives showing that are shown to provide peroxisome proliferator activator receptor (PPAR) delta agonist activity. PPARdelta agonists have been described in the prior art (e.g. WO 01/00603 and WO 02/092590 to Keil et. al., WO2003/074495, WO2004/093879, WO2004/080943, WO2005/054213 and WO2005/097786). Compounds comprising an oxadiazolone feature as inhibitors of factor Xa were disclosed in DE 101 12 768 A1, oral hypoglycemic agents in WO 96/13264. From WO 97/40017 compounds having a phenyl group linked to heterocycles are known as modulators of molecules with phosphotyrosine recognition units. Phenyl derivatives as agents for the therapy of thromboembolic disorders are known from WO 02/057236. Benzene derivatives as inhibitors of squalene synthase and protein farnesyltransferase are described in WO96/34851. See also U.S. Pat. No. 6,200,995 to De La Brouse-Elwood et. al. as well as WO 03/043997 and WO 02/092590 to Johnston et. al.).

The peroxisome proliferator-activated receptors (PPAR) are transducer proteins belonging to the steroid/thyroid/retinoid receptor superfamily. The PPAR receptors were originally identified as orphan receptors without known ligands, but were known for their ability to mediate the pleiotropic effects of fatty acid peroxisome proliferators. These receptors function as ligand-regulated transcription factors that control the expression of target genes by binding to their responsive DNA sequences as heterodimers with RXR. The target genes encode enzymes involved in a number of metabolic and cell growth/cell proliferation/cell differentiation inductions. These then provide targets for the development of therapeutic agents for the treatment of metabolic and central nervous system disorders, among others.

SUMMARY OF THE INVENTION

The present invention comprises derivatives of 2-aminothiazoles and 2-amino-oxazole compounds and the salts thereof as well as pharmaceutical compositions comprising them for the treatment of metabolic disorders and more particularly, those insulin-related metabolic disorders of the blood such as hyperlipidemia, diabetes, insulin-resistance and the like The compounds also effectively modulate lipid and/or carbohydrate metabolism and are thus suitable for the prevention and/or treatment of diseases such as type-2 diabetes, atherosclerosis and neurological disorders comprising demyelinating and other neurodegenerative disorders of the central and peripheral nervous systems.

Known as peroxisome proliferator-activated receptor (PPAR) agonists/antagonists, the invention relates to compounds of formula I

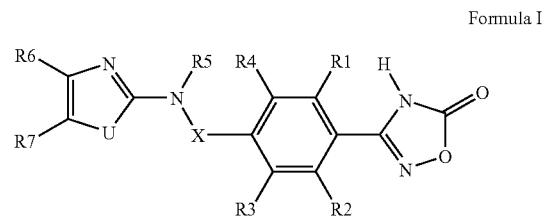

Formula I wherein the various substituent R-groups and other variables are more specifically defined herein.

DETAILED DESCRIPTION OF THE INVENTION

The present invention comprises compounds and compositions for the treatment of metabolic disorders and more particularly, those insulin-related metabolic disorders of the blood such as hyperlipidemia and diabetes and the like comprising arylcycloalkyl-substituted alkanoic acid derivatives and their salts. Known as peroxisome proliferator-activated receptors (PPAR) agonists/antagonists, the invention relates to compounds of formula I

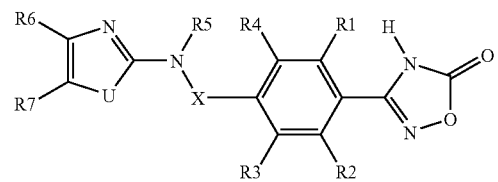

wherein the various R-group substituents are defined more specifically below

The invention was based on the object of providing compounds which permit therapeutically utilizable modulation of lipid and/or carbohydrate metabolism and are thus suitable for the prevention and/or treatment of diseases such as type 2 diabetes and atherosclerosis and the physiological manifestations and diseases thereof. Another purpose of the invention is to treat demyelinating and other neurodegenerative disorders of the central and peripheral nervous systems.

A series of compounds which effectively modulate the activity of PPARdelta and PPARalpha agonists are described herein, however, the relative activation of the receptor(s) may vary depending on the specific compounds.

The compounds of the present invention are structurally defined by formula I:

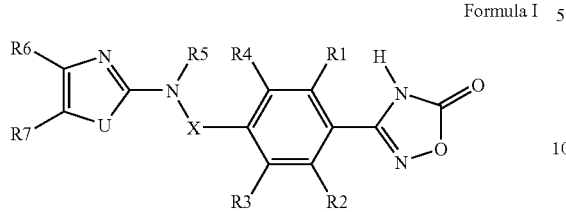

Formula I wherein
R1 is selected from the group consisting of H, halogen, (C1-C8) alkyl, (C1-C4) alkylene-O—(C1-C4) alkylene-H, SCH$_3$, and CN, wherein alkyl and alkylene are unsubstituted or mono, di- or tri-substituted by F;
R2, R3 and R4 are independently selected from the group consisting of H, halogen, (C1-C8) alkyl, (C1-C4) alkylene-O—(C1-C4) alkylene-H, SCH$_3$, CN, wherein alkyl and alkylene are unsubstituted or mono, di- or tri-substituted by F;
X is —CH2—, —CH2—CH2—;
U is S or O;
R5 is selected from the group consisting of H, (C1-C8) alkyl, (C1-C4)alkylene-O—(C1-C4)alkyl, (C1-C4)alkylene-O—(C1-C4)alkylene-(C6-C10) aryl, (C1-C4) alkylene-(C3-C12)cycloalkyl, (C2-C8)alkenyl, (C1-C4)alkylene-(C3-C15) heterocycloalkyl, (C1-C4)alkylene-(C3-C15) heterocycloalkenyl, (C1-C4) alkylene-(C5-C15)heteroaryl, wherein alkyl and alkylene are unsubstituted or mono-, di- or tri-substituted by F, N((C1-C4)alkylene-H)—(C1-C4) alkylene-H and O—(C1-C4)alkylene-H and wherein cycloalkyl, aryl, heterocycloalkyl, heterocycloalkenyl and heteroaryl are unsubstituted or mono-, di- or tri-substituted by F, Cl, Br, CF$_3$, (C1-C4)alkyl, CO—(C1-C4) alkyl and (C1-C4)-alkylen-O—(C1-C4)alkylene-H;
R6 and R7 are selected from the group consisting of H, (C6-C14)aryl, which is unsubstituted or mono-, di- or tri-substituted by F, Cl, Br, CF3, (C1-C4)alkyl and (C1-C4)-alkylen-O—(C1-C4)alkylene-H;
or
R6 and R7 together with the oxazole or thiazole ring form a benzothiazole or benzoxazole ring, which is optionally un-substituted or mono- di- or tri-substituted by F, Cl, Br, CF$_3$, (C1-C4)alkyl and (C1-C4)-alkylene-O—(C1-C4) alkylene-H;
in all its stereoisomeric and enantiomeric forms, mixtures thereof and its physiologically acceptable salts and tautomeric forms.

Another third possible embodiment of the present invention are compounds of formula I where one or more substituents have the following meaning:
R1 is selected from the group consisting of halogen, (C1-C8) alkyl, (C1-C4)alkylene-O—(C1-C4)alkylene-H, SCH3, CN, wherein the alkyl and alkylene groups are optionally unsubstituted or mono-, di- or tri-substituted by F;
R1 is selected from the group consisting of H, F, Cl, (C1-C4) alkyl, O—(C1-C4)alkyl, wherein alkyl and alkylene are unsubstituted or mono, bi- or tri-substituted by F;
R2, R3 and R4 are H;
X is —CH2—CH2—;
X is CH2;

U is S;
R5 is selected from the group consisting of (C1-C4)alkyl, (C1-C4)alkylene-O—(C1-C4)alkyl, (C1-C4)alkylene-O—CH2-phenyl, (C1-C4)alkylene-(C5-C6) heterocycloalkyl wherein alkyl and alkylene can be mono-, di- or tri-substituted by N((C1-C4)alkyl)-(C1-C4)alkyl and wherein heterocycloalkyl is unsubstituted or mono-substituted by (C1-C4)alkyl or CO—(C1-C4)alkyl;
R6 is phenyl mono-substituted by Cl or methoxy;
R6 and R7 together with the thiazole ring denote benzothiazole substituted by CF3 or Cl.

Another embodiment according to the invention are compounds of the formula I, wherein
R1 is H, F, CH3 or CF$_3$.

Another embodiment according to the invention are compounds of the formula I, wherein
R1 is F, CH3 or CF$_3$.

Another embodiment according to the invention are compounds of the formula I, wherein
R6 and R7, together with the thiazole ring to which they are attached form 6-trifluoromethyl-benzothiazole.

Yet, another more specific embodiment of the present invention are the compounds:
3-{4-[2-(Benzooxazol-2-yl-butyl-amino)-ethyl]-phenyl}-4H-[1,2,4]oxadiazol-5-one
3-{4-[2-(Benzothiazol-2-yl-butyl-amino)-ethyl]-phenyl}-4H-[1,2,4]oxadiazol-5-one
3-(4-{2-[Butyl-(6-methoxy-benzothiazol-2-yl)-amino]-ethyl}-phenyl)-4H-[1,2,4]oxadiazol-5-one
3-(4-{2-[Butyl-(6-chloro-benzothiazol-2-yl)-amino]-ethyl}-phenyl)-4H-[1,2,4]oxadiazol-5-one
3-(4-{2-[Butyl-(6-chloro-benzothiazol-2-yl)-amino]-ethyl}-2-methyl-phenyl)-4H-[1,2,4]oxadiazol-5-one
3-(4-{2-[Butyl-(6-trifluoromethyl-benzothiazol-2-yl)-amino]-ethyl}-2-methyl-phenyl)-4H-[1,2,4]oxadiazol-5-one
3-(2-Methyl-4-{2-[[2-(tetrahydro-pyran-4-yl)-ethyl]-(6-trifluoromethyl-benzothiazol-2-yl)-amino]-ethyl}-phenyl)-4H-[1,2,4]oxadiazol-5-one
3-(2-Methyl-4-{2-[(tetrahydro-pyran-3-ylmethyl)-(6-trifluoromethyl-benzothiazol-2-yl)-amino]-ethyl}-phenyl)-4H-[1,2,4]oxadiazol-5-one
3-(2-Methyl-4-{2-[(tetrahydro-pyran-4-ylmethyl)-(6-trifluoromethyl-benzothiazol-2-yl)-amino]-ethyl}-phenyl)-4H-[1,2,4]oxadiazol-5-one
3-(4-{2-[[2-(1-Acetyl-piperidin-4-yl)-ethyl]-(6-trifluoromethyl-benzothiazol-2-yl)-amino]-ethyl}-2-methyl-phenyl)-4H-[1,2,4]oxadiazol-5-one
3-{4-[(Benzooxazol-2-yl-butyl-amino)-methyl]-phenyl}-4H-[1,2,4]oxadiazol-5-one
3-{4-[(Benzothiazol-2-yl-butyl-amino)-methyl]-phenyl}-4H-[1,2,4]oxadiazol-5-one
3-(4-{[Butyl-(6-chloro-benzothiazol-2-yl)-amino]-methyl}-phenyl)-4H-[1,2,4]oxadiazol-5-one
3-(4-{2-[(3-Methoxy-propyl)-(6-trifluoromethyl-benzothiazol-2-yl)-amino]-ethyl}-2-methyl-phenyl)-4H-[1,2,4]oxadiazol-5-one
3-(4-{2-[[2-(2-Methoxy-ethoxy)-ethyl]-(6-trifluoromethyl-benzothiazol-2-yl)-amino]-ethyl}-2-methyl-phenyl)-4H-[1,2,4]oxadiazol-5-one
3-(4-{2-[(2-Benzyloxy-ethyl)-(6-trifluoromethyl-benzothiazol-2-yl)-amino]-ethyl}-2-methyl-phenyl)-4H-[1,2,4]oxadiazol-5-one
3-(4-{2-[(2-Methoxy-ethyl)-(6-trifluoromethyl-benzothiazol-2-yl)-amino]-ethyl}-2-methyl-phenyl)-4H-[1,2,4]oxadiazol-5-one 3-[4-(2-{Butyl-[4-(4-methoxy-phenyl)-thiazol-2-yl]-amino}-ethyl)-phenyl]-4H-[1,2,4]oxadiazol-5-one
3-[4-(2-{Butyl-[4-(4-chloro-phenyl)-thiazol-2-yl]-amino}-ethyl)-phenyl]-4H-[1,2,4]oxadiazol-5-one
3-(4-{2-[[4-(4-Chloro-phenyl)-thiazol-2-yl]-(3-methoxy-propyl)-amino]-ethyl}-phenyl)-4H-[1,2,4]oxadiazol-5-one
3-[4-(2-{[4-(4-Chloro-phenyl)-thiazol-2-yl]-[2-(2-methoxy-ethoxy)-ethyl]-amino}-ethyl)-phenyl]-4H-[1,2,4]oxadiazol-5-one
3-[4-(2-{(2-Benzyloxy-ethyl)-[4-(4-chloro-phenyl)-thiazol-2-yl]-amino}-ethyl)-phenyl]-4H-[1,2,4]oxadiazol-5-one
3-(4-{2-[[4-(4-Chloro-phenyl)-thiazol-2-yl]-(2-methoxy-ethyl)-amino]-ethyl}-phenyl)-4H-[1,2,4]oxadiazol-5-one
3-(4-{[Butyl-(6-trifluoromethyl-benzothiazol-2-yl)-amino]-methyl}-2-fluoro-phenyl)-4H-[1,2,4]oxadiazol-5-one
3-(4-{[Butyl-(6-chloro-benzothiazol-2-yl)-amino]-methyl}-2-fluoro-phenyl)-4H-[1,2,4]oxadiazol-5-one
3-(2-Fluoro-4-{[(2-pyrrolidin-1-yl-ethyl)-(6-trifluoromethyl-benzothiazol-2-yl)-amino]-methyl}-phenyl)-4H-[1,2,4]oxadiazol-5-one trifluoroacetate
3-(4-{[(2-Dimethylamino-ethyl)-(6-trifluoromethyl-benzothiazol-2-yl)-amino]-methyl}-2-fluoro-phenyl)-4H-[1,2,4]oxadiazol-5-one trifluoroacetate
3-(2-Fluoro-4-{[(2-methoxy-ethyl)-(6-trifluoromethyl-benzothiazol-2-yl)-amino]-methyl}-phenyl)-4H-[1,2,4]oxadiazol-5-one
3-(2-Fluoro-4-{[(2-piperidin-1-yl-ethyl)-(6-trifluoromethyl-benzothiazol-2-yl)-amino]-methyl}-phenyl)-4H-[1,2,4]oxadiazol-5-one trifluoroacetate
3-(2-Fluoro-4-{[(2-morpholin-4-yl-ethyl)-(6-trifluoromethyl-benzothiazol-2-yl)-amino]-methyl}-phenyl)-4H-[1,2,4]oxadiazol-5-one trifluoroacetate
3-(2-Fluoro-4-{[[2-(1-methyl-pyrrolidin-2-yl)-ethyl]-(6-trifluoromethyl-benzothiazol-2-yl)-amino]-methyl}-phenyl)-4H-[1,2,4]oxadiazol-5-one trifluoroacetate
3-(4-{[(2-Pyrrolidin-1-yl-ethyl)-(6-trifluoromethyl-benzothiazol-2-yl)-amino]-methyl}-2-trifluoromethyl-phenyl)-4H-[1,2,4]oxadiazol-5-one
3-(4-{[(2-Dimethylamino-ethyl)-(6-trifluoromethyl-benzothiazol-2-yl)-amino]-methyl}-2-trifluoromethyl-phenyl)-4H-[1,2,4]oxadiazol-5-one trifluoroacetate
3-(4-{[(2-Methoxy-ethyl)-(6-trifluoromethyl-benzothiazol-2-yl)-amino]-methyl}-2-trifluoromethyl-phenyl)-4H-[1,2,4]oxadiazol-5-one
3-(4-{[(2-Piperidin-1-yl-ethyl)-(6-trifluoromethyl-benzothiazol-2-yl)-amino]-methyl}-2-trifluoromethyl-phenyl)-4H-[1,2,4]oxadiazol-5-one trifluoroacetate
3-(4-{[(2-Morpholin-4-yl-ethyl)-(6-trifluoromethyl-benzothiazol-2-yl)-amino]-methyl}-2-trifluoromethyl-phenyl)-4H-[1,2,4]oxadiazol-5-one trifluoroacetate
3-(4-{[[2-(1-Methyl-pyrrolidin-2-yl)-ethyl]-(6-trifluoromethyl-benzothiazol-2-yl)-amino]-methyl}-2-trifluoromethyl-phenyl)-4H-[1,2,4]oxadiazol-5-one trifluoroacetate
3-[4-({Butyl-[4-(4-methoxy-phenyl)-thiazol-2-yl]-amino}-methyl)-phenyl]-4H-[1,2,4]oxadiazol-5-one
3-(4-{[[4-(4-Chloro-phenyl)-thiazol-2-yl]-(3-methoxy-propyl)-amino]-methyl}-2-fluoro-phenyl)-4H-[1,2,4]oxadiazol-5-one
3-(4-{[[4-(4-Chloro-phenyl)-thiazol-2-yl]-(2-methoxy-ethyl)-amino]-methyl}-2-fluoro-phenyl)-4H-[1,2,4]oxadiazol-5-one
3-[4-({[4-(4-Chloro-phenyl)-thiazol-2-yl]-[2-(2-methoxy-ethoxy)-ethyl]-amino}-methyl)-2-fluoro-phenyl]-4H-[1,2,4]oxadiazol-5-one This invention also encompasses all combinations and mixtures preferred aspects of the invention described herein.

As used herein, the term alkyl is to be understood in the broadest sense to mean saturated hydrocarbon residues which can be linear, i.e. straight-chain, or branched. If not otherwise defined alkyl has 1 to 8 carbon atoms. Examples of "—(C1-C8)-alkyl" are alkyl residues containing 1, 2, 3, 4, 5, 6, 7 or 8 carbon atoms are methyl, ethyl, propyl, butyl, pentyl, hexyl, heptyl or octyl, the n-isomers of all these residues, isopropyl, isobutyl, 1-methylbutyl, isopentyl, neopentyl, 2,2-dimethyl-butyl, 2-methylpentyl, 3-methylpentyl, isohexyl, sec-butyl, tert-butyl or tert-pentyl. The term "—(C0-C8)-alkyl" is a hydrocarbon residue containing 1, 2, 3, 4, 5, 6, 7 or 8 carbon atoms, in which the term "—C0-alkyl" is a covalent bond. All these statements apply also to the term alkylene.

As used herein, the term alkenyl is to be understood in the broadest sense to mean hydrocarbon residues which has 1 to 4 double bonds and can be linear, i.e. straight-chain, or branched. If not otherwise defined alkenyl has 2 to 8 carbon atoms. Examples of "—(C2-C8)-alkenyl" are alkenyl residues containing 2, 3, 4, 5, 6, 7 or 8 carbon atoms are, for example vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl. All these statements apply also to the term alkenylene.

As used herein, the term alkynyl is to be understood in the broadest sense to mean hydrocarbon residues, which has 1 to 4 triple bonds and can be linear, i.e. straight-chain, or branched. If not otherwise defined alkynyl has 2 to 8 carbon atoms. Examples of "—(C2-C8)-alkynyl" are alkynyl residues containing 2, 3, 4, 5, 6, 7 or 8 carbon atoms are, for example ethynyl, 1-propynyl, 2-propynyl (=propargyl) or 2-butynyl. All these statements apply also to the term alkylidene.

All these statements also apply if an alkyl group occurs as a substituent on another residue, for example in an alkyloxy residue, an alkyloxycarbonyl residue or an arylalkyl residue.

If not otherwise defined, alkyl, alkylene, alkenyl, alkenylene, alkynyl and alkynylene are unsubstituted or mono, di- or tri-substituted independently of one another by suitable groups such as, for example: F, Cl, Br, I, $CF_3$, $NO_2$, CN, COOH, CO—O—(C1-C4) alkylene-(C6-C10)aryl, CO—O—(C1-C4)alkyl, CO—O—(C1-C4)alkylene-(C3-C13)cycloalkyl, CO—O—(C1-C4)alkylene-(C3-C15)heterocycle, CO—N((C1-C4)alkylene-H)—(C1-C4)alkylene-(C6-C10) aryl, CO—N((C1-C4)alkylene-H)—(C1-C4) alkylene-H, CO—N((C1-C4)alkylene-H)—(C1-C4) alkylene-(C3-C13)cycloalkyl, CO—N((C1-C4) alkylene-H)—(C1-C4)alkylene-(C3-C15)heterocycle, (C1-C4) alkylene-(C3-C6)cycloalkyl, (C1-C4)alkylene-(C6-C10) aryl, (C1-C4)alkylene-(C3-C15)heterocycle, (C2-C6)-alkenyl, (C2-C6)-alkynyl, O—(C0-C6)-alkyl, O—(C1-C4) alkylene-(C6-C10) aryl, O—(C1-C4)alkylene-(C3-C12) cycloalkyl, O—(C1-C4)alkylene-(C3-C15)heterocycle, O—CO—O—(C1-C4)alkylene-(C6-C10)aryl, O—CO—O—(C1-C4)alkyl, O—CO—O—(C1-C4) alkylene-(C3-C13)cycloalkyl, O—CO—O—(C1-C4)alkylene-(C3-C15) heterocycle, S—(C1-C4)alkyl, S—(C1-C4)alkylene-(C3-C13)cycloalkyl, S—(C1-C4)alkylene-(C6-C10) aryl, S—(C1-C4)alkylene-(C3-C15) heterocycle, SO—(C1-C4) alkyl, SO—(C1-C4)alkylene-(C3-C13)cycloalkyl, SO—(C1-C4)alkylene-(C6-C10) aryl, SO—(C1-C4)alkylene-(C3-C15) heterocycle, $SO_2$-(C1-C4)alkyl, $SO_2$-(C1-C4)alkylene-(C3-C13)cycloalkyl, $SO_2$-(C1-C4)alkylene-(C6-C10) aryl, $SO_2$-(C1-C4)alkylene-(C3-C15)heterocycle, $SO_2$-N((C1-C4)alkylene-H)—(C1-C4)alkylene-(C6-C10) aryl, $SO_2$-N((C1-C4)alkylene-H)—(C1-C4)alkylene-H, $SO_2$-N((C1-C4)alkylene-H)—(C1-C4)alkylene-(C3-C13) cycloalkyl, $SO_2$-N((C1-C4)alkylene-H)—(C1-C4)alkylene- (C3-C15)heterocycle where the aryl ring or heterocyclic ring is unsubstituted or mono- or disubstituted by F, Cl, Br, OH, $_{CF3}$, NO2, CN, O$_{CF3}$, O—(C1-C6)-alkyl, (C1-C6)-alkyl, N((C1-C4)-alkylene-H)—(C1-C4)-alkylene-H; N((C1-C4)-alkylene-H)—(C1-C4)-alkylene-H, N((C1-C4)alkylene-H)—(C1-C4)alkylene-H)—(C1-C6)cycloalkyl, N((C1-C4)alkylene-H)—(C1-C4)alkylene-(C6-C12)-aryl, N((C1-C4)alkylene-H)—(C1-C4)alkylene-(C3-C15)heterocycle, N((C1-C4)alkylene-H)—CO—(C1-C4)alkylene-(C6-C12)-aryl, N((C1-C4)alkylene-H)—CO—(C1-C4)alkyl, N((C1-C4)alkylene-H)—CO—(C1-C4)alkylene-(C3-C13)cycloalkyl, N((C1-C4)alkylene-H)—CO—(C1-C4)alkylene-(C3-C15)heterocycle, N((C1-C4)alkylene-H)—CO—O—(C1-C4)alkylene-(C6-C12)-aryl, N((C1-C4)alkylene-H)—CO—O—(C1-C4)alkyl, N((C1-C4)alkylene-H)—CO—O—(C1-C4)alkylene-(C3-C13)cycloalkyl, N((C1-C4)alkylene-H)—CO—O—(C1-C4)alkylene-(C3-C15)heterocycle, N((C1-C4)alkylene-H)—CO—N((C1-C4)-alkylene-H)—(C1-C4)alkylene-(C6-C12)-aryl, N((C1-C4)alkylene-H)—CO—N((C1-C4)-alkylene-H)—(C1-C4)alkyl, N((C1-C4)alkylene-H)—CO—N((C1-C4)-alkylene-H)—(C1-C4)alkylene-(C3-C13)cycloalkyl, N((C1-C4)alkylene-H)—CO—N((C1-C4)-alkylene-H)—(C1-C4)alkylene-(C3-C15)heterocycle, where the aryl ring or heterocyclic ring is unsubstituted or mono- or disubstituted by F, Cl, Br, I, OH, CF3, NO2, CN, O$_{CF3}$, O—(C1-C6)-alkyl, (C1-C6)-alkyl, N((C1-C4)-alkylene-H)—(C1-C4)-alkylene-H, SO2-CH3, COOH, COO—(C1-C6)-alkyl, SF5, CONH2.

The term cycloalkyl is to be understood to mean saturated hydrocarbon cycle containing from 3 to 13 carbon atoms in a mono- or bicyclic, fused, bridged or spirocyclic ring. Examples of (C3-C13)-cycloalkyl cyclic alkyl residues are cycloalkyl residues containing 3, 4, 5, 6, 7, 8, 9, 10, 11, 12 or 13 ring carbon atoms like cyclopropyl, cyclobutyl, cyclopentyl, cyclohexyl, cycloheptyl, cyclooctyl, cyclononyl, cyclodecyl, cycloundecyl or cyclododecyl. The term cycloalkyl also includes bicyclic groups in which any of the above cycloalkyl ring is fused to a benzene ring, for example indane and 1,2,3,4-tetrahydronaphthalene.

The term cycloalkenyl is to be understood to mean unsaturated hydrocarbon cycle containing from 3 to 8 carbon atoms in a mono- or bicyclic, fused or bridged ring, wherein the one, two or three double bonds are not located within a cyclic alkyl group in such a manner that an aromatic system results. Examples of unsaturated cycloalkenyl groups are cyclopentenyl or cyclohexenyl, which can be bonded via any carbon atom. The term cycloalkenyl also includes bicyclic groups in which any of the above cycloalkenyl ring is fused to a benzene ring, for example 1,2-dihydronaphthalene, 1,4-dihydronaphthalene and 1H-indene.

If not otherwise defined cycloalkyl or cycloalkenyl are unsubstituted or mono, di- or tri-substituted independently of one another by suitable groups such as, for example: F, Cl, Br, I, CF3. NO2, CN, COOH, CO—O—(C1-C4)alkylene-(C6-C10)aryl, CO—O—(C1-C4) alkyl, CO—O—(C1-C4)alkylene-(C3-C13)cycloalkyl, CO—O—(C1-C4)alkylene-(C3-C15)heterocycle, CO—N((C1-C4)alkylene-H)—(C1-C6) alkylene-H, CO—N((C1-C4) alkylene-H)—(C1-C6) cycloalkyl, CON((C1-C4)alkylene-H)—(C1-C4)alkylene-(C6-C12)-aryl, (C1-C4)alkylene-(C3-C6)cycloalkyl, (C3-C6)alkyl, (C2-C6)-alkenyl, (C2-C6)-alkynyl, (C1-C4)alkylene-(C6-C10)aryl, (C1-C4)alkylene-(C3-C15)heterocycle, O—(C0-C6)-alkyl, (C1-C6)alkylene-O—(C1-C4)alkyl, (C1-C4)alkylene-O—(C1-C4)alkylene-(C3-C13)cycloalkyl, (C1-C4)alkylene-O—(C1-C4)alkylene-(C6-C10)aryl, (C1-C4) alkylene-O—(C1-C4)alkylene-(C3-C15)heterocycle, O—CO—O—(C1-C4)alkylene-(C6-C10) aryl, O—CO—O—(C1-C4)alkyl, O—CO—O—(C1-C4)alkylene-(C3-C13)cycloalkyl, O—CO—O—(C1-C4)alkylene-(C3-C15)heterocycle, O—CO—N((C1-C4)alkylene-H)—(C1-C4) alkylene-(C6-C10) aryl, O—CO—N((C1-C4) alkylene-H)—(C1-C4)alkylene-H, O—CO—N((C1-C4) alkylene-H)—(C1-C4)alkylene-(C3-C13)cycloalkyl, O—CO—N((C1-C4) alkylene-H)—(C1-C4)alkylene-(C3-C15) heterocycle, S—(C1-C4)alkyl, S—(C1-C4) alkylene-(C3-C13)cycloalkyl, S—(C1-C4)alkylene-(C6-C10) aryl, S—(C1-C4)alkylene-(C3-C15) heterocycle, SO—(C1-C4)alkyl, SO—(C1-C4)alkylene-(C3-C13)cycloalkyl, SO—(C1-C4)alkylene-(C6-C10) aryl, SO—(C1-C4)alkylene-(C3-C15)heterocycle, SO2-(C1-C4)alkyl, SO2-(C1-C4)alkylene-(C3-C13)cycloalkyl, SO2-(C1-C4)alkylene-(C6-C10) aryl, SO2-(C1-C4)alkylene-(C3-C15) heterocycle, SO2-N((C1-C4)alkylene-H)—(C1-C4)alkylene-(C6-C10) aryl, SO2-N((C1-C4)alkylene-H)—(C1-C4)alkylene-H, SO2-N((C1-C4)alkylene-H)—(C1-C4)alkylene-(C3-C13) cycloalkyl, SO2-N((C1-C4)alkylene-H)—(C1-C4)alkylene-(C3-C15)heterocycle, where the aryl ring or heterocyclic ring is unsubstituted or mono- or disubstituted by F, Cl, Br, OH, $_{CF3}$, NO2, CN, O$_{CF3}$, O—(C1-C6)-alkyl, (C1-C6)-alkyl, N((C1-C4)-alkylene-H)—(C1-C4)-alkylene-H; N((C1-C4)-alkylene-H)—(C1-C4)-alkylene-H, N((C1-C4)alkylene-H)—(C1-C4)alkylene-H)—(C1-C6)cycloalkyl, N((C1-C4)alkylene-H)—(C1-C4)alkylene-(C6-C12)-aryl, N((C1-C4)alkylene-H)—(C1-C4)alkylene-(C3-C15)heterocycle, N((C1-C4)alkylene-H)—CO—(C1-C4)alkylene-(C6-C12)-aryl, N((C1-C4)alkylene-H)—CO—(C1-C4)alkyl, N((C1-C4)alkylene-H)—CO—(C1-C4)alkylene-(C3-C13)cycloalkyl, N((C1-C4)alkylene-H)—CO—(C1-C4)alkylene-(C3-C15)heterocycle, N((C1-C4)alkylene-H)—CO—O—(C1-C4)alkylene-(C6-C12)-aryl, N((C1-C4)alkylene-H)—CO—O—(C1-C4)alkyl, N((C1-C4)alkylene-H)—CO—O—(C1-C4)alkylene-(C3-C13)cycloalkyl, N((C1-C4)alkylene-H)—CO—O—(C1-C4)alkylene-(C3-C15)heterocycle, N((C1-C4)alkylene-H)—CO—N((C1-C4)-alkylene-H)—(C1-C4)alkylene-(C6-C12)-aryl, N((C1-C4)alkylene-H)—CO—N((C1-C4)-alkylene-H)—(C1-C4)alkyl, N((C1-C4)alkylene-H)—CO—N((C1-C4)-alkylene-H)—(C1-C4)alkylene-(C3-C13)cycloalkyl, N((C1-C4)alkylene-H)—CO—N((C1-C4)-alkylene-H)—(C1-C4)alkylene-(C3-C15)heterocycle, where the aryl or heterocyclic ring is unsubstituted or mono- or disubstituted by F, Cl, Br, I, OH, CF3. NO2, CN, O$_{CF3}$, O—(C1-C6)-alkyl, (C1-C6)-alkyl, N((C1-C4)-alkylene-H)—(C1-C4)-alkylene-H,SO2-CH3, COOH, COO—(C1-C6)-alkyl, SF5, CONH2.

The term "aryl" is understood to mean aromatic hydrocarbon ring containing from 6 to 14 carbon atoms in a mono- or bicyclic ring. Examples of (C6-C14)-aryl rings are phenyl, naphthyl, for example 1-naphthyl and 2-naphthyl, biphenyl, for example 2-biphenyl, 3-biphenyl and 4-biphenyl, anthryl or fluorenyl. Biphenyl rings, naphthyl ring and, in particular, phenyl ring are further embodiments of aryl ring.

The terms heterocycle is understood to mean saturated (heterocycloalkyl), partly unsaturated (heterocycloalkenyl) or unsaturated (heteroaryl)hydrocarbon rings containing from 3 to 15 carbon atoms in a mono- or bicyclic, fused, bridged or spirocyclic ring in which 1 to 5 carbon atoms of the 3 to 15 ring carbon atoms are replaced by heteroatoms such as nitrogen, oxygen or sulfur in which further the heteroatoms can be oxidized, for example N=O, S=O, SO2. Examples of heterocycles are acridinyl, azaindole (1H-pyrrolopyridinyl), azabenzimidazolyl, azaspirodecanyl, azepinyl, azetidinyl, aziridinyl, benzimidazolyl, benzofuranyl, dihydrobenzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxalanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyi, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The heterocyclic rings are unsubstituted or mono-, di- or tri-substituted by suitable groups such as, for example: F, Cl, Br, I, $CF_3$, $NO_2$, CN, COOH, CO—O—(C1-C4) alkylene-(C6-C10)aryl, CO—O—(C1-C4)alkyl, CO—O—(C1-C4)alkylene-(C3-C13)cycloalkyl, CO—O—(C1-C4)alkylene-(C3-C15)heterocycle, CO—N((C1-C4) alkylene-H)—(C1-C6)alkylene-H, CO—N((C1-C4)alkylene-H)—(C1-C6)cycloalkyl, CON((C1-C4)alkylene-H)—(C1-C4)alkylene-(C6-C12)-aryl, (C1-C4)alkylene-(C3-C6)cycloalkyl, (C3-C6)alkyl, (C2-C6)-alkenyl, (C2-C6)-alkynyl, (C1-C4) alkylene-(C6-C10)aryl, (C1-C4)alkylene-(C3-C15) heterocycle, O—(C0-C6)-alkyl, (C1-C4)alkylene-O—(C1-C4)alkyl, (C1-C4)alkylene-O—(C1-C4)alkylene-(C3-C13) cycloalkyl, (C1-C4) alkylene-O—(C1-C4)alkylene-(C6-C10)aryl, (C1-C4)alkylene-O—(C1-C4)alkylene-(C3-C15) heterocycle, O—CO—O—(C1-C4)alkylene-(C6-C10) aryl, O—CO—O—(C1-C4)alkyl, O—CO—O—(C1-C4)alkylene-(C3-C13)cycloalkyl, O—CO—O—(C1-C4)alkylene-(C3-C15)heterocycle, O—CO—N((C1-C4)alkylene-H)—(C1-C4)alkylene-(C6-C10) aryl, O—CO—N((C1-C4)alkylene-H)—(C1-C4)alkylene-H, O—CO—N((C1-C4)alkylene-H)—(C1-C4) alkylene-(C3-C13)cycloalkyl, O—CO—N((C1-C4)alkylene-H)—(C1-C4)alkylene-(C3-C15) heterocycle, S—(C1-C4)alkyl, S—(C1-C4)alkylene-(C3-C13)cycloalkyl, S—(C1-C4) alkylene-(C6-C10) aryl, S—(C1-C4)alkylene-(C3-C15) heterocycle, SO—(C1-C4) alkyl, SO—(C1-C4)alkylene-(C3-C13)cycloalkyl, SO—(C1-C4)alkylene-(C6-C10) aryl, SO—(C1-C4)alkylene-(C3-C15) heterocycle, SO2-(C1-C4)alkyl, SO2-(C1-C4)alkylene-(C3-C13)cycloalkyl, SO2-(C1-C4)alkylene-(C6-C10) aryl, SO2-(C1-C4)alkylene-(C3-C15) heterocycle, SO2-N((C1-C4)alkylene-H)—(C1-C4)alkylene-(C6-C10) aryl, SO2-N((C1-C4)alkylene-H)—(C1-C4)alkylene-H, SO2-N((C1-C4)alkylene-H)—(C1-C4)alkylene-(C3-C13) cycloalkyl, SO2-N((C1-C4)alkylene-H)—(C1-C4)alkylene-(C3-C15)heterocycle, where the aryl ring or heterocyclic ring is unsubstituted or mono- or disubstituted by F, Cl, Br, OH, $CF_3$, $NO_2$, CN, $OCF_3$, O—(C1-C6)-alkyl, (C1-C6)-alkyl, N((C1-C4)-alkylene-H)—(C1-C4)-alkylene-H; N((C1-C4)-alkylene-H)—(C1-C4)-alkylene-H, N((C1-C4)alkylene-H)—(C1-C4)alkylene-H)—(C1-C6)cycloalkyl, N((C1-C4) alkylene-H)—(C1-C4)alkylene-(C6-C12)-aryl, N((C1-C4) alkylene-H)—(C1-C4)alkylene-(C3-C15)heterocycle, N((C1-C4)alkylene-H)—CO—(C1-C4)alkylene-(C6-C12)-aryl, N((C1-C4)alkylene-H)—CO—(C1-C4)alkyl, N((C1-C4)alkylene-H)—CO—(C1-C4)alkylene-(C3-C13)cycloalkyl, N((C1-C4)alkylene-H)—CO—(C1-C4)alkylene-(C3-C15)heterocycle, N((C1-C4)alkylene-H)—CO—O—(C1-C4)alkylene-(C6-C12)-aryl, N((C1-C4)alkylene-H)—CO—O—(C1-C4)alkyl, N((C1-C4)alkylene-H)—CO—O—(C1-C4)alkylene-(C3-C13)cycloalkyl, N((C1-C4) alkylene-H)—CO—O—(C1-C4)alkylene-(C3-C15) heterocycle, N((C1-C4)alkylene-H)—CO—N((C1-C4)-alkylene-H)—(C1-C4)alkylene-(C6-C12)-aryl, N((C1-C4) alkylene-H)—CO—N((C1-C4)-alkylene-H)—(C1-C4) alkyl, N((C1-C4)alkylene-H)—CO—N((C1-C4)-alkylene-H)—(C1-C4)alkylene-(C3-C13)cycloalkyl, N((C1-C4) alkylene-H)—CO—N((C1-C4)-alkylene-H)—(C1-C4) alkylene-(C3-C15)heterocycle, where the aryl or heterocyclic ring is unsubstituted or mono- or disubstituted by F, Cl, Br, I, OH, $CF_3$, $NO_2$, CN, $OCF_3$, O—(C1-C6)-alkyl, (C1-C6)-alkyl, N((C1-C4)-alkylene-H)—(C1-C4)-alkylene-H, SO2-CH3, COOH, COO—(C1-C6)-alkyl, $SF_5$, $CONH_2$.

The term "oxo-residue" or "=O" refers to residues such as carbonyl (—CO—), nitroso (—N=O), sulfinyl (—SO— or sulfonyl (—$SO_2$—).

Halogen is fluorine, chlorine, bromine or iodine.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

The compounds of the formula I may exist in the form of their racemates, racemic mixtures, pure enantiomers, diastereomers and mixtures of diastereomers as well in their tautomeric forms. The present invention encompasses all these isomeric and tautomeric forms of the compounds of the formula I. These isomeric forms can be obtained by methods known in the art.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

This invention relates further to the use of compounds of the formula I and their pharmaceutical compositions as PPAR ligands. The PPAR ligands of the invention are suitable as modulators of PPAR activity.

Peroxisome proliferator-activated receptors (PPAR) are transcription factors which can be activated by ligands and belong to the class of nuclear hormone receptors. There are three PPAR isoforms, PPARalpha, PPARgamma and PPARdelta (identical to PPARbeta), which are encoded by different genes (Peroxisome proliferator-activated receptor (PPAR): structure, mechanisms of activation and diverse functions: Motojima K., Cell Struct Funct., 1993, 18(5), 267-77).

In humans, PPARgamma exists in three variants, PPARgamma$_1$, gamma$_2$, and gamma$_3$, which are the result of alternative use of promoters and differential mRNA splicing. Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, the PPARalpha receptor plays an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effects and pathophysiology, see: Berger, J. et al., Annu. Rev. Med., 2002, 53, 409-435; Wilson, T. et al., J. Med. Chem., 2000, 43 (4), 527-550; Kliewer, S. et al., Recent Prog Horm Res., 2001, 56, 239-63; Moller, D. E. and Berger, J. P., Int J Obes Relat Metab Disord., 2003, 27 Suppl 3, 17-21; Ram, V. J., Drugs Today, 2003, 39(8), 609-32).

Among the three PPAR-isoforms the physiological functions of PPARdelta have long remained an enigma. The first proposed pharmacological role for PPARdelta has been the regulation of cholesterol homeostasis. It was shown that the somewhat selective PPARdelta ligand L-165041 raises plasma cholesterol in a diabetic animal model (Berger J. et al., J. Biol. Chem., 1999, 274, 6718-6725; Leibowitz M. D. et al., FEBS Lett., 2000, 473(3), 333-336). In obese, insulin resistant rhesus monkeys, the potent and selective PPARdelta ligand GW501516 raises HDL-cholesterol, decreases plasma LDL-cholesterol, triglycerides and insulin levels (Oliver, W. et al., Proc. Natl. Acad. Sci., 2001, 98, 5306-5311). The dual PPARdelta/PPARalpha agonist YM-16638 significantly lowers plasma lipids in rhesus and cynomoigus monkeys (Goto, S. et al., Br. J. Pharm., 1996, 118, 174-178) and acts in a similar manner in two weeks clinical trials in healthy volunteers (Shimokawa, T. et al., Drug Dev. Res., 1996, 38, 86-92). More recent publications underline that PPARdelta is an important target for the treatment of dyslipidemia, insulin resistance, type 2 diabetes, atherosclerosis and syndrom X (Wang, Y.-X. et al., Cell, 2003, 113, 159-170; Luquet, S. et al., FASEB J., 2003, 17, 209-226; Tanaka, T. et al., PNAS, 2003, 100, 15924-15929; Holst, D. et al., BioChem. Biophys. Acta, 2003, 1633, 43-50; Dressel, U. et al., Mol. Endocrin., 2003, 17, 2477-2493; Lee, C. H. et al., Science, 2003, 302, 453-457).

Besides its actions as a regulator of the lipid-, glucose- and cholesterol-metabolism PPARdelta is known to play a role in embryonic development, implantation and bone formation (Lim, H. and Dey, S. K., Trends Endocrinol Metab., 2000, 11(4), 137-42; Ding, N. Z. et al., Mol Reprod Dev., 2003, 66(3), 218-24; Mano, H. et al., J Biol. Chem., 2000, 275(11), 8126-32).

Numerous publications demonstrate that PPARdelta is triggering proliferation and differentiation of keratinocytes which points to its role in skin disorders and wound healing (Di-Poi, N. et al., J Steroid Biochem Mol Biol., 2003, 85(2-5), 257-65; Tan, N. S. et al., Am J Clin Dermatol., 2003, 4(8), 523-30; Wahli, W., Swiss Med Wkly., 2002, 132(7-8), 83-91).

PPARdelta appears to be significantly expressed in the CNS; however much of its function there still remains undiscovered. Of singular interest however, is the discovery that PPARdelta was expressed in rodent oligodendrocytes, the major lipid producing cells of the CNS (J. Granneman, et al., J. Neurosci. Res., 1998, 51, 563-573). Moreover, it was also found that a PPARdelta selective agonist was found to significantly increase oligodendroglial myelin gene expression and myelin sheath diameter in mouse cultures (I. Saluja et al., Glia, 2001, 33, 194-204). Thus, PPARdelta activators may be of use for the treatment of demyelinating and dysmyelinating diseases. The use of peroxisome proliferator activated receptor delta agonists for the treatment of MS and other demyelinating diseases can be shown as described in WO2005/097098.

Demyelinating conditions are manifested in loss of myelin—the multiple dense layers of lipids and protein which cover many nerve fibers. These layers are provided by oligodendroglia in the central nervous system (CNS), and Schwann cells in the peripheral nervous system (PNS). In patients with demyelinating conditions, demyelination may be irreversible; it is usually accompanied or followed by axonal degeneration, and often by cellular degeneration. Demyelination can occur as a result of neuronal damage or damage to the myelin itself—whether due to aberrant immune responses, local injury, ischemia, metabolic disorders, toxic agents, or viral infections (Prineas and McDonald, Demyelinating Diseases. In Greenfield's Neuropathology, 6.sup.th ed. (Edward Arnold: New York, 1997) 813-811, Beers and Berkow, eds., The Merck Manual of Diagnosis and Therapy, 17.sup.th ed. (Whitehouse Station, N.J.: Merck Research Laboratories, 1999) 1299, 1437, 1473-76, 1483). Central demyelination (demyelination of the CNS) occurs in several conditions, often of uncertain etiology, that have come to be known as the primary demyelinating diseases. Of these, multiple sclerosis (MS) is the most prevalent. Other primary demyelinating diseases include adrenoleukodystrophy (ALD), adrenomyeloneuropathy, AIDS-vacuolar myelopathy, HTLV-associated myelopathy, Leber's hereditary optic atrophy, progressive multifocal leukoencephalopathy (PML), subacute sclerosing panencephalitis, Guillian-Barre syndrome and tropical spastic paraparesis. In addition, there are acute conditions in which demyelination can occur in the CNS, e.g., acute disseminated encephalomyelitis (ADEM) and acute viral encephalitis. Furthermore, acute transverse myelitis, a syndrome in which an acute spinal cord transection of unknown cause affects both gray and white matter in one or more adjacent thoracic segments, can also result in demyelination. Also, disorders in which myelin forming glial cells are damaged including spinal cord injuries, neuropathies and nerve injury.

The present invention relates to compounds of the formula I suitable for modulating the activity of PPARs, especially the activity of PPARdelta and PPARalpha. Depending on the modulation profile, the compounds of the formula I are suitable for the treatment, control and prophylaxis of the indications described hereinafter, and for a number of other pharmaceutical applications connected thereto (see, for example, Berger, J., et al., Annu. Rev. Med., 2002, 53, 409-435; Wilson, T. et al., J. Med. Chem., 2000, 43(4), 527-550; Kliewer, S. et al., Recent Prog Horm Res., 2001, 56, 239-63; Fruchart, J. C. et al., 2001, Pharmacological Research, 44(5), 345-52; Kersten, S. et al., Nature, 2000, 405, 421-424; Torra, I. P. et al., Curr Opin Lipidol, 2001, 12, 245-254).

Compounds of this type are particularly suitable for the treatment and/or prevention of:
1. Disorders of fatty acid metabolism and glucose utilization disorders.
   Disorders in which insulin resistance is involved
2. Diabetes mellitus, especially type 2 diabetes, including the prevention of the sequelae associated therewith.
   Particular aspects in this connection are
      hyperglycemia,
      improvement in insulin resistance,
      improvement in glucose tolerance,
      protection of the pancreatic β cells
      prevention of macro- and microvascular disorders
3. Dyslipidemias and their sequelae such as, for example, atherosclerosis, coronary heart disease, cerebrovascular disorders etc, especially those (but not restricted thereto) which are characterized by one or more of the following factors:
   high plasma triglyceride concentrations, high postprandial plasma triglyceride concentrations,
   low HDL cholesterol concentrations
   low ApoA lipoprotein concentrations
   high LDL cholesterol concentrations
   small dense LDL cholesterol particles
   high ApoB lipoprotein concentrations
4. Various other conditions which may be associated with the metabolic syndrome, such as:
   obesity (excess weight), including central obesity
   thromboses, hypercoagulable and prothrombotic states (arterial and venous)
   high blood pressure
   heart failure such as, for example (but not restricted thereto), following myocardial infarction, hypertensive heart disease or cardiomyopathy
5. Disorders or conditions in which inflammatory reactions are involved:
   atherosclerosis such as, for example (but not restricted thereto), coronary sclerosis including angina pectoris or myocardial infarction, stroke
   vascular restenosis or reocclusion
   chronic inflammatory bowel diseases such as, for example, Crohn's disease and ulcerative colitis
   asthma
   lupus erythematosus (LE) or inflammatory rheumatic disorders such as, for example, rheumatoid arthritis
   other inflammatory states
6. Disorders of cell cycle or cell differentiation processes:
   adipose cell tumors
   lipomatous carcinomas such as, for example, liposarcomas
   solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
   acute and chronic myeloproliferative disorders and lymphomas
   angiogenesis
7. Demyelinating and other neurodegenerative disorders of the central and peripheral nervous systems including:
   Alzheimer's disease
   multiple sclerosis
   Parkinson's disease
   adrenoleukodystrophy (ALD)
   adrenomyeloneuropathy
   AIDS-vacuolar myelopathy
   HTLV-associated myelopathy
   Leber's hereditary optic atrophy
   progressive multifocal leukoencephalopathy (PML)
   subacute sclerosing panencephalitis
   Guillian-Barre syndrome
   tropical spastic paraparesis
   acute disseminated encephalomyelitis (ADEM)
   acute viral encephalitis
   acute transverse myelitis
   spinal cord and brain trauma
   Charcot-Marie-Tooth disease
8. Skin disorders and/or disorders of wound healing processes:
   erythemato-squamous dermatoses such as, for example, psoriasis
   acne vulgaris other skin disorders and dermatological conditions which are modulated by PPAR eczemas and neurodermitis dermatitis such as, for example, seborrheic dermatitis or photodermatitis keratitis and keratoses such as, for example, seborrheic keratoses, senile keratoses, actinic keratosis, photo-induced keratoses or keratosis follicularis keloids and keloid prophylaxis warts, including condylomata or condylomata acuminata human papilloma viral (HPV) infections such as, for example, venereal papillomata, viral warts such as, for example, molluscum contagiosum, leukoplakia papular dermatoses such as, for example, Lichen planus skin cancer such as, for example, basal-cell carcinomas, melanomas or cutaneous T-cell lymphomas localized benign epidermal tumors such as, for example, keratoderma, epidermal naevi chilblains wound healing 9. Other disorders high blood pressure pancreatitis syndrome X polycystic ovary syndrome (PCOS)

asthma osteoarthritis lupus erythematosus (LE) or inflammatory rheumatic disorders such as, for example, rheumatoid arthritis vasculitis wasting (cachexia)

gout ischemia/reperfusion syndrome acute respiratory distress syndrome (ARDS)

Formulations

The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on metabolic disorders. They beneficially influence lipid and sugar metabolism, in particular they lower the triglyceride level and are suitable for the prevention and treatment of type II diabetes and atheriosclerosis and the diverse sequalae thereof.

Combinations with Other Medicaments

The compounds of the invention can be administered alone or in combination with one or more further pharmacologically active substances. In particular, the compounds of the invention can be administered in combination with active ingredients having a similar pharmacological action. For example, they can be administered in combination with active ingredients which have favorable effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.
11. active ingredients for the treatment of neurodegenerative diseases
12. active ingredients for the treatment of disorders of the central nervous system
13. active ingredients for the treatment of drug, nicotine and alcohol addiction
14. analgesics They can be combined with the compounds of the invention of the formula I in particular for a synergistic enhancement of activity. Administration of the active ingredient combination can take place either by separate administration of the active ingredients to the patient or in the form of combination products in which a plurality of active ingredients are present in one pharmaceutical preparation.

Particularly suitable further active ingredients for the combination preparations are: All antidiabetics mentioned in the Rote Liste 2006, Chapter 12; all slimming agents/appetite suppressants mentioned in the Rote Liste 2006, Chapter 1; all lipid-lowering agents mentioned in the Rote Liste 2006, Chapter 58. They can be combined with the compound of the formula I according to the invention in particular for a synergistic enhancement of activity. The active compound combination can be administered either by separate administration of the active compounds to the patient or in the form of combination preparations in which a plurality of active compounds are present in a pharmaceutical preparation. Most of the active compounds listed below are disclosed in USP Dictionary of USAN and International Drug Names, US Pharmacopeia, Rockville 2001.

Antidiabetics include insulin and insulin derivatives, such as, for example, Lantus® (see www.lantus.com) or HMR 1964 or those described in WO2005005477 (Novo Nordisk), fast-acting insulins (see U.S. Pat. No. 6,221,633), inhalable insulins, such as, for example, Exubera® or oral insulins, such as, for example, IN-105 (Nobex) or Oral-lyn™ (Generex Biotechnology), GLP-1 derivatives, such as, for example, Exenatide, Liraglutide or those disclosed in WO 98/08871 or WO2005027978 by Novo Nordisk A/S, in WO 01/04156 by Zealand or in WO 00/34331 by Beaufour-Ipsen, pramlintide acetate (Symlin; Amylin Pharmaceuticals), and also orally effective hypoglycemic active ingredients.

The active compounds preferably include
sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase,
modulators of the glucose transporter 4 (GLUT4),
inhibitors of glutamine:fructose-6-phosphate amidotransferase (GFAT),
GLP-1 agonists,
potassium channel openers, such as, for example, those disclosed in WO 97/26265 and WO 99/03861 by Novo Nordisk A/S,
inhibitors of dipeptidylpeptidase IV (DPP-IV),
insulin sensitizers,
inhibitors of liver enzymes involved in the stimulation of gluconeogenesis and/or
glycogenolysis,
modulators of glucose uptake, glucose transport and glucose backresorption, inhibitors of 11β-HSD1,
inhibitors of protein tyrosine phosphatase 1B (PTP1B),
modulators of the sodium/glucose cotransporter 1 or 2 (SGLT1, SGLT2),
compounds which alter lipid metabolism, such as antihyperlipidemic active ingredients and antilipidemic active ingredients,
compounds which reduce food intake or food absorption,
compounds which increase thermogenesis,
PPAR and RXR modulators and
active ingredients which act on the ATP-dependent potassium channel of the beta cells.

In one embodiment of the invention, the compound of the formula I is administered in combination with a HMGCoA reductase inhibitor, such as simvastatin, fluvastatin, pravastatin, lovastatin, atorvastatin, cerivastatin, rosuvastatin or L-659699.

In one embodiment of the invention, the compound of the formula I is administered in combination with a cholesterol resorption inhibitor, such as, for example, ezetimibe, tiqueside, pamaqueside, FM-VP4 (sitostanol/campesterol ascorbyl phosphate; Forbes Medi-Tech, WO2005042692), MD-0727 (Microbia Inc., WO2005021497) or with compounds as described in WO2002066464 (Kotobuki Pharmaceutical Co. Ltd.), WO2005062824 (Merck & Co.) or WO2005061451 and WO2005061452 (AstraZeneca AB).

In one embodiment of the invention, the compound of the formula I is administered in combination with a PPAR gamma agonist, such as, for example, rosiglitazone, pioglitazone, JTT-501, GI 262570, R-483 or CS-011 (rivoglitazone).

In one embodiment of the invention, the compound of the formula I is administered in combination with a PPAR alpha agonist, such as, for example, GW9578, GW-590735, K-111, LY-674, KRP-101 or DRF-10945.

In one embodiment of the invention, the compound of the formula I is administered in combination with a mixed PPAR alpha/gamma agonist, such as, for example, muraglitazar, tesaglitazar, naveglitazar, LY-510929, ONO-5129, E-3030 or as described in WO00/64888, WO00/64876, WO03/020269, WO2004075891, WO2004076402, WO2004075815, WO2004076447, WO2004076428, WO2004076401, WO2004076426, WO2004076427, WO2006018118, WO2006018115, and WO2006018116 or in J. P. Berger et al., TRENDS in Pharmacological Sciences 28(5), 244-251, 2005.

In one embodiment of the invention, the compound of the formula I is administered in combination with a PPAR delta agonist, such as, for example, GW-501516 or as described in WO2005097762, WO2005097786, WO2005097763, and WO2006029699.

In one embodiment of the invention, the compound of the formula I is administered in combination with metaglidasen or with MBX-2044 or other partial PPAR gamma agonists/antagonists.

In one embodiment of the invention, the compound of the formula I is administered in combination with a fibrate, such as, for example, fenofibrate, clofibrate or bezafibrate.

In one embodiment of the invention, the compound of the formula I is administered in combination with an MTP inhibitor, such as, for example, implitapide, BMS-201038, R-103757 or those described in WO2005085226.

In one embodiment of the invention, the compound of the formula I is administered in combination with a CETP inhibitor, such as, for example, torcetrapib or JTT-705.

In one embodiment of the invention, the compound of the formula I is administered in combination with a bile acid resorption inhibitor (see, for example, U.S. Pat. Nos. 6,245,744, 6,221,897 or WO00/61568), such as, for example, HMR 1741 or those described in DE 10 2005 033099.1 and DE 10 2005 033100.9.

In one embodiment of the invention, the compound of the formula I is administered in combination with a polymeric bile acid adsorber, such as, for example, cholestyramine or colesevelam.

In one embodiment of the invention, the compound of the formula I is administered in combination with an LDL receptor inducer (see U.S. Pat. No. 6,342,512), such as, for example, HMR1171, HMR1586 or those described in WO2005097738.

In one embodiment, the compound of the formula I is administered in combination with Omacor® (omega-3 fatty acids; highly concentrated ethyl esters of eicosapentaenoic acid and docosahexaenoic acid).

In one embodiment of the invention, the compound of the formula I is administered in combination with an ACAT inhibitor, such as, for example, avasimibe.

In one embodiment of the invention, the compound of the formula I is administered in combination with an antioxidant, such as, for example, OPC-14117, probucol, tocopherol, ascorbic acid, β-carotene or selenium.

In one embodiment of the invention, the compound of the formula I is administered in combination with a vitamin, such as, for example, vitamin B6 or vitamin B12.

In one embodiment of the invention, the compound of the formula I is administered in combination with a lipoprotein lipase modulator, such as, for example, ibrolipim (NO-1886).

In one embodiment of the invention, the compound of the formula I is administered in combination with an ATP-citrate lyase inhibitor, such as, for example, SB-204990.

In one embodiment of the invention, the compound of the formula I is administered in combination with a squalene synthetase inhibitor, such as, for example, BMS-188494 or as described in WO2005077907.

In one embodiment of the invention, the compound of the formula I is administered in combination with a lipoprotein (a) antagonist, such as, for example, gemcabene (CI-1027).

In one embodiment of the invention, the compound of the formula I is administered in combination with an HM74A receptor agonists, such as, for example, nicotinic acid.

In one embodiment of the invention, the compound of the formula I is administered in combination with a lipase inhibitor, such as, for example, orlistat or cetilistat (ATL-962).

In one embodiment of the invention, the compound of the formula I is administered in combination with insulin.

In one embodiment of the invention, the compound of the formula I is administered in combination with a sulfonylurea, such as, for example, tolbutamide, glibenclamide, glipizide or glimepiride.

In one embodiment of the invention, the compound of the formula I is administered in combination with a biguanide, such as, for example, metformin.

In another embodiment of the invention, the compound of the formula I is administered in combination with a meglitinide, such as, for example, repaglinide or nateglinide.

In one embodiment of the invention, the compound of the formula I is administered in combination with a thiazolidinedione, such as, for example, troglitazone, ciglitazone, pioglitazone, rosiglitazone or the compounds disclosed in WO 97/41097 by Dr. Reddy's Research Foundation, in particular 5-[[4-[(3,4-dihydro-3-methyl-4-oxo-2-quinazolinyl-methoxy]phenyl]methyl]-2,4-thiazolidinedione.

In one embodiment of the invention, the compound of the formula I is administered in combination with an α-glucosidase inhibitor, such as, for example, miglitol or acarbose.

In one embodiment of the invention, the compound of the formula I is administered in combination with an active ingredient which acts on the ATP-dependent potassium channel of the beta cells, such as, for example, tolbutamide, glibenclamide, glipizide, glimepiride or repaglinide.

In one embodiment of the invention, the compound of the formula I is administered in combination with more than one of the compounds mentioned above, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment of the invention, the compound of the formula I is administered in combination with an inhibitor of glycogen phosphorylase, such as, for example, PSN-357 or FR-258900 or those described in WO2003084922, WO2004007455, WO2005073229-31 or WO2005067932.

In one embodiment of the invention, the compound of the formula I is administered in combination with glucagon receptor antagonists, such as, for example, A-770077, NNC-25-2504 or such as in WO2004100875 or WO2005065680.

In one embodiment of the invention, the compound of the formula I is administered in combination with activators of glucokinase, such as, for example, RO-4389620, LY-2121260 (WO2004063179), PSN-105, PSN-110, GKA-50 or those described, for example, by Prosidion in WO2004072031, WO2004072066, WO 05103021 or WO 06016178, by Roche in WO 00058293, WO 00183465, WO 00183478, WO 00185706, WO 00185707, WO 01044216, GB 02385328, WO 02008209, WO 02014312, WO 0246173, WO 0248106, DE 10259786, WO 03095438, U.S. Pat. No. 04,067,939 or WO 04052869, by Novo Nordisk in EP 1532980, WO 03055482, WO 04002481, WO 05049019, WO 05066145 or WO 05123132, by Merck/Banyu in WO 03080585, WO03097824, WO 04081001, WO 05063738 or WO 05090332, by Eli Lilly in WO 04063194, or by Astra Zeneca in WO 01020327, WO 03000262, WO 03000267, WO 03015774, WO 04045614, WO 04046139, WO 05044801, WO 05054200, WO 05054233, WO 05056530, WO 05080359, WO 05080360 or WO 05121110.

In one embodiment of the invention, the compound of the formula I is administered in combination with an inhibitor of gluconeogenesis, such as, for example, FR-225654.

In one embodiment of the invention, the compound of the formula I is administered in combination with inhibitors of fructose-1,6-bisphosphatase (FBPase), such as, for example, CS-917.

In one embodiment of the invention, the compound of the formula I is administered in combination with modulators of the glucose transporter 4 (GLUT4), such as, for example, KST-48 (D.-O. Lee et al.: Arzneim.-Forsch. Drug Res. 54 (12), 835 (2004)).

In one embodiment of the invention, the compound of the formula I is administered in combination with inhibitors of glutamine:fructose-6-phosphate amidotransferase (GFAT), as described, for example, in WO2004101528.

In one embodiment of the invention, the compound of the formula I is administered in combination with inhibitors of dipeptidylpeptidase IV (DPP-IV), such as, for example, vildagliptin (LAF-237), sitagliptin (MK-0431), saxagliptin ((BMS-477118), GSK-823093, PSN-9301, SYR-322, SYR-619, TA-6666, TS-021, GRC-8200, GW-825964× or as described in WO2003074500, WO2003106456, WO200450658, WO2005058901, WO2005012312, WO2005/012308, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment of the invention, the compound of the formula I is administered in combination with inhibitors of 11-beta-hydroxysteroid dehydrogenase-1 (11β-HSD1), such as, for example, BVT-2733 or those described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004065351, WO2004089367, WO2004089380, WO2004089470-71, WO2004089896, WO2005016877 or WO2005097759.

In one embodiment of the invention, the compound of the formula I is administered in combination with inhibitors of protein tyrosine phosphatase 1B (PTP1B), as described, for example, in WO200119830-31, WO200117516, WO2004506446, WO2005012295, PCT/EP2005/005311, PCT/EP2005/005321, PCT/EP2005/007151, PCT/EP2005/ or DE 10 2004 060542.4.

In one embodiment of the invention, the compound of the formula I is administered in combination with modulators of the sodium/glucose cotransporter 1 or 2 (SGLT1, SGLT2), such as, for example, KGA-2727, T-1095 and SGL-0010 or as described, for example, in WO2004007517, WO200452903, WO200452902, WO2005121161, WO2005085237, JP2004359630 or by A. L. Handlon in Expert Opin. Ther. Patents (2005) 15(11), 1531-1540.

In one embodiment of the invention, the compound of the formula I is administered in combination with inhibitors of hormone-sensitive lipase (HSL), such as those described, for example, in WO01/1 7981, WO01/66531, WO2004035550, WO2005073199 or WO03/051842.

In one embodiment of the invention, the compound of the formula I is administered in combination with inhibitors of acetyl-CoA carboxylase (ACC) such as those described, for example, in WO199946262, WO200372197, WO2003072197 or WO2005044814.

In one embodiment of the invention, the compound of the formula I is administered in combination with an inhibitor of phosphoenolpyruvate carboxykinase (PEPCK), such as those described, for example, in WO2004074288.

In one embodiment of the invention, the compound of the formula I is administered in combination with an inhibitor of glycogen synthase kinase-3 beta (GSK-3 beta), such as those described, for example, in US2005222220, WO2004046117, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727 or WO2004046117.

In one embodiment of the invention, the compound of the formula I is administered in combination with an inhibitor of protein kinase C beta (PKC beta), such as, for example, ruboxistaurin.

In one embodiment of the invention, the compound of the formula I is administered in combination with an endothelin-A receptor antagonist, such as, for example, avosentan (SPP-301).

In one embodiment of the invention, the compound of the formula I is administered in combination with inhibitors of "I-kappaB kinase" (IKK inhibitors), such as those described, for example, in WO2001000610, WO2001030774, WO2004022553 or WO2005097129.

In one embodiment of the invention, the compound of the formula I is administered in combination with modulators of the glucocorticoid receptor as described, for example, in WO2005090336.

In a further embodiment of the invention, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists such as, for example, {4-[(4-aminoquinazolin-2-ylamino)methyl]-cyclohexylmethyl}naphthalene-1-sulfonamide hydrochloride (CGP 71683A);

peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those described in WO2005080424;

cannabinoid receptor 1 antagonists, such as, for example, rimonabant, SR147778 or those described, for example, in EP 0656354, WO 00/15609, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,
367, WO200132663, WO2003086288, WO2003087037,
WO2004048317, WO2004058145, WO2003084930,
WO2003084943, WO2004058744, WO2004013120,
WO2004029204, WO2004035566, WO2004058249,
WO2004058255, WO2004058727, WO2004069838,
US20040214837, US20040214855, US20040214856,
WO2004096209, WO2004096763, WO2004096794,
WO2005000809, WO2004099157, US20040266845,
WO2004110453, WO2004108728, WO2004000817,
WO2005000820, US20050009870, WO200500974,
WO2004111033-34, WO200411038-39,
WO2005016286, WO2005007111, WO2005007628,
US20050054679, WO2005027837, WO2005028456,
WO2005063761-62, WO2005061509 or
WO2005077897;

MC4 agonists (for example [2-(3a-benzyl-2-methyl-3-oxo-2,
3,3a,4,6,7-hexahydro-pyrazolo[4,3-c]pyridin-5-yl)-1-(4-
chlorophenyl)-2-oxoethyl]-1-amino-1,2,3,4-tetrahydro-
naphthalene-2-carboxamide; (WO 01/91752)) or
LB53280, LB53279, LB53278 or THIQ, MB243, RY764,
CHIR-785, PT-141 or those described in WO2005060985,
WO2005009950, WO2004087159, WO2004078717,
WO2004078716, WO2004024720, US20050124652,
WO2005051391, WO2004112793, WOUS20050222014,
US20050176728, US20050164914, US20050124636,
US20050130988, US20040167201, WO2004005324,
WO2004037797, WO2005042516, WO2005040109,
WO2005030797, US20040224901, WO200501921,
WO200509184, WO2005000339, EP1460069,
WO2005047253, WO2005047251, EP1538159,
WO2004072076, WO2004072077 or WO2006024390;

orexin receptor antagonists (for example 1-(2-methylbenzox-
azol-6-yl)-3-[1,5]naphthyridin-4-ylurea hydrochloride
(SB-334867-A) or those described, for example, in
WO200196302, WO200185693, WO2004085403 or
WO2005075458);

histamine H3 receptor agonists (for example 3-cyclohexyl-1-
(4,4-dimethyl-1,4,6,7-tetrahydroimidazo[4,5-c]pyridin-5-
yl)-propan-1-one oxalic acid salt (WO 00/63208) or those
described in WO200064884, WO2005082893);

CRF antagonists (for example [2-methyl-9-(2,4,6-trimeth-
ylphenyl)-9H-1,3,9-triazafluoren-4-yl]dipropylamine
(WO 00/66585));

CRF BP antagonists (for example urocortin);

urocortin agonists;

β3 agonists (such as, for example, 1-(4-chloro-3-methane-
sulfonylmethylphenyl)-2-[2-(2,3-dimethyl-1H-indol-6-
yloxy)ethylamino]ethanol hydrochloride (WO
01/83451));

MSH (melanocyte-stimulating hormone) agonists;

MCH (melanin-concentrating hormone) receptor antagonists
(such as, for example, NBI-845, A-761, A-665798, A-798,
ATC-0175, T-226296, T-71, GW-803430 or those com-
pounds described in WO2003/15769, WO2005085200,
WO2005019240, WO2004011438, WO2004012648,
WO2003015769, WO2004072025, WO2005070898,
WO2005070925, WO2006018280, WO2006018279,
WO2004039780, WO2003033476, WO2002006245,
WO2002002744, WO2003004027 or FR2868780);

CCK-A agonists (such as, for example, {2-[4-(4-chloro-2,5-
dimethoxyphenyl)-5-(2-cyclohexylethyl)-thiazol-2-ylcar-
bamoyl]-5,7-dimethylindol-1-yl}acetic acid trifluoroace-
tic acid salt (WO 99/15525), SR-146131 (WO 0244150) or
SSR-125180);

serotonin reuptake inhibitors (for example dexfenfluramine);

mixed serotonin- and noradrenergic compounds (for example
WO 00/71549);

5-HT receptor agonists, for example 1-(3-ethylbenzofuran-
7-yl)piperazine oxalic acid salt (WO 01/09111);

5-HT2C receptor agonists (such as, for example, APD-356,
BVT-933 or those described in WO200077010,
WO20077001-02, WO2005019180, WO2003064423,
WO200242304 or WO2005082859);

5-HT6 receptor antagonists, such as described, for example,
in WO2005058858;

bombesin receptor agonists (BRS-3 agonists);

galanin receptor antagonists;

growth hormone (for example human growth hormone or
AOD-9604);

growth hormone releasing compounds (tert-butyl 6-benzy-
loxy-1-(2-diisopropylamino-ethylcarbamoyl)-3,4-dihy-
dro-1H-isoquinoline-2-carboxylate (WO 01/85695));

growth hormone secretagog receptor antagonists (ghrelin
antagonists) such as, for example, A-778193 or those
described in WO2005030734;

TRH agonists (see, for example, EP 0 462 884);

uncoupling protein 2 or 3 modulators;

leptin agonists (see for example Lee, Daniel W.; Leinung,
Matthew C.; Rozhavskaya-Arena, Marina; Grasso, Patri-
cia. Leptin agonists as a potential approach to the treatment
of obesity. Drugs of the Future (2001), 26(9), 873-881);

DA agonists (bromocriptine or Doprexin);

lipase/amylase inhibitors (as described, for example, in WO
00/40569);

inhibitors of diacylglycerol O-acyltransferases (DGATs)
such as described, for example, in US2004/0224997,
WO2004094618, WO200058491, WO2005044250,
WO2005072740, JP2005206492 or WO2005013907;

inhibitors of fatty acid synthase (FAS) such as, for example,
C75 or those described in WO2004005277;

oxyntomodulin;

oleoyi-estrone or thyroid hormone receptor agonists, such as, for example,
KB-2115 or those described in WO20058279,
WO200172692, WO200194293, WO2003084915,
WO2004018421 or WO2005092316.

In one embodiment of the invention, the further active ingredient is leptin; see for example "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment of the invention, the further active ingredient is dexamphetamine or amphetamine.

In one embodiment of the invention, the further active ingredient is fenfluramine or dexfenfluramine.

In another embodiment of the invention, the further active ingredient is sibutramine.

In one embodiment of the invention, the further active ingredient is mazindol or phentermine.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compound of the formula I is administered in combination with PDE (phosphodiesterase) inhibitors, as described, for example, in WO2003/077949 or WO2005012485.

In one embodiment of the invention, the compound of the formula I is administered in combination with NAR-1 (nicotinic acid receptor) agonists as described, for example, in WO2004094429.

In one embodiment of the invention, the compound of the formula I is administered in combination with CB2 (cannabinoid receptor) agonists as described, for example, in US2005/143448.

In one embodiment of the invention, the compound of the formula I is administered in combination with histamine 1 agonists as described, for example, in WO2005101979.

In one embodiment of the invention, the compound of the formula I is administered in combination with bupropion, as described in WO2006017504.

In one embodiment of the invention, the compound of the formula I is administered in combination with opioid antagonists as described, for example, in WO2005107806 or WO2004094429.

In one embodiment of the invention, the compound of the formula I is administered in combination with neutral endopeptidase inhibitors as described, for example, in WO200202513, WO2002/06492, WO 2002040008, WO2002040022 or WO2002047670.

In one embodiment of the invention, the compound of the formula I is administered in combination with NPY inhibitors (neuropeptide Y) as described, for example, in WO2002047670.

In one embodiment of the invention, the compound of the formula I is administered in combination with sodium/hydrogen exchange inhibitors as described, for example, in WO2003092694.

In one embodiment of the invention, the compound of the formula I is administered in combination with modulators of the glucocorticoid receptor as described, for example, in WO2005090336.

In one embodiment of the invention, the compound of the formula I is administered in combination with nicotine receptor agonists as described, for example, in WO2004094429.

In one embodiment of the invention, the compound of the formula I is administered in combination with NRIs (norepinephrine reuptake inhibitors) as described, for example, in WO2002053140.

In one embodiment of the invention, the compound of the formula I is administered in combination with MOA (E-beta-methoxyacrylate), such as, for example, segeline, or as described, for example, in WO2002053140.

In one embodiment of the invention, the compound of the formula I is administered in combination with antithrombotic active ingredients, such as, for example, clopidogrel.

It is to be understood that each suitable combination of the compounds according to the invention with one or more of the compounds mentioned above and optionally one or more further pharmacologically active substances is meant to be included in the scope of the present invention.

The formulae for some of the development codes mentioned above are given below.

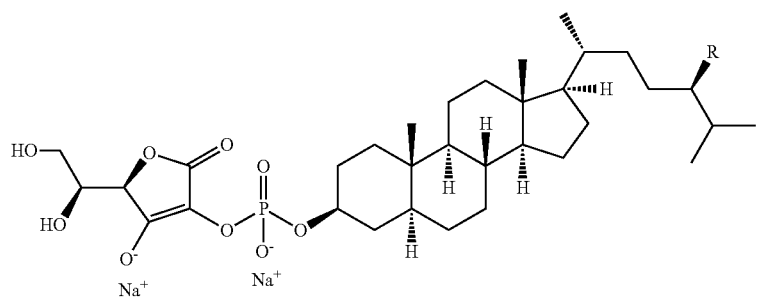

FM-VP4

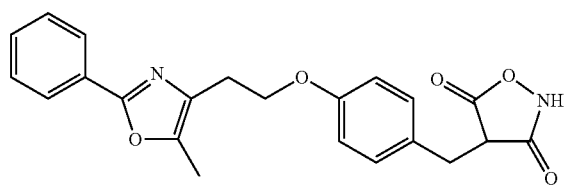

JTT-501

-continued
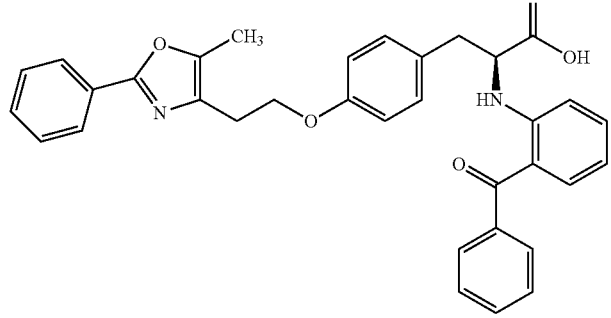
GI262570
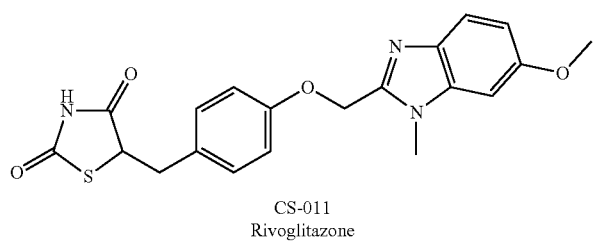
CS-011
Rivoglitazone
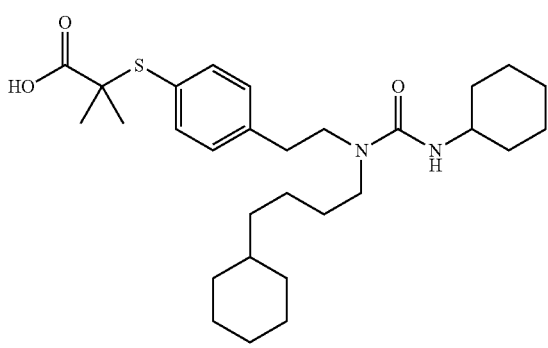
GW-9578
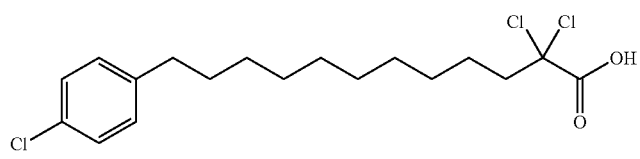
K-111
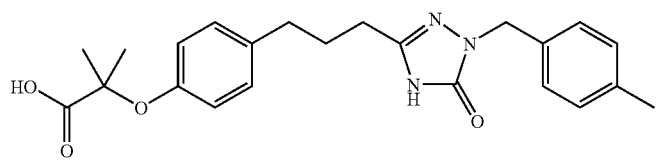
LY-674
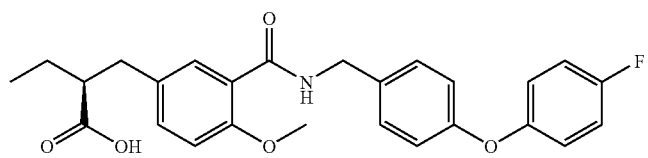
KRP-101
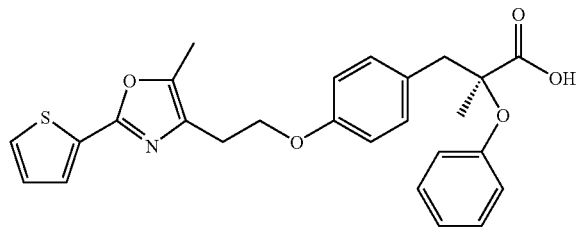
LY-510929

-continued
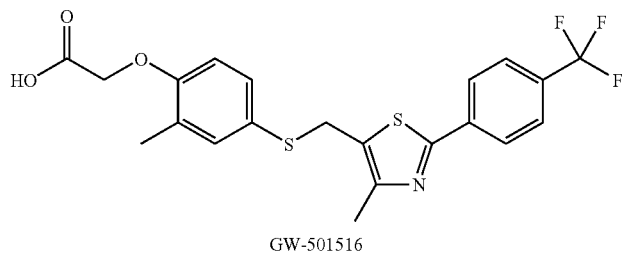
GW-501516
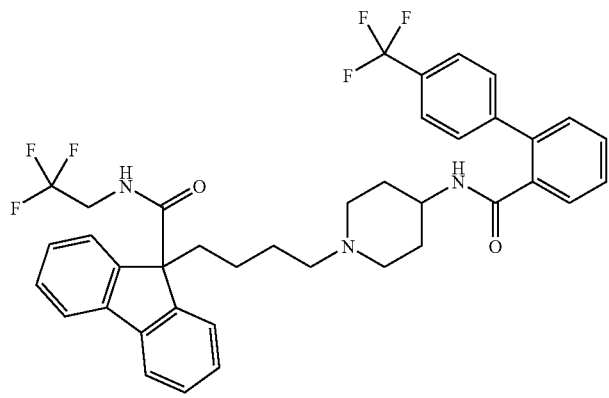
BMS-201038
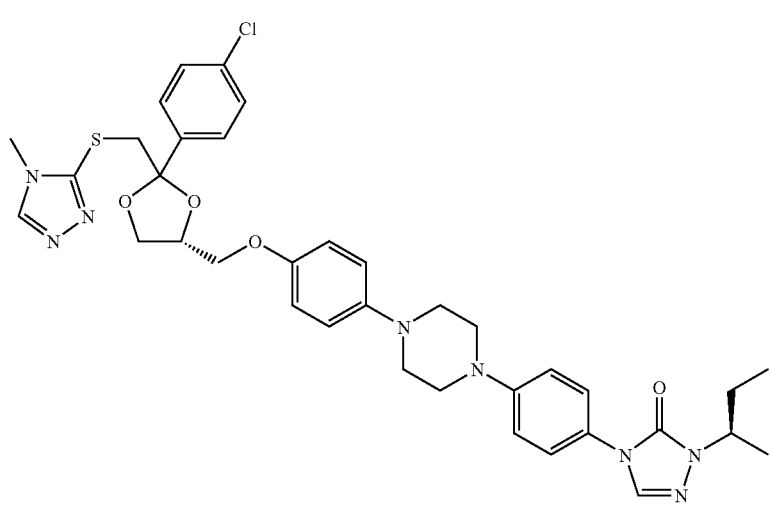
R-103757
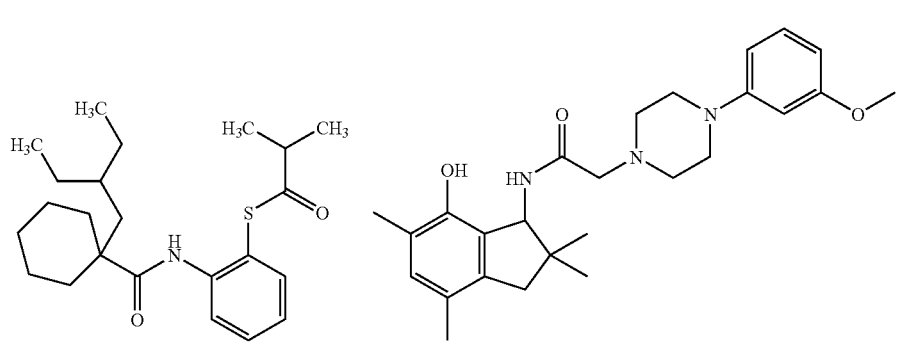
JTT-705   OPC-14117

-continued
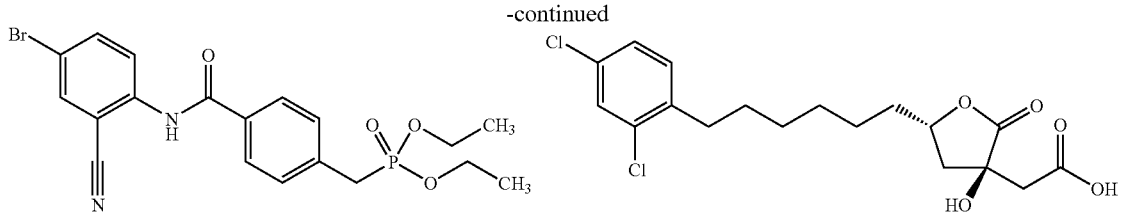
NO-1886
SB-204990
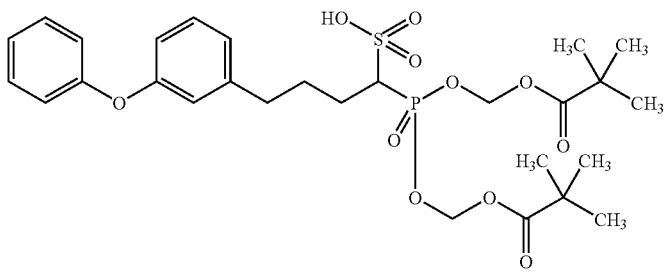
BMS-188494
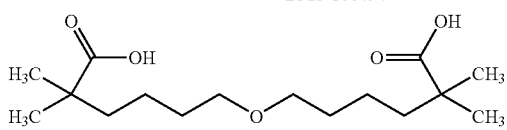
Cl-1027
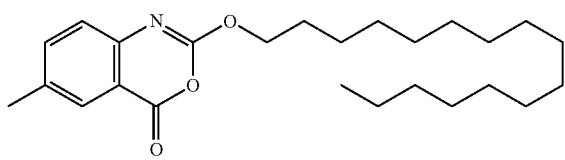
ATL-962
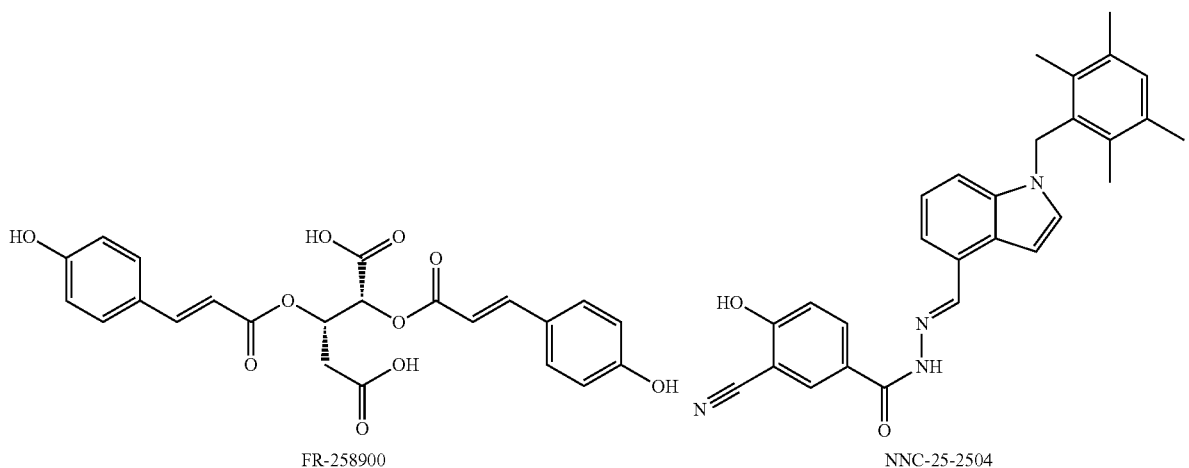
FR-258900
NNC-25-2504
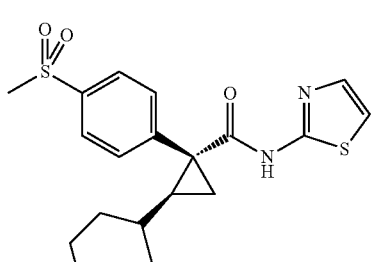
LY-2121260
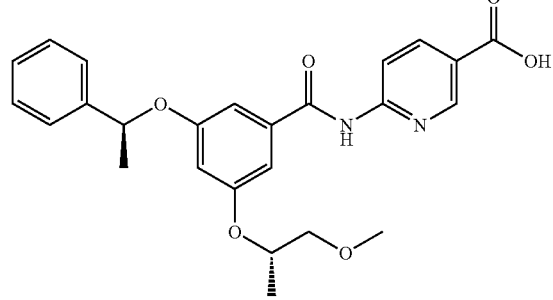
GKA-50

-continued
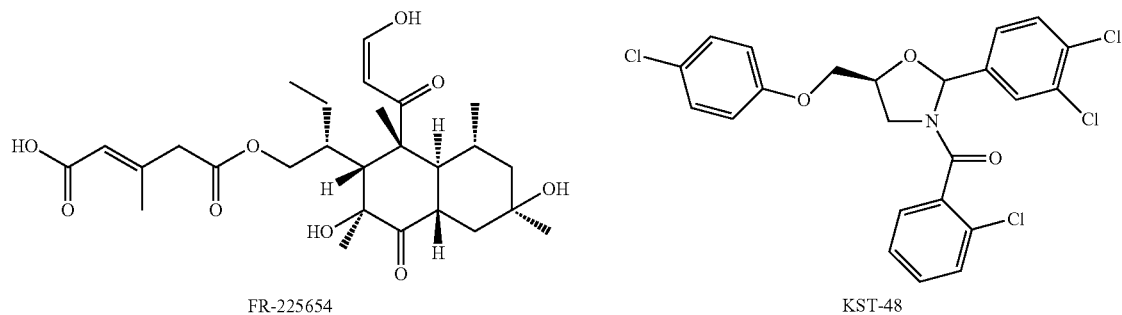
FR-225654
KST-48
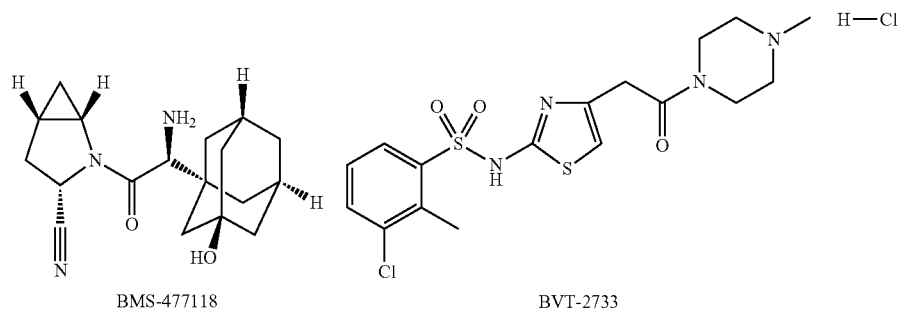
BMS-477118
BVT-2733
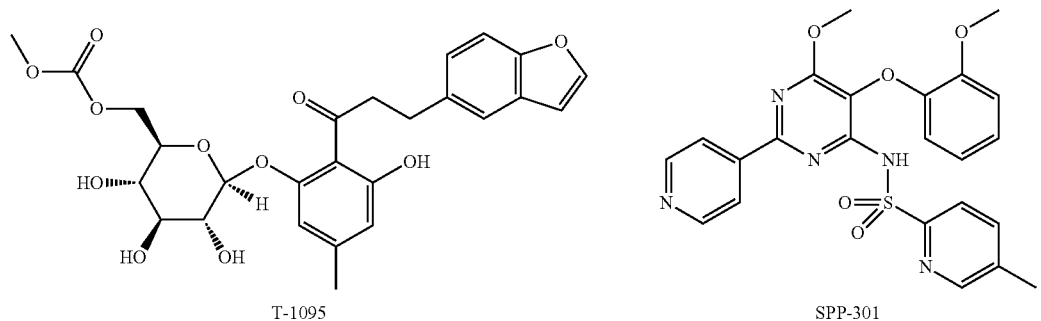
T-1095
SPP-301
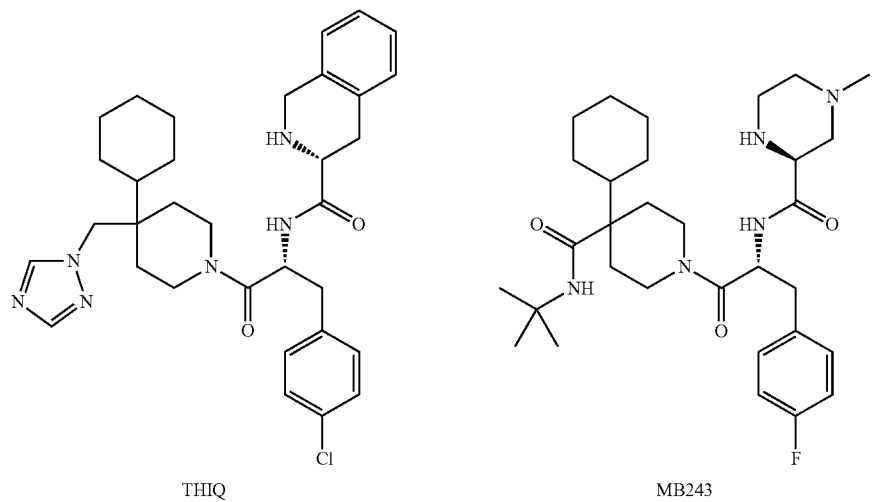
THIQ
MB243

-continued
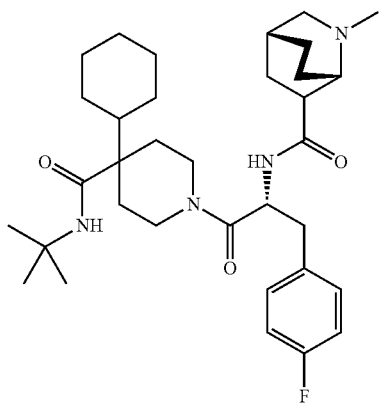
RY764
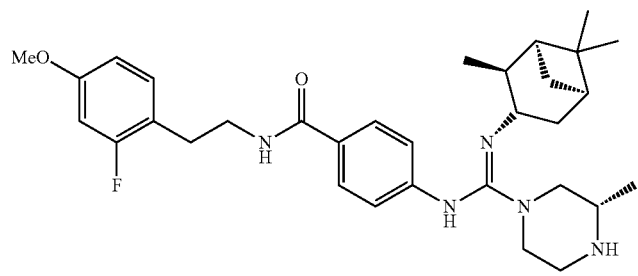
CHIR-785
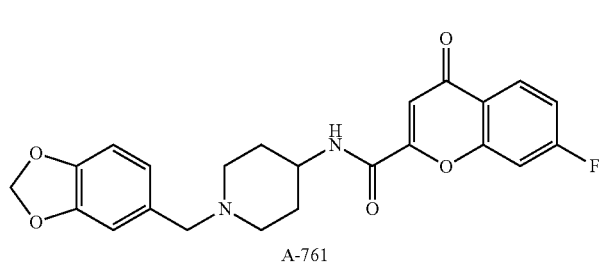
A-761
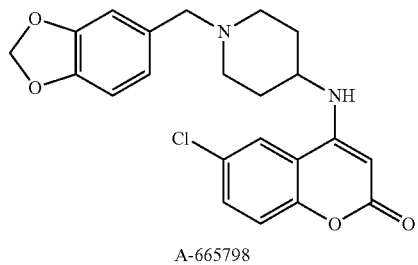
A-665798
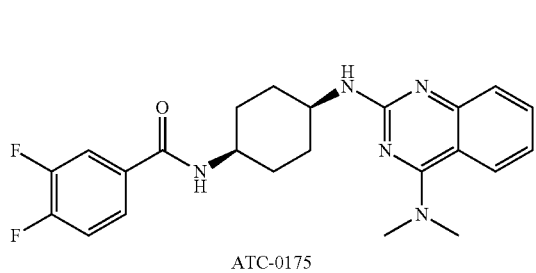
ATC-0175
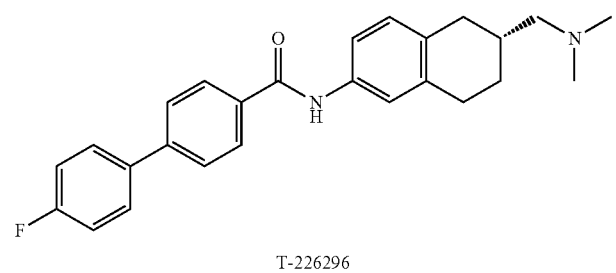
T-226296
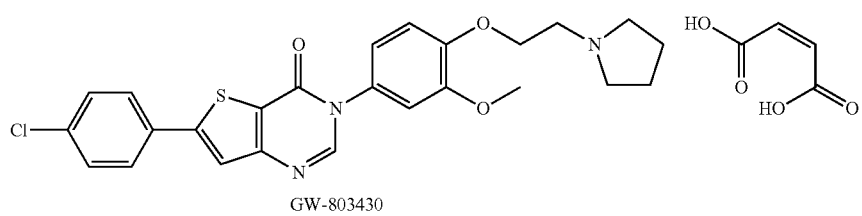
GW-803430

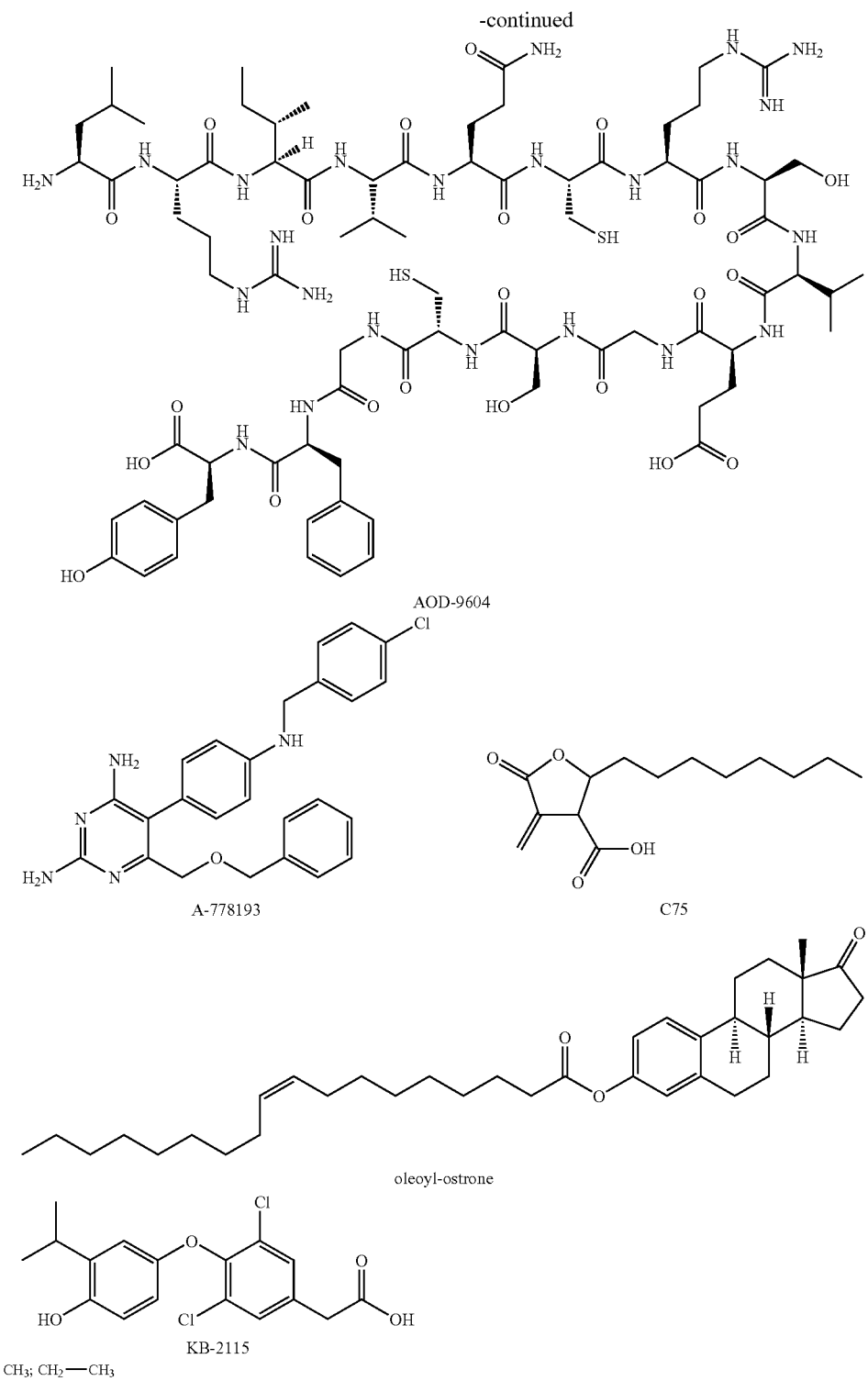

The activity of the compounds was tested as follows:

Determination of EC50 Values of PPAR Agonists in the Cellular PPARalpha Assay

Principle

The potency of substances which bind to human PPARalpha and activate it in an agonistic manner is analyzed using a stably transfected HEK cell line (HEK=human embryo kidney) which is referred to here as PPARalpha reporter cell line. It contains two genetic elements, a luciferase reporter element (pdeltaM-GAL4-Luc-Zeo) and a PPARalpha fusion protein (GR-GAL4-humanPPARalpha-LBD) which mediates expression of the luciferase reporter element depending on a PPARalpha ligand. The stably and constitutively expressed fusion protein GR-GAL4-humanPPARalpha-LBD binds in the cell nucleus of the PPARalpha reporter cell line via the GAL4 protein portion to the GAL4 DNA binding motifs 5'-upstream of the luciferase reporter element which is stably integrated in the genome of the cell line. There is only weak expression of the luciferase reporter gene in the absence of a PPARalpha ligand if fatty acid-depleted fetal calf serum (cs-FCS) is used in the assay. PPARalpha ligands bind and activate the PPARalpha fusion protein and thereby stimulate the expression of the luciferase reporter gene. The luciferase which is formed can be detected by means of chemiluminescence via an appropriate substrate.

Construction of the PPARalpha Reporter Cell Line

The PPARalpha reporter cell line was prepared in two stages. Firstly, the luciferase reporter element was constructed and stably transfected into HEK cells. For this purpose, five binding sites of the yeast transcription factor GAL4 (Accession # AF264724) were cloned in 5'-upstream of a 68 bp-long minimal MMTV promoter (Accession # V01175). The minimal MMTV promoter section contains a CCMT box and a TATA element in order to enable efficient transcription by RNA polymerase II. The cloning and sequencing of the GAL4-MMTV construct took place in analogy to the description of Sambrook J. et. al. (Molecular cloning, Cold Spring Harbor Laboratory Press, 1989). Then the complete Photinus pyralis gene (Accession # M15077) was cloned in 3'-downstream of the GAL4-MMTV element. After sequencing, the luciferase reporter element consisting of five GAL4 binding sites, MMTV promoter and luciferase gene was recloned into a plasmid which confers zeocin resistance in order to obtain the plasmid pdeltaM-GAL4-Luc-Zeo. This vector was transfected into HEK cells in accordance with the statements in Ausubel, F. M. et al. (Current protocols in molecular biology, Vol. 1-3, John Wiley & Sons, Inc., 1995). Then zeocin-containing medium (0.5 mg/ml) was used to select a suitable stable cell clone which showed very low basal expression of the luceriferase gene.

In a second step, the PPARalpha fusion protein (GR-GAL4-humanPPARalpha-LBD was introduced into the stable cell clone described. For this purpose, initially the cDNA coding for the N-terminal 76 amino acids of the glucocorticoid receptor (Accession # P04150) was linked to the cDNA section coding for amino acids 1-147 of the yeast transcription factor GAL4 (Accession # P04386). The cDNA of the ligand-binding domain of the human PPARalpha receptor (amino acids S167-Y468; Accession # S74349) was cloned in at the 3'-end of this GR-GAL4 construct. The fusion construct prepared in this way (GR-GAL4-humanPPARalpha-LBD) was recloned into the plasmid pcDNA3 (Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line which contains a luciferase reporter element and constitutively expresses the PPARalpha fusion protein (GR-GAL4-human PPARalpha-LBD) was isolated by selection with zeocin (0.5 mg/ml) and G418 (0.5 mg/ml).

Assay Procedure

The activity of PPARalpha agonists is determined in a 3-day assay which is described below:

Day 1

The PPARalpha reporter cell line is cultivated to 80% confluence in DMEM (# 41965-039, Invitrogen) which is mixed with the following additions: 10% cs-FCS (fetal calf serum; #SH-30068.03, Hyclone), 0.5 mg/ml zeocin (#R250-01, Invitrogen), 0.5 mg/ml G418 (#10131-027, Invitrogen), 1% penicillin-streptomycin solution (#15140-122, Invitrogen) and 2 mM L-glutamine (#25030-024, Invitrogen). The cultivation takes place in standard cell culture bottles (# 353112, Becton Dickinson) in a cell culture incubator at 37° C. in the presence of 5% $CO_2$. The 80%-confluent cells are washed once with 15 ml of PBS (#14190-094, Invitrogen), treated with 3 ml of trypsin solution (#25300-054, Invitrogen) at 37° C. for 2 min, taken up in 5 ml of the DMEM described and counted in a cell counter. After dilution to 500.000 cells/ml, 35,000 cells are seeded in each well of a 96 well microtiter plate with a clear plastic base (#3610, Corning Costar). The plates are incubated in the cell culture incubator at 37° C. and 5% $CO_2$ for 24 h.

Day 2

PPARalpha agonists to be tested are dissolved in DMSO in a concentration of 10 mM. This stock solution is diluted in DMEM (#41965-039, Invitrogen) which is mixed with 5% cs-FCS (#SH-30068.03, Hyclone), 2 mM L-glutamine (#25030-024, Invitrogen) and the previously described antibiotics (zeocin, G418, penicillin and streptomycin). Test substances are tested in 11 different concentrations in the range from 10 µM to 100 pM. More potent compounds are tested in concentration ranges from 1 µM to 10 pM or between 100 nM and 1 pM.

The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96 well microtiter plate. The DMSO concentration in the assay is less than 0.1% v/v in order to avoid cytotoxic effects of the solvent.

Each plate was charged with a standard PPARalpha agonist, which was likewise diluted in 11 different concentrations, in order to demonstrate the functioning of the assay in each individual plate. The assay plates are incubated in an incubator at 37° C. and 5% $CO_2$ for 24 h.

Day 3

The PPARalpha reporter cells treated with the test substances are removed from the incubator, and the medium is aspirated off. The cells are lyzed by pipetting 50 µl of Bright Glo reagent (from Promega) into each well of a 96 well microtiter plate. After incubation at room temperature in the dark for 10 minutes, the microtiter plates are measured in the luminometer (Trilux from Wallac). The measuring time for each well of a microtiter plate is 1 sec.

Evaluation

The raw data from the luminometer are transferred into a Microsoft Excel file. Dose-effect plots and EC50 values of PPAR agonists are calculated using the XL.Fit program as specified by the manufacturer (IDBS).

The PPARalpha EC50 values for the compounds of Examples 1 to 41 in this assay are in the range from 50 nM to >10 µM. Compounds of the invention of the formula I activate the PPARalpha receptor.

Determination of EC50 Values of PPAR Agonists in the Cellular PPARdelta Assay

Principle

The potency of substances which bind to human PPARdelta and activate it in an agonistic manner is analyzed using a stably transfected HEK cell line (HEK=human embryo kidney) which is referred to here as PPARdelta reporter cell line. In analogy to the assay described for PPARalpha, the PPARdelta reporter cell line also contains two genetic elements, a luciferase reporter element (pdeltaM-GAL4-Luc-Zeo) and a PPARdelta fusion protein (GR-GAL4-humanP-PARdelta-LBD) which mediates expression of the luciferase reporter element depending on a PPARdelta ligand. The stably and constitutively expressed fusion protein GR-GAL4-humanPPARdelta-LBD binds in the cell nucleus of the PPARdelta reporter cell line via the GAL4 protein portion to the GAL4 DNA binding motifs 5'-upstream of the luciferase reporter element which is stably integrated in the genome of the cell line. There is only little expression of the luciferase reporter gene in the absence of a PPARdelta ligand if fatty acid-depleted fetal calf serum (cs-FCS) is used in the assay. PPARdelta ligands bind and activate the PPARdelta fusion protein and thereby stimulate expression of the luciferase reporter gene. The luciferase which is formed can be detected by means of chemiluminescence via an appropriate substrate.

Construction of the PPARdelta Reporter Cell Line

The production of the stable PPARdelta reporter cell line is based on a stable HEK-cell clone which was stably transfected with a luciferase reporter element. This step was already described above in the section "construction of the PPARalpha reporter cell line". In a second step, the PPARdelta fusion protein (GR-GAL4-humanPPARdelta-LBD was stably introduced into this cell clone. For this purpose, the cDNA coding for the N-terminal 76 amino acids of the glucocorticoid receptor (Accession # P04150) was linked to the cDNA section coding for amino acids 1-147 of the yeast transcription factor GAL4 (Accession # P04386). The cDNA of the ligand-binding domain of the human PPARdelta receptor (amino acids S139-Y441; Accession # L07592) was cloned in at the 3'-end of this GR-GAL4 construct. The fusion construct prepared in this way (GR-GAL4-humanPPARdelta-LBD) was recloned into the plasmid pcDNA3 (Invitrogen) in order to enable constitutive expression by the cytomegalovirus promoter. This plasmid was linearized with a restriction endonuclease and stably transfected into the previously described cell clone containing the luciferase reporter element. The resulting PPARdelta reporter cell line which contains a luciferase reporter element and constitutively expresses the PPARdelta fusion protein (GR-GAL4-human PPARdelta-LBD) was isolated by selection with zeocin (0.5 mg/ml) and G418 (0.5 mg/ml).

Assay Procedure and Evaluation

The activity of PPARdelta agonists is determined in a 3-day assay in exact analogy to the procedure already described for the PPARalpha reporter cell line except that the PPARdelta reporter cell line and a specific PPARdelta agonist was used as a standard to control test efficacy.

PPARdelta EC50 values in the range from 1 nM to >10 μM were measured for the PPAR agonists of Examples 1 to 41 described in this application. Compounds of the invention of the formula I activate the PPARdelta receptor.

The examples given in Table II serve to illustrate the invention, but without limiting it.

TABLE I

| Example | X | U | R1 | R5 | R6 | R7 |
|---|---|---|---|---|---|---|
| 1 | —CH2CH2— | O | H | —(CH2)3CH3 |  | |
| 2 | —CH2CH2— | S | H | —(CH2)3CH3 |  | |
| 3 | —CH2CH2— | S | H | —(CH2)3CH3 | 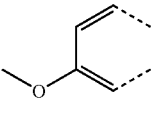 | |
| 4 | —CH2CH2— | S | H | —(CH2)3CH3 | 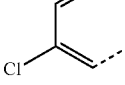 | |
| 5 | —CH2CH2— | S | —CH3 | —(CH2)3CH3 | 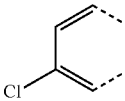 | |

TABLE I-continued
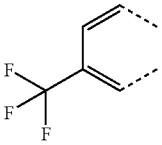
| Example | X | U | R1 | R5 | R6 | R7 |
|---|---|---|---|---|---|---|
| 6 | —CH2CH2— | S | —CH3 | —(CH2)3CH3 | 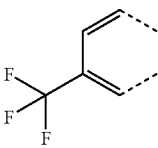 | |
| 7 | —CH2CH2— | S | —CH3 | 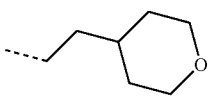 | 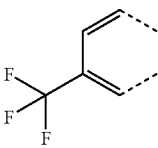 | |
| 8 | —CH2CH2— | S | —CH3 | 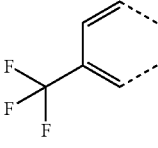 | 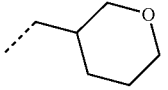 | |
| 9 | —CH2CH2— | S | —CH3 | 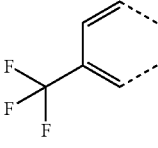 | 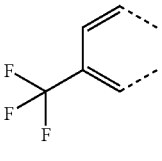 | |
| 10 | —CH2CH2— | S | —CH3 | 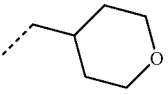 | 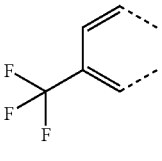 | |
| 11 | —CH2— | O | H | —(CH2)3CH3 | 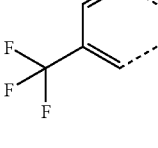 | |
| 12 | —CH2— | S | H | —(CH2)3CH3 | 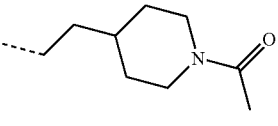 | |
| 13 | —CH2— | S | H | —(CH2)3CH3 | 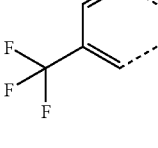 | |
| 14 | —CH2CH2— | S | —CH3 | —(CH2)3—O—CH3 | 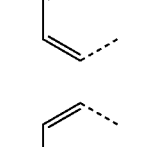 | |

TABLE I-continued

| Example | X | U | R1 | R5 | R6 | R7 |
|---|---|---|---|---|---|---|
| 15 | —CH2CH2— | S | —CH3 | —(CH2)2—O—(CH2)2—O—CH3 | 3-(trifluoromethyl)phenyl | |
| 16 | —CH2CH2— | S | —CH3 | —(CH2)2—O—CH2—C6H5 | 3-(trifluoromethyl)phenyl | |
| 17 | —CH2CH2— | S | —CH3 | —(CH2)2—O—CH3 | 3-(trifluoromethyl)phenyl | |
| 18 | —CH2CH2— | S | H | —(CH2)3CH3 | 4-methoxyphenyl | H |
| 19 | —CH2CH2— | S | H | —(CH2)3CH3 | 4-chlorophenyl | H |
| 20 | —CH2CH2— | S | H | —(CH2)3—O—CH3 | 4-chlorophenyl | H |
| 21 | —CH2CH2— | S | H | —(CH2)2—O—(CH2)2—O—CH3 | 4-chlorophenyl | H |
| 22 | —CH2CH2— | S | H | —(CH2)2—O—CH2—C6H5 | 4-chlorophenyl | H |
| 23 | —CH2CH2— | S | H | —(CH2)2—O—CH3 | 4-chlorophenyl | H |
| 24 | —CH2— | S | F | —(CH2)3CH3 | 3-(trifluoromethyl)phenyl | |
| 25 | —CH2— | S | F | —(CH2)3CH3 | 4-chlorophenyl | |

TABLE I-continued

| Example | X | U | R1 | R5 | R6 | R7 |
|---------|---|---|----|----|----|----|
| 26 | —CH2— | S | F | ⟨pyrrolidin-1-yl-ethyl⟩ | —CF3 | |
| 27 | —CH2— | S | F | ⟨-CH2CH2-N(CH3)2⟩ | —CF3 | |
| 28 | —CH2— | S | F | —(CH2)2—O—CH3 | —CF3 | |
| 29 | —CH2— | S | F | ⟨piperidin-1-yl-ethyl⟩ | —CF3 | |
| 30 | —CH2— | S | F | ⟨morpholin-4-yl-ethyl⟩ | —CF3 | |
| 31 | —CH2— | S | F | ⟨(1-methylpyrrolidin-2-yl)methyl⟩ | —CF3 | |
| 32 | —CH2— | S | —CF3 | ⟨pyrrolidin-1-yl-ethyl⟩ | —CF3 | |
| 33 | —CH2— | S | —CF3 | ⟨-CH2CH2-N(CH3)2⟩ | —CF3 | |

TABLE I-continued

[Structure: R6 and R7 on oxazole/thiazole ring (U) connected via CHR5-X to a benzene ring with R1, R2, R3, R4 substituents and a 1,2,4-oxadiazol-5(4H)-one group]

| Example | X | U | R1 | R5 | R6 | R7 |
|---------|-----|---|-----|----------------------------|----------------------------|---|
| 34 | —CH2— | S | —CF3 | —(CH2)2—O—CH3 | 3-(trifluoromethyl)phenyl | |
| 35 | —CH2— | S | —CF3 | —(CH2)2-piperidin-1-yl | 3-(trifluoromethyl)phenyl | |
| 36 | —CH2— | S | —CF3 | —(CH2)2-morpholin-4-yl | 3-(trifluoromethyl)phenyl | |
| 37 | —CH2— | S | —CF3 | —(CH2)2-(1-methylpyrrolidin-2-yl) | 3-(trifluoromethyl)phenyl | |
| 38 | —CH2— | S | H | —(CH2)3CH3 | 4-methoxyphenyl | H |
| 39 | —CH2— | S | F | —(CH2)3—O—CH3 | 4-chlorophenyl | H |
| 40 | —CH2— | S | F | —(CH2)2—O—CH3 | 4-chlorophenyl | H |
| 41 | —CH2— | S | F | —(CH2)2—O—(CH2)2—O—CH3 | 4-chlorophenyl | H | where R2, R3, R4 = H, a dotted line means the point of attachment
If R6 and R7 are bonded to form an annelated ring together with the oxazole respectively the thiazole ring, the upper dotted line means the point of attachment for R6 and the lower dotted line the point of attachment for R7.

The potency of some of the described examples are indicated in the following table:

| Example | PPARalpha EC50 (µM) | PPARdelta EC50 (µM) |
|---------|---------------------|---------------------|
| 9  | 0.06 | 0.02  |
| 14 | 0.07 | 0.004 |
| 23 | 0.82 | 0.65  |
| 24 | 1.35 | 0.27  |
| 28 | 1.02 | 0.06  |
| 33 | 1.10 | 1.80  |
| 39 | 0.36 | 0.20  |

Processes

The compounds of the general formula I according to the invention can be obtained as outlined to the reaction schemes below:

Process A

This process is used for synthesizing compounds of general formula A-7, where X, U, R1, R2, R3, R4, R5, R6, and R7 are as defined.

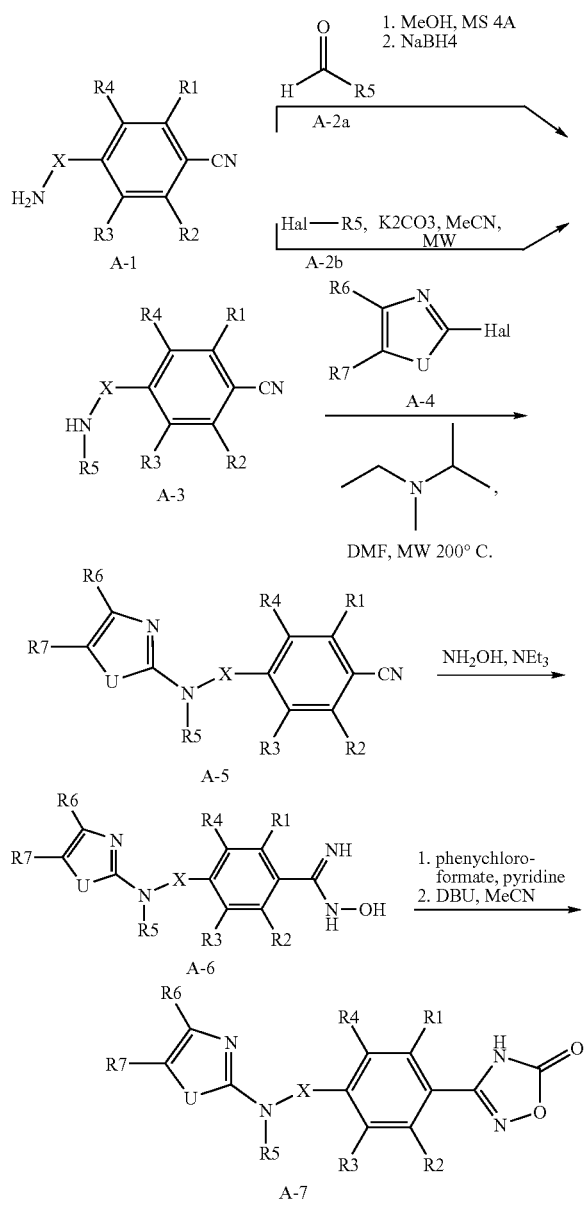

A reductive amination with a primary amine of the general formula A-1 where X, R1, R2, R3 and R4 are as defined and an aldehyde of general formula A-2a where R5 is as defined is performed in a solvent as methanol in the presence of molecular sieves 4 Angström and by addition of a reducing agent as sodium borohydride to give a secondary amine of the general formula A-3. Alternatively the primary amine of the general formula A-1 can be alkylated with an halide of general formula A-2b, where R5 is as defined in a solvent as acetonitrile in presence of a base as potassium carbonate under microwave irradiation to give the secondary amine of the general formula A-3. The amine of general formula A-3 is reacted with an in two position halogenated thiazole, where U is S and R6 and R7 are as defined, or oxazole, where U is O and R6 and R7 are as defined in general formula A-4 under microwave irradiation at elevated temperature, e.g. 200° C., in a solvent as dimethylformamide in the presence of a base as N,N-diisopropylethylamine to give a compound of general formula A-5. The compound of the general formula A-5 is reacted with hydroxylamine hydrochloride in the presence of a base as triethylamine in a solvent as tetrahydrofuran and methanol to obtain a compound of the general formula A-6. A compound of the general formula A-6 is converted to the product of general formula A-7 by reaction with phenylchloroformate in the presence of a base as pyridine and treating this intermediate with a base as 1,8-diazabicyclo[5.4.0]undec-7-ene in a solvent as acetonitrile.

Examples 1-17 were obtained according to process A.

Other compounds can be obtained accordingly or by known processes.

Process B:

This process is used for synthesizing compounds of general formula B-8, where X is —CH2CH2- and U, R1, R2, R3, R4, R5, R6, and R7 are as defined.

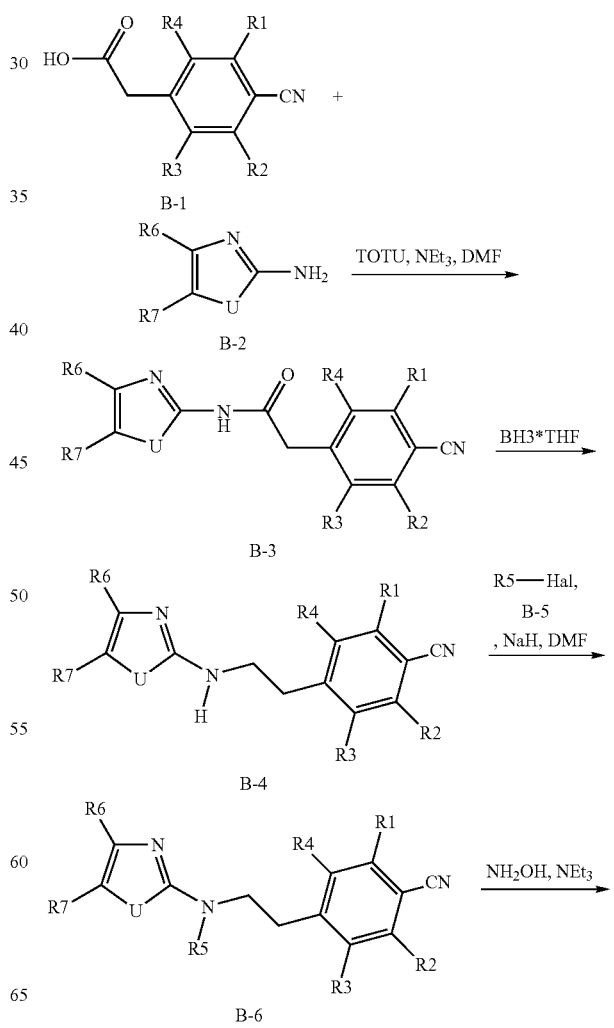

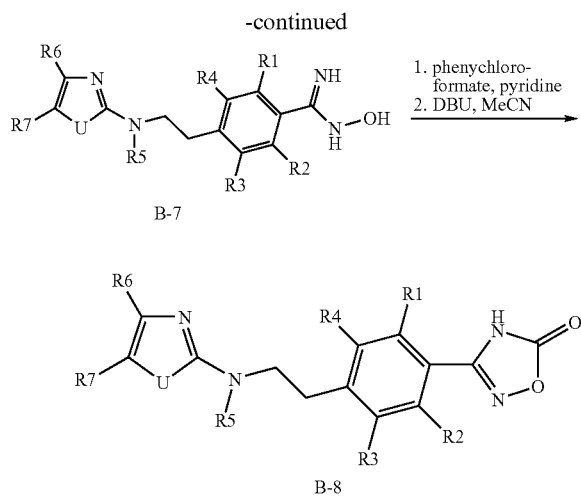

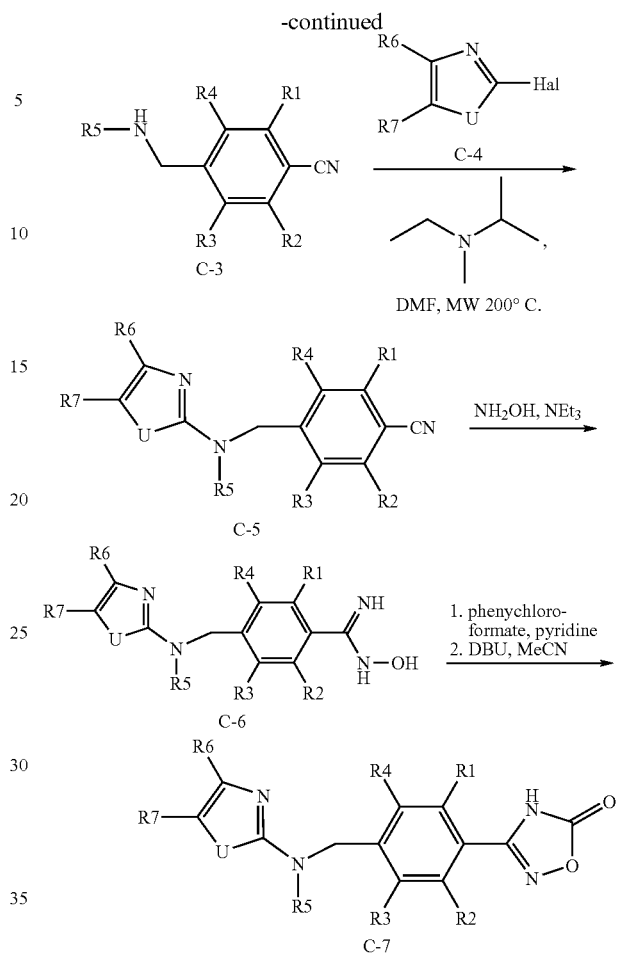

A carboxylic acid of general formula B-1 where R1, R2, R3 and R4 are as defined is condensed with a primary amine of general formula B-2 where R6 and R7 are as defined with a coupling reagent as O-((Ethoxycarbonyl)cyanomethyleneamino)-N,N,N',N'-tetramethyluronium tetrafluoroborate in a solvent as dimethylformamide in the presence of a base as triethylamine to give an amide of the general formula B-3. The amide of general formula B-3 is reduced with a reducing agent as borane tetrahydrofuran complex in a polar aprotic solvent as tetrahydrofuran to obtain a secondary amine of general formula B-4. The secondary amine of general formula B-4 is alkylated with a halide of general formula B-5, where R5 is as defined, in the presence of a base as sodium hydride in a solvent as dimethylformamide to give a tertiary amine of general formula B-6. The compound of the general formula B-6 is reacted with hydroxylamine hydrochloride in the presence of a base as triethylamine in a solvent as tetrahydrofuran and methanol to obtain a compound of the general formula B-7. A compound of the general formula B-7 is converted to the product of general formula B-8 by reaction with phenylchloroformate in the presence of a base as pyridine and treating this intermediate with a base as 1,8-diazabicyclo[5.4.0]undec-7-ene in a solvent as acetonitrile.

Examples 18-23 were obtained according to process B.

Other compounds can be obtained accordingly or by known processes.

Process C:

This process is used for synthesizing compounds of general formula C-7, where X is —CH2— and U, R1, R2, R3, R4, R5, R6, and R7 are as defined.

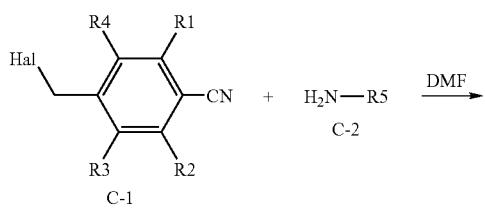

A benzylic halide of general formula C-1 where R1, R2, R3 and R4 are as defined is reacted with a primary amine of general formula C-2 where R5 is as defined in a solvent as dimethylformamide to give a secondary amine of the general formula C-3. The secondary amine of general formula C-3 is reacted with a in two position halogenated thiazole, where U is S and R6 and R7 are as defined or oxazole, where U is O and R6 and R7 are as defined of general formula C-4 under microwave irradiation at elevated temperature, e.g. 200° C., in a solvent as dimethylformamide in the presence of a base as N,N-diisopropylethylamine to give a compound of general formula C-5. The compound of the general formula C-5 is reacted with hydroxylamine hydrochloride in the presence of a base as triethylamine in a solvent as tetrahydrofuran and methanol to obtain a compound of the general formula C-6. A compound of the general formula C-6 is converted to the product of general formula C-7 by reaction with phenylchloroformate in the presence of a base as pyridine and treating this intermediate with a base as 1,8-diazabicyclo[5.4.0]undec-7-ene in a solvent as acetonitrile.

Examples 24-37 were obtained according to process C.

Other compounds can be obtained accordingly or by known processes.

Process D:

This process is used for synthesizing compounds of general formula D-7, where X is —CH2— and U, R1, R2, R3, R4, R5, R6, and R7 are as defined.

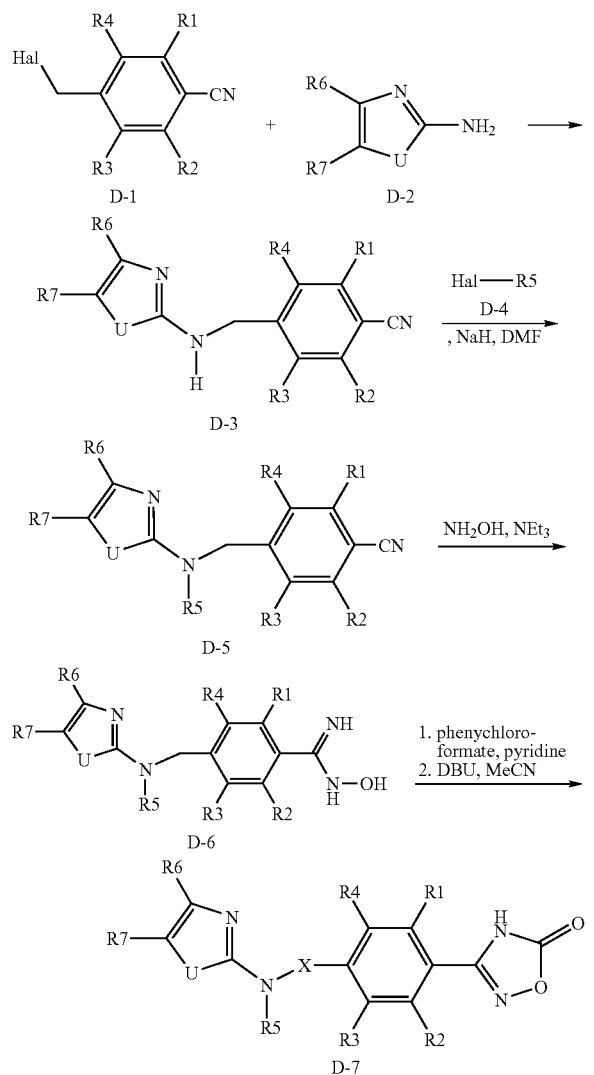

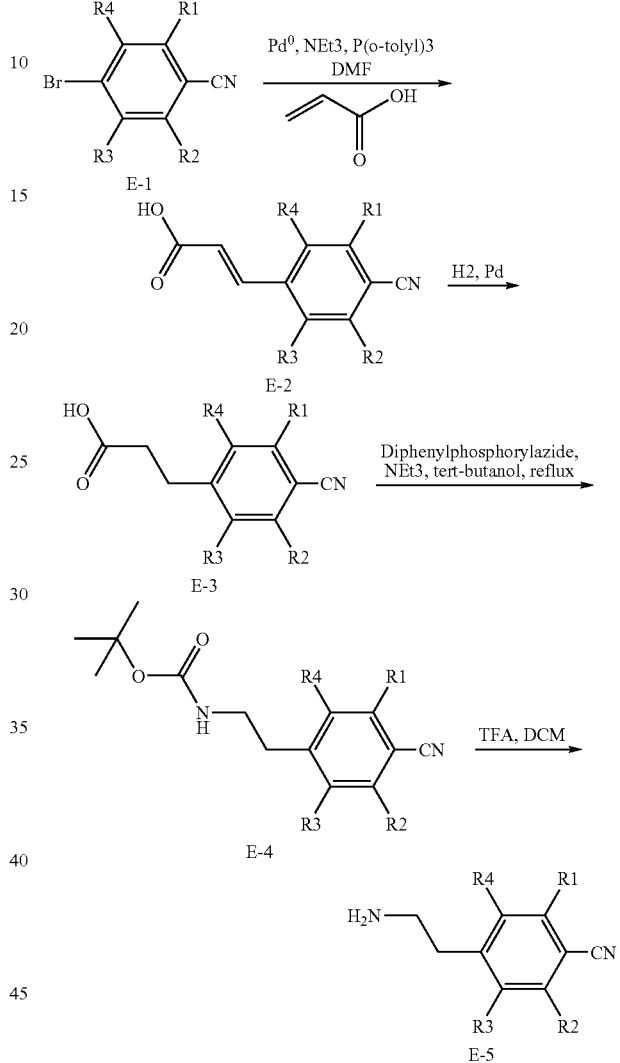

Process E:

This process is used for synthesizing building blocks of general formula E-5, which correspond to general formula A-1 of process A, where X is —CH2CH2— and R1, R2, R3 and R4 are as defined.

A benzylic halide of general formula D-1 where R1, R2, R3 and R4 are as defined is reacted with a 2-amino-thiazole of general formula D-2, where U is S and R6 and R7 are with a 2-amino-oxazole, where U is O and R6 and R7 are as defined of general formula D-2 to give a secondary amine of the general formula D-3.

The secondary amine of general formula D-3 is alkylated with a halide of general formula D-4, where R5 is as defined, in the presence of a base as sodium hydride in a solvent as dimethylformamide to give a tertiary amine of general formula D-5. The compound of the general formula D-5 is reacted with hydroxylamine hydrochloride in the presence of a base as triethylamine in a solvent as tetrahydrofuran and methanol to obtain a compound of the general formula D-6. A compound of the general formula D-6 is converted to the product of general formula D-7 by reaction with phenylchloroformate in the presence of a base as pyridine and treating this intermediate with a base as 1,8-diazabicyclo[5.4.0]undec-7-ene in a solvent as acetonitrile.

Examples 38-41 were obtained according to process D.

Other compounds can be obtained accordingly or by known processes.

A bromobenzonitrile of general formula E-1 is cross coupled with acrylic acid under Heck reaction conditions, in the presence of a palladium source as palladium(II)acetate, a ligand as Tri-o-tolyl-phosphine, a base as triethylamine in a solvent as acetonitrile to give a substituted acrylic acid of general formula E-2. The acrylic acid of general formula E-2 is hydrogenated in the presence of a palladium catalyst as palladium on charcoal (10%) in a solvent as methanol or a mixture of solvents as methanol and tetrahydrofuran under a hydrogen atmosphere to give a carboxylic acid of general formula E-3. The carboxylic acid of general formula E-3 is rearranged to the BOC protected amine of general formula E-4 by treatment with diphenylphosphorylazide in refluxing tert-butanol in the presence of a base as triethylamine. The BOC protecting group of the amine of general formula E-4 is removed by treatment with a base as trifluoroacetic acid in a solvent as dichloromethane to give the primary amine of general formula E-5.

Other compounds can be obtained accordingly or by known processes.

Process F:

This process is used for synthesizing building blocks of general formula F-2, which correspond to general formula C-1 of process C, where Hal is bromine and R1, R2, R3 and R4 are as defined and D-1 of process D, Hal is bromine and R1, R2, R3 and R4 are as defined.

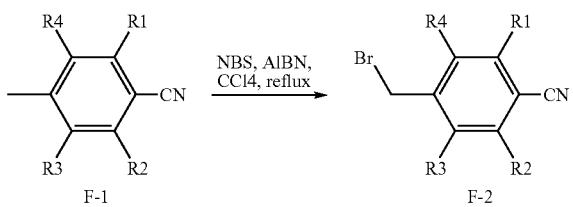

A 4-methyl-benzonitrile of general formula F-1 is brominated by treatment with N-bromosuccinimide in the presence of a radical initiator as 2,2'-azobis(2-methylpropionitrile) in a solvent as tetrachloromethane to give the benzylbromide of general formula F-2.

Other compounds can be obtained accordingly or by known processes.

Process G:

This process is used for synthesizing building blocks of general formula G-2, which correspond to general formula A-4 of process A, where Hal is chlorine, U is S and R6 and R7 are as defined and C-4 of process C, where Hal is chlorine, U is S and R6 and R7 are as defined.

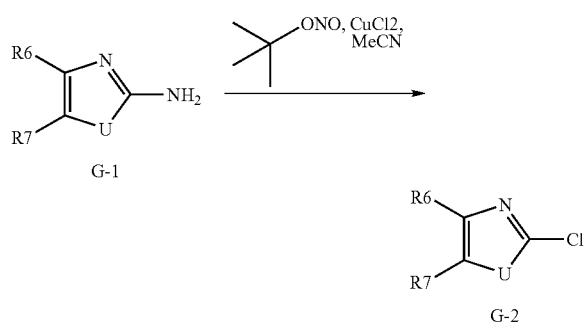

A 2-amino-thiazole of general formula G-1, where U is S and R6 and R7 are as defined or a 2-amino-oxazole, where U is O and R6 and R7 are as defined is reacted with tert-butyl-nitrite and copper(II)chloride in a solvent as acetonitrile to give a 2-halogenated compound of general formula G-2.

Other compounds can be obtained accordingly or by known processes.

LIST OF ABBREVIATION

| | |
|---|---|
| Ac | acetyl |
| AIBN | 2,2'-azobis(2-methylpropionitrile) |
| Bn | benzyl |
| BOC | tert-butyl-oxy-carbonyl |
| iBu | isobutyl |
| tBu | tert-Butyl |

-continued

| | |
|---|---|
| BuLi | n-butyllithium |
| Bz | benzoyl |
| Cy | cyclohexyl |
| DBU | 1,8-diazabicyclo[5.4.0]undec-7-ene |
| DCI | direct chemical ionization (MS) |
| DCM | dichloromethane |
| DMAP | N,N-dimethylaminopyridine |
| DMF | N,N-dimethylformamide |
| DMSO | dimethylsulfoxide |
| EE | ethyl acetate |
| eq | equivalents |
| ESI | electrospray-Ionisation (MS) |
| FG | leaving group |
| GC | gas chromatography |
| Hal | halogen |
| HPLC | high performance liquid chromatography |
| LC-MS | liquid chromatography coupled with mass-spectroscopy |
| Me | methyl |
| MeCN | acetonitrile |
| MS | mass-spectroscopy |
| MS 4A | molecular sieves four angström |
| MsCl | methansulfonylchloride |
| MW | micro wave |
| NBS | N-bromosuccinimide |
| NMR | nuclear magnetic resonance |
| p | para |
| Pd/C | palladium on carbon |
| iPr | isopropyl |
| nPr | n-propyl |
| Rf | retention factor (TLC) |
| tert | tertiary |
| TFA | trifluoroacetic acid |
| THF | tetrahydrofuran |
| TLC | thin layer chromatography |
| TOTU | O-((Ethoxycarbonyl)cyanomethyleneamino)-N,N,N',N'-tetramethyluronium tetrafluoroborat |

Further compounds of the formula I can be prepared correspondingly or by known processes.

The experimental procedures for preparing the examples mentioned above are described below:

Building Block Synthesis According to Process E:

4-(2-Amino-ethyl)-2-methyl-benzonitrile

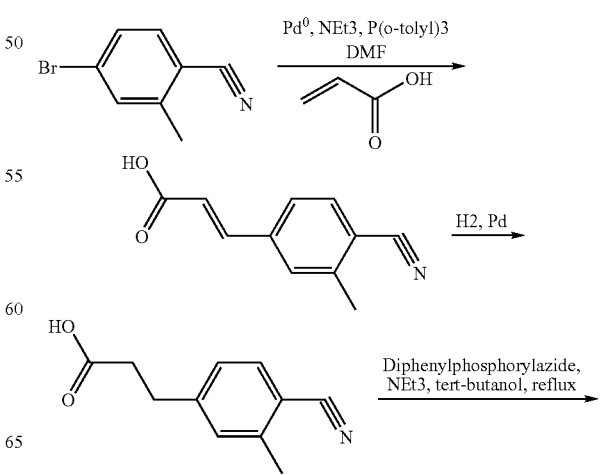

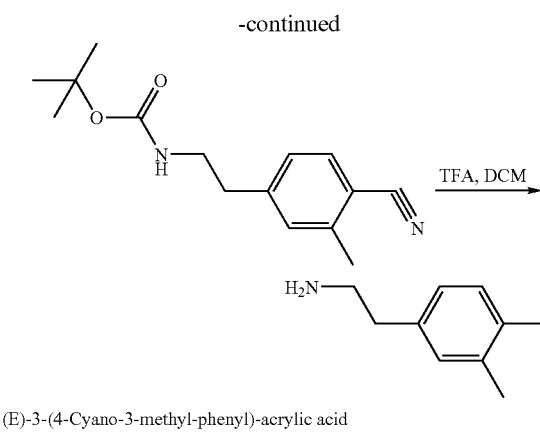

(E)-3-(4-Cyano-3-methyl-phenyl)-acrylic acid

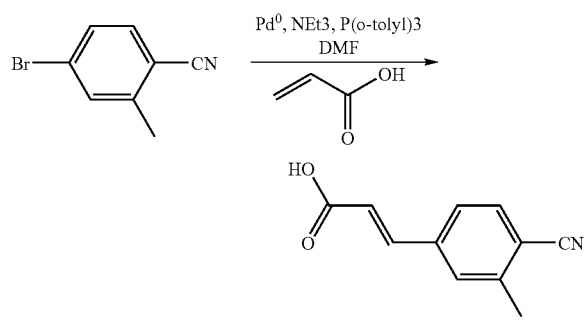

9.0 g 4-bromo-2-methylbenzonitrile, 2.76 g tri-o-tolylphosphine, 3.11 ml acrylic acid and 25.1 ml triethylamine are dissolved in 80 ml acetonitrile. The reaction mixture is degassed, then 2.0 g palladium (II)acetate were added and the mixture stirred two hours under microwave irradiation at 200° C. The cooled reaction mixture was diluted by addition of 50 ml ethyl acetate. Thereby (E)-3-(4-Cyano-3-methyl-phenyl)-acrylic acid precipitated as a white solid. The precipitate was filtered off and dried in vacuo to obtain 2.5 g (E)-3-(4-Cyano-3-methyl-phenyl)-acrylic acid. The filtrate was washed with 1N HCl, thereby (E)-3-(4-Cyano-3-methyl-phenyl)-acrylic acid precipitated again as a white solid. The precipitate was filtered off and dried in vacuo to obtain 2.0 g (E)-3-(4-Cyano-3-methyl-phenyl)-acrylic acid. The filtrate was reduced in vacuo to one third of its volume, 150 ml diethyl ether were added, thereby (E)-3-(4-Cyano-3-methyl-phenyl)-acrylic acid precipitated again as a white solid. The precipitate was filtered off and dried in vacuo to obtain 840 mg (E)-3-(4-Cyano-3-methyl-phenyl)-acrylic acid C11H9NO2 (187.20), MS (ESI): 188.1 (M+H$^+$), Rf(ethyl acetate: methanol=9:1)=0.16.

3-(4-Cyano-3-methyl-phenyl)-propionic acid

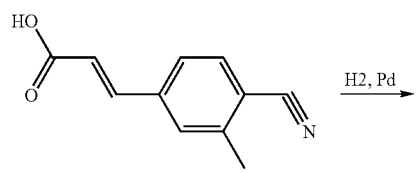

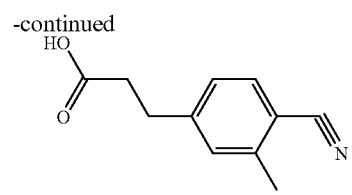

5.15 g (E)-3-(4-Cyano-3-methyl-phenyl)-acrylic acid were dissolved in a mixture of 250 ml tetrahydrofuran and 125 ml methanol. 510 mg palladium on charcoal (10%) were added and the reaction mixture was stirred under a hydrogen atmosphere overnight. The catalyst was filtered off over a celite pad. The solvent was removed in vacuo to obtain 5.2 g 3-(4-Cyano-3-methyl-phenyl)-propionic acid as a white solid.

C11H11NO2 (189.22), MS (ESI): 190.2 (M+H$^+$).

4-(2-Amino-ethyl)-2-methyl-benzonitrile

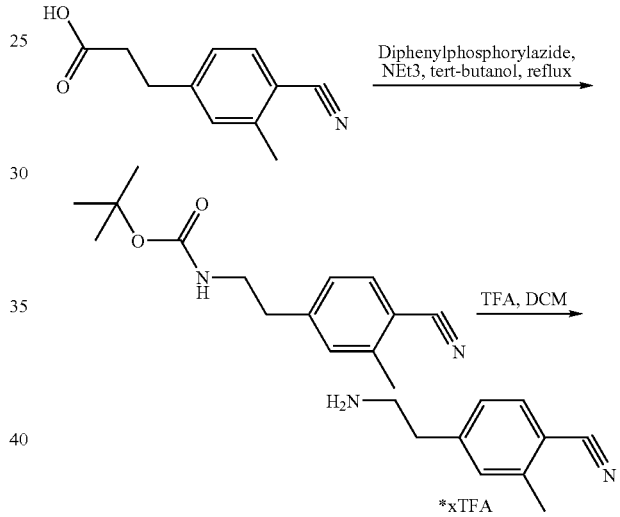

To a solution of 5.20 g 3-(4-Cyano-3-methyl-phenyl)-propionic acid and 4.57 ml triethylamine in 100 ml tert-butanol 9.10 g diphenylphosphorylazide were given and the mixture heated under reflux overnight. The cooled reaction mixture was evaporated in vacuo. The resulting residue was dissolved in 150 ml ethyl acetate, washed with 50 ml citric acid/brine=1:1 and 50 ml saturated NaHCO3 solution and then dried over MgSO4. The residue was dissolved in 50 ml dichloromethane and 20 ml trifluoroacetic acid were added. The reaction mixture was stirred at room temperature for two hours. The solvent was removed in vacuo. The residue was coevaporated four times with portions of 100 ml toluene. The resulting brown residue was taken up in 50 ml acetonitrile and stirred at room temperature. The solid material was filtered off and dried in vacuo to obtain 2.45 g 4-(2-Amino-ethyl)-2-methyl-benzonitrile as its trifluoroacetate salt. The filtrate was evaporated in vacuo, the resulting residue was taken up in 100 ml diethyl ether and stirred at room temperature. The solid material was filtered off and dried in vacuo to obtain 1.17 g 4-(2-Amino-ethyl)-2-methyl-benzonitrile as its trifluoroacetate salt.

C10H12N2*xTFA (160.22+xTFA), MS (ESI): 161.1 (M+H+).

Building Block Synthesis According To Process F:

4-Bromomethyl-2-trifluoromethyl-benzonitrile

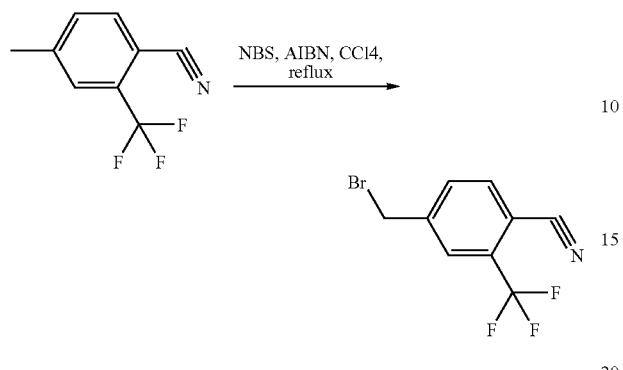

To a refluxing mixture of 5.0 g 4-Methyl-2-(trifluoromethyl)benzonitrile in 50 ml tetrachloromethane were added a mixture of 5.77 g N-bromosuccinimide and 1.77 g 2,2'-azobis (2-methylpropionitrile). The reaction mixture was heated under reflux for three hours. The reaction mixture was filtered through a pad of celite and the solvent was removed in vacuo to obtain 11.2 g crude 4-Bromomethyl-2-trifluoromethyl-benzonitrile (impurified with the dibromo product) as a white solid. This material was used without further purification.

C9H5BrF3N (264.05), MS (ESI): 264.0, 266.0 (M+H$^+$), Rf(n-heptane:ethyl acetate=4:1)=0.25.

Building Block Synthesis According To Process G:

2-Chloro-6-trifluoromethyl-benzothiazole 8.25 ml tert-butyl nitrite were added to a solution of 7.40 g copper (II) chloride in 120 ml acetonitrile. The reaction mixture was stirred ten minutes at room temperature. Then a solution of 10.0 g 2-Amino-6-(trifluoromethyl)benzonitrile were added. Then 100 ml 1N HCl were added to the cooled reaction mixture. The reaction mixture was extracted five times with portions of 50 ml ethyl acetate. The combined organic layers were washed with water and the dried over MgSO4. The solvent was removed in vacuo to obtain 9.79 g crude 2-Chloro-6-trifluoromethyl-benzothiazole as a red oil which solidifies upon standing. This material was used without further purification.

C8H3ClF3NS (237.63), MS (GC): 237.0 (M+H$^+$), Rf(n-heptane:ethyl acetate=1:1)=0.72.

The following examples were prepared according to process A:

EXAMPLE 1

3-{4-[2-(Benzooxazol-2-yl-butyl-amino)-ethyl]-phenyl}-4H-[1,2,4]oxadiazol-5-one

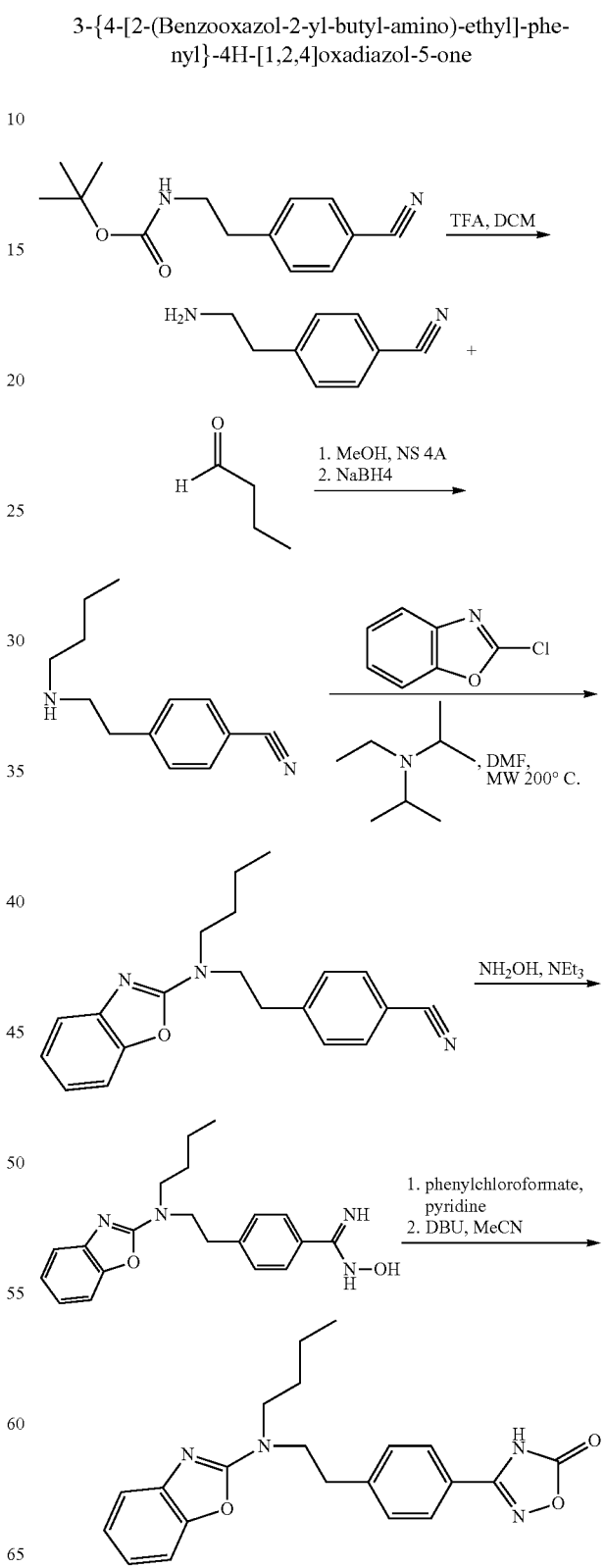

4-(2-Amino-ethyl)-benzonitrile

4-[2-(Benzooxazol-2-yl-butyl-amino)-ethyl]-benzonitrile

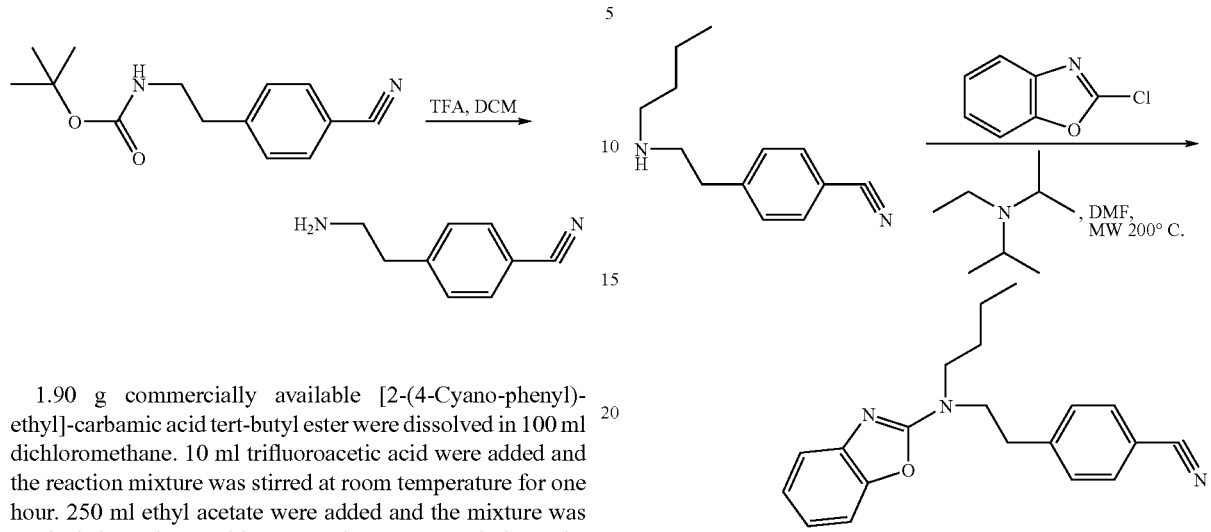

1.90 g commercially available [2-(4-Cyano-phenyl)-ethyl]-carbamic acid tert-butyl ester were dissolved in 100 ml dichloromethane. 10 ml trifluoroacetic acid were added and the reaction mixture was stirred at room temperature for one hour. 250 ml ethyl acetate were added and the mixture was washed three times with saturated NaHCO3 solution. The organic layer was dried over MgSO4 and then the solvent was removed in vacuo to obtain 700 mg 4-(2-Amino-ethyl)-benzonitrile as pale yellow solid.

C9H10N2 (146.19), MS (ESI): 147.1 (M+H$^+$).

4-(2-Butylamino-ethyl)-benzonitrile

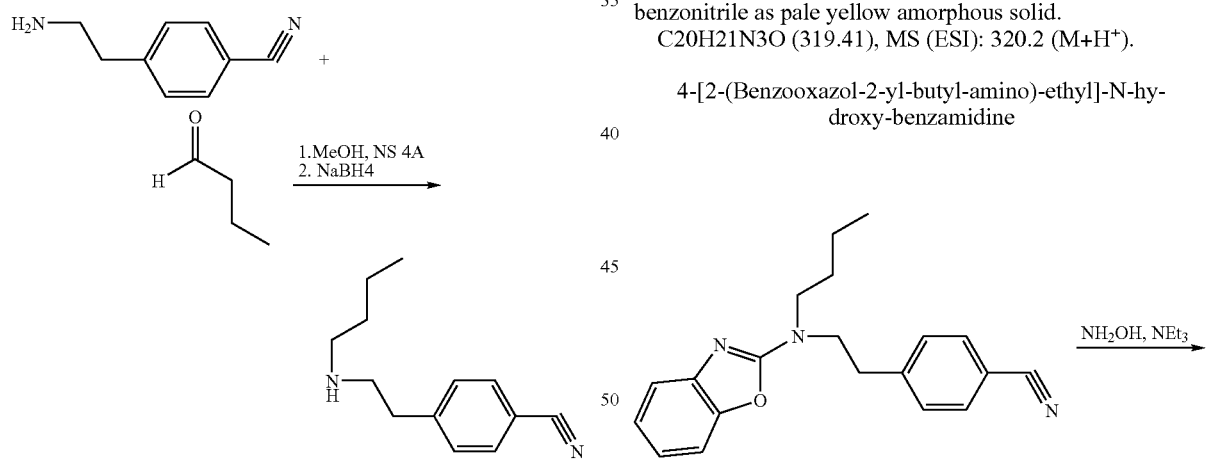

700 mg 4-(2-Amino-ethyl)-benzonitrile and 63 μl Butyraldehyde were dissolved in 20 ml methanol. 1.0 g molecular sieves 4 Angström were added the mixture was stirred at room temperature for two hours. Then 270 mg sodium borohydride were added and the mixture was stirred for an additional hour at room temperature. 100 ml ethyl acetate were added, and the reaction was quenched by addition of 1 ml water. The reaction mixture was filtered through a pad of celite and MgSO4. The filtrate was evaporated in vacuo to provide 750 mg crude 4-(2-Butylamino-ethyl)-benzonitrile. This material was used without further purification.

C13H18N2 (202.30), MS (ESI): 203.2 (M+H$^+$).

A solution of 750 mg 4-(2-Butylamino-ethyl)-benzonitrile, 854 mg 2-chlorobenzooxazole and 0.95 ml N,N-diisopropylethylamine in 10 ml dimethylformamide were stirred under microwave irradiation at 200° C. for thirty minutes. The cooled reaction mixture was diluted by the addition of 60 ml ethyl acetate, then washed three times with 40 ml brine. The organic layer was dried over MgSO4, then the solvent was removed in vacuo. The residue was purified by RP-HPLC to obtain 290 mg 4-[2-(Benzooxazol-2-yl-butyl-amino)-ethyl]-benzonitrile as pale yellow amorphous solid.

C20H21N3O (319.41), MS (ESI): 320.2 (M+H$^+$).

4-[2-(Benzooxazol-2-yl-butyl-amino)-ethyl]-N-hydroxy-benzamidine 290 mg 4-[2-(Benzooxazol-2-yl-butyl-amino)-ethyl]-benzonitrile were dissolved in a mixture of 10 ml tetrahydrofuran and 20 ml methanol. 930 mg hydroxylamine hydrochloride were added followed by the addition of 2.24 ml triethylamine.

The reaction mixture was stirred at 65° C. for two hours. The cooled reaction mixture was diluted by the addition of 100 ml ethyl acetate, then washed three times with 40 ml water. The organic layer was dried over MgSO4, then the solvent was removed in vacuo to obtain 280 mg 4-[2-(Benzooxazol-2-yl-butyl-amino)-ethyl]-N-hydroxy-benzamidine as a pale yellow oil.

C20H24N4O2 (352.44), MS (ESI): 353.2 (M+H$^+$).

3-{4-[2-(Benzooxazol-2-yl-butyl-amino)-ethyl]-phenyl}-4H-[1,2,4]oxadiazol-5-one

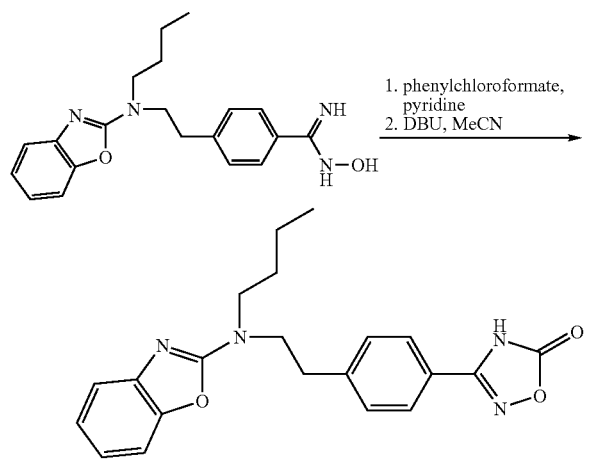

280 mg 4-[2-(Benzooxazol-2-yl-butyl-amino)-ethyl]-N-hydroxy-benzamidine were dissolved in 5 ml dichloromethane. 78 µl pyridine and 120 µl phenylchloroformate were added and the mixture stirred at room temperature for ten minutes. The mixture was diluted by the addition of 15 ml acetonitrile and 115 µl ml 1,8-Diazabicyclo[5.4.0]undec-7-ene were added. The mixture was stirred at room temperature for 10 minutes. The mixture was evaporated in vacuo and the resulting crude material was purified by reversed phase HPLC to obtain 105 mg 3-{4-[2-(Benzooxazol-2-yl-butyl-amino)-ethyl]-phenyl}-4H-[1,2,4]oxadiazol-5-one as an amorphous lyophilisate.

C21H22N4O3 (378.43), MS (ESI): 379.2 (M+H$^+$).

EXAMPLE 2

3-{4-[2-(Benzothiazol-2-yl-butyl-amino)-ethyl]-phenyl}-4H-[1,2,4]oxadiazol-5-one

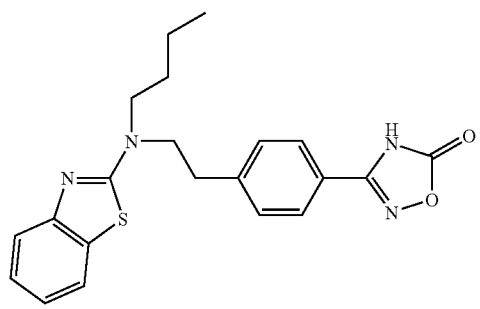

According to the method described in Example 1 3-{4-[2-(Benzothiazol-2-yl-butyl-amino)-ethyl]-phenyl}-4H-[1,2,4]oxadiazol-5-one was obtained from 4-(2-Butylamino-ethyl)-benzonitrile and commercially available 2-chlorobenzothiazole.

C21H22N4O2S (394.50), MS (ESI): 395.2 (M+H$^+$).

EXAMPLE 3

3-(4-{2-[Butyl-(6-methoxy-benzothiazol-2-yl)-amino]-ethyl}-phenyl)-4H-[1,2,4]oxadiazol-5-one

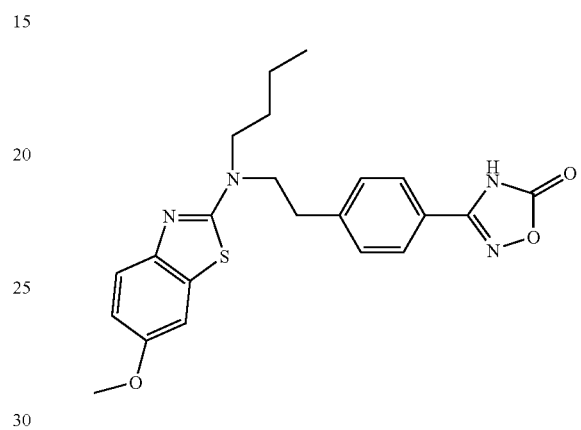

According to the method described in Example 1 3-(4-{2-[Butyl-(6-methoxy-benzothiazol-2-yl)-amino]-ethyl}-phenyl)-4H-[1,2,4]oxadiazol-5-one was obtained from 4-(2-Butylamino-ethyl)-benzonitrile and commercially available 2-Chloro-6-methoxy-benzothiazole.

C22H24N4O3S (424.53), MS (ESI): 425.2 (M+H$^+$).

EXAMPLE 4

3-(4-{2-[Butyl-(6-chloro-benzothiazol-2-yl)-amino]-ethyl}-phenyl)-4H-[1,2,4]oxadiazol-5-one

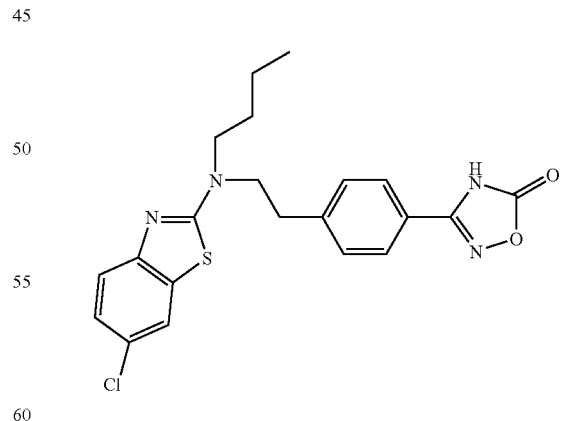

According to the method described in Example 1 3-(4-{2-[Butyl-(6-chloro-benzothiazol-2-yl)-amino]-ethyl}-phenyl)-4H-[1,2,4]oxadiazol-5-one was obtained from 4-(2-Butylamino-ethyl)-benzonitrile and commercially available 2,6-dichlorobenzothiazole.

C21H21ClN4O2S (428.94), MS (ESI): 429.2 (M+H$^+$).

EXAMPLE 5

3-(4-{2-[Butyl-(6-chloro-benzothiazol-2-yl)-amino]-ethyl}-2-methyl-phenyl)-4H-[1,2,4]oxadiazol-5-one

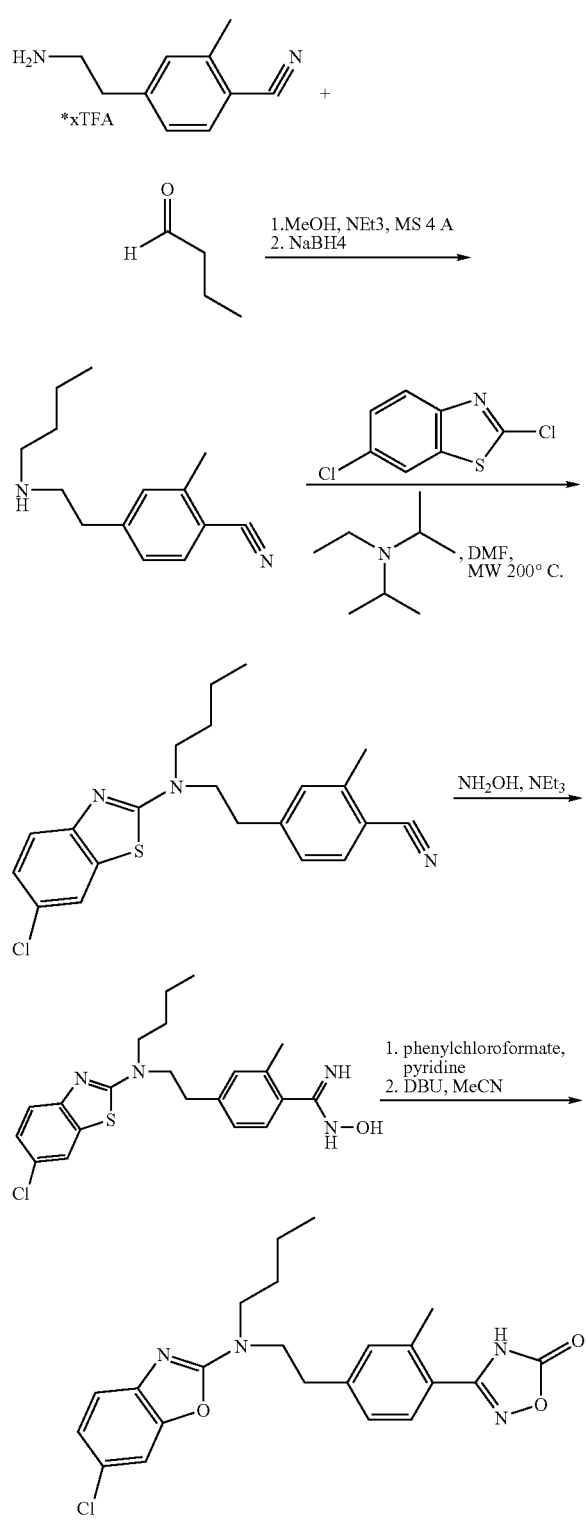

4-(2-Butylamino-ethyl)-2-methyl-benzonitrile

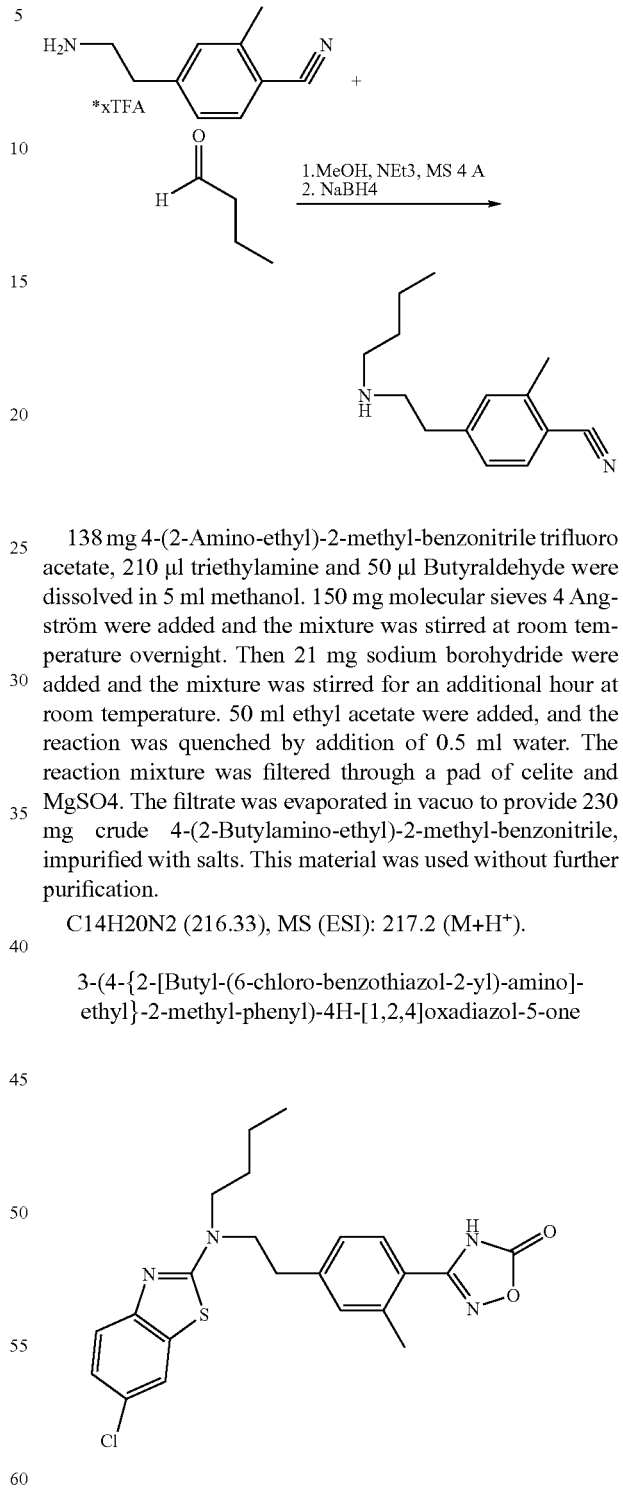

138 mg 4-(2-Amino-ethyl)-2-methyl-benzonitrile trifluoro acetate, 210 µl triethylamine and 50 µl Butyraldehyde were dissolved in 5 ml methanol. 150 mg molecular sieves 4 Angström were added and the mixture was stirred at room temperature overnight. Then 21 mg sodium borohydride were added and the mixture was stirred for an additional hour at room temperature. 50 ml ethyl acetate were added, and the reaction was quenched by addition of 0.5 ml water. The reaction mixture was filtered through a pad of celite and MgSO4. The filtrate was evaporated in vacuo to provide 230 mg crude 4-(2-Butylamino-ethyl)-2-methyl-benzonitrile, impurified with salts. This material was used without further purification.

C14H20N2 (216.33), MS (ESI): 217.2 (M+H$^+$).

3-(4-{2-[Butyl-(6-chloro-benzothiazol-2-yl)-amino]-ethyl}-2-methyl-phenyl)-4H-[1,2,4]oxadiazol-5-one According to the method described in Example 1 3-(4-{2-[Butyl-(6-chloro-benzothiazol-2-yl)-amino]-ethyl}-2-methyl-phenyl)-4H-[1,2,4]oxadiazol-5-one was obtained from 4-(2-Butylamino-ethyl)-2-methyl-benzonitrile and commercially available 2,6-dichlorobenzothiazole.

C22H23ClN4O2S (442.97), MS (ESI): 443.1 (M+H$^+$).

EXAMPLE 6

3-(4-{2-[Butyl-(6-trifluoromethyl-benzothiazol-2-yl)-amino]-ethyl}-2-methyl-phenyl)-4H-[1,2,4]oxadiazol-5-one

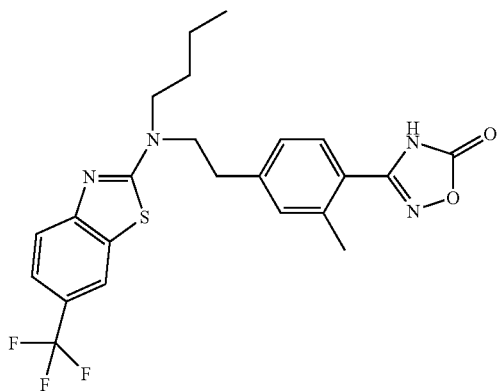

According to the method described in Example 1 3-(4-{2-[Butyl-(6-trifluoromethyl-benzothiazol-2-yl)-amino]-ethyl}-2-methyl-phenyl)-4H-[1,2,4]oxadiazol-5-one was obtained from 4-(2-Butylamino-ethyl)-2-methyl-benzonitrile and 2-Chloro-6-trifluoromethyl-benzothiazole.

C23H23F3N4O2S (476.52), MS (ESI): 477.2 (M+H$^+$).

EXAMPLE 7

3-(2-Methyl-4-{2-[[2-(tetrahydro-pyran-4-yl)-ethyl]-(6-trifluoromethyl-benzothiazol-2-yl)-amino]-ethyl}-phenyl)-4H-[1,2,4]oxadiazol-5-one

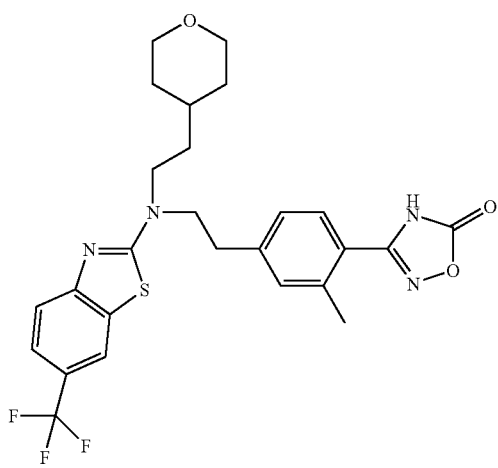

According to the method described in Example 1 and 5 3-(2-Methyl-4-{2-[[2-(tetrahydro-pyran-4-yl)-ethyl]-(6-trifluoromethyl-benzothiazol-2-yl)-amino]-ethyl}-phenyl)-4H-[1,2,4]oxadiazol-5-one was obtained from 4-(2-Amino-ethyl)-2-methyl-benzonitrile trifluoro acetate, (tetrahydro-pyran-4-yl)-acetaldehyde and 2-Chloro-6-trifluoromethyl-benzothiazole.

C26H27F3N4O3S (532.59), MS (ESI): 533.1 (M+H$^+$).

EXAMPLE 8

3-(2-Methyl-4-{2-[(tetrahydro-pyran-3-ylmethyl)-(6-trifluoromethyl-benzothiazol-2-yl)-amino]-ethyl}-phenyl)-4H-[1,2,4]oxadiazol-5-one

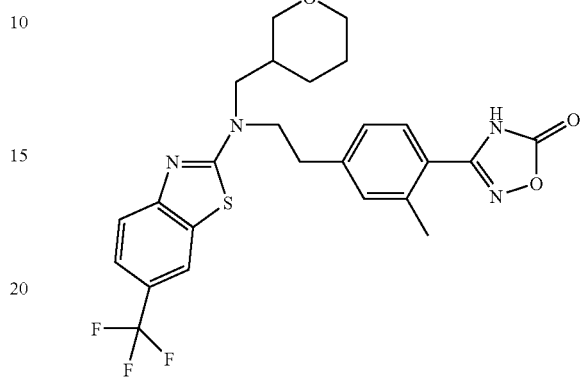

According to the method described in Example 1 and 5 3-(2-Methyl-4-{2-[(tetrahydro-pyran-3-ylmethyl)-(6-trifluoromethyl-benzothiazol-2-yl)-amino]-ethyl}-phenyl)-4H-[1,2,4]oxadiazol-5-one was obtained from 4-(2-Amino-ethyl)-2-methyl-benzonitrile trifluoro acetate, tetrahydropyranyl-3-carboxaldehyde and 2-Chloro-6-trifluoromethyl-benzothiazole.

C25H25F3N4O3S (518.56), MS (ESI): 519.1 (M+H$^+$).

EXAMPLE 9

3-(2-Methyl-4-{2-[(tetrahydro-pyran-4-ylmethyl)-(6-trifluoromethyl-benzothiazol-2-yl)-amino]-ethyl}-phenyl)-4H-[1,2,4]oxadiazol-5-one

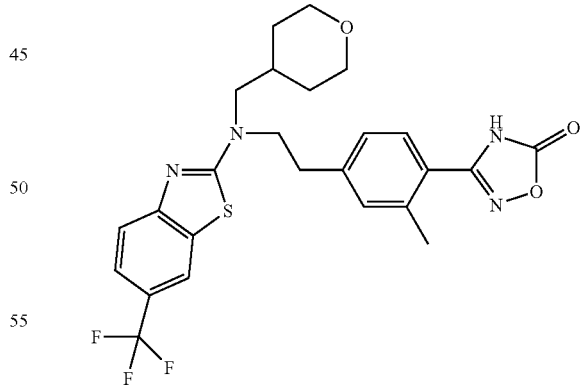

According to the method described in Example 1 and 5 3-(2-Methyl-4-{2-[(tetrahydro-pyran-4-ylmethyl)-(6-trifluoromethyl-benzothiazol-2-yl)-amino]-ethyl}-phenyl)-4H-[1,2,4]oxadiazol-5-one was obtained from 4-(2-Amino-ethyl)-2-methyl-benzonitrile trifluoro acetate, tetrahydropyranyl-4-carboxaldehyde and 2-Chloro-6-trifluoromethyl-benzothiazole.

C25H25F3N4O3S (518.56), MS (ESI): 519.1 (M+H$^+$).

EXAMPLE 10
3-(4-{2-[[2-(1-Acetyl-piperidin-4-yl)-ethyl]-(6-trifluoromethyl-benzothiazol-2-yl)-amino]-ethyl}-2-methyl-phenyl)-4H-[1,2,4]oxadiazol-5-one
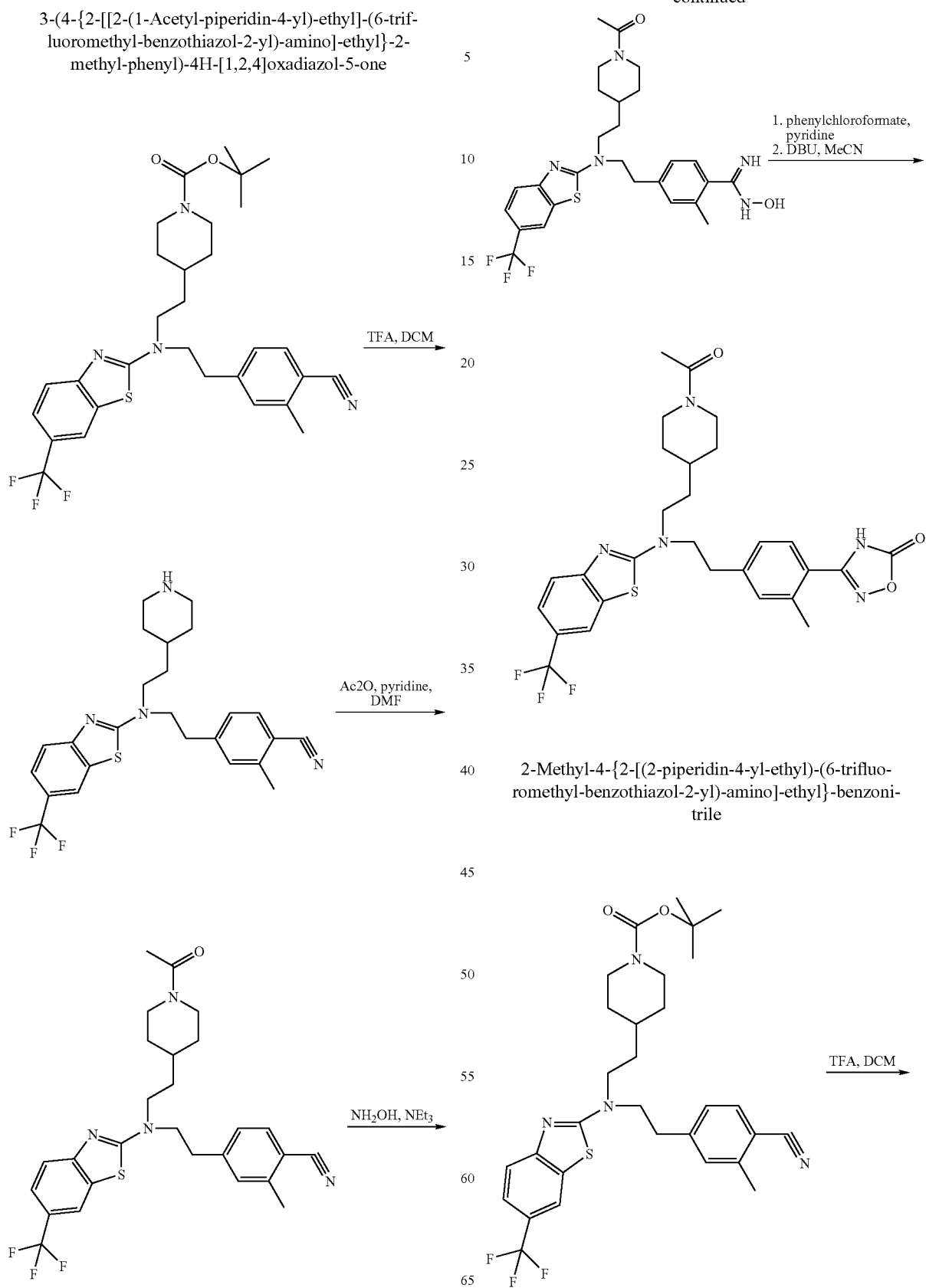
2-Methyl-4-{2-[(2-piperidin-4-yl-ethyl)-(6-trifluoromethyl-benzothiazol-2-yl)-amino]-ethyl}-benzonitrile

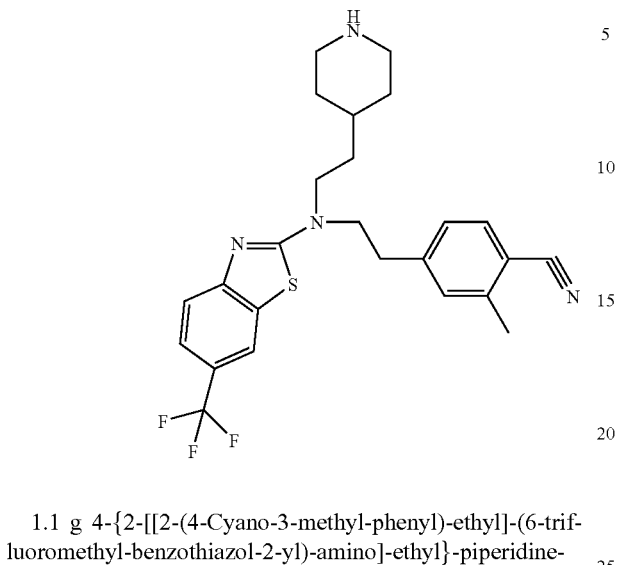

1.1 g 4-{2-[[2-(4-Cyano-3-methyl-phenyl)-ethyl]-(6-trifluoromethyl-benzothiazol-2-yl)-amino]-ethyl}-piperidine-1-carboxylic acid tert-butyl ester [prepared according to the method described in Example 1 and 5 from 4-(2-Aminoethyl)-2-methyl-benzonitrile trifluoro acetate, N-boc-piperidinyl-4-acetaldehyde and 2-Chloro-6-trifluoromethyl-benzothiazole] were dissolved in 50 ml dichloromethane. 5 ml trifluoroacetic acid were added and the reaction mixture was stirred at room temperature for one hour. 150 ml ethyl acetate were added and the mixture was washed three times with saturated NaHCO3 solution. The organic layer was dried over MgSO4 and then the solvent was removed in vacuo. The residue was purified by RP-HPLC to obtain 325 mg 2-Methyl-4-{2-[(2-piperidin-4-yl-ethyl)-(6-trifluoromethyl-benzothiazol-2-yl)-amino]-ethyl}-benzonitrile.

C25H27F3N4S (472.58), MS (ESI): 473.2 (M+H$^+$).

4-{2-[[2-(1-Acetyl-piperidin-4-yl)-ethyl]-(6-trifluoromethyl-benzothiazol-2-yl)-amino]-ethyl}-2-methyl-benzonitrile

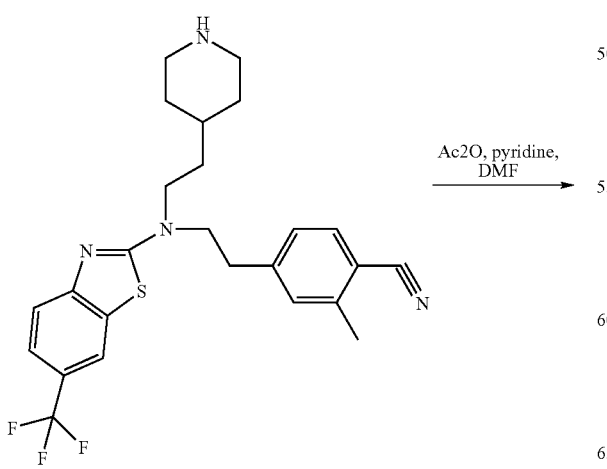

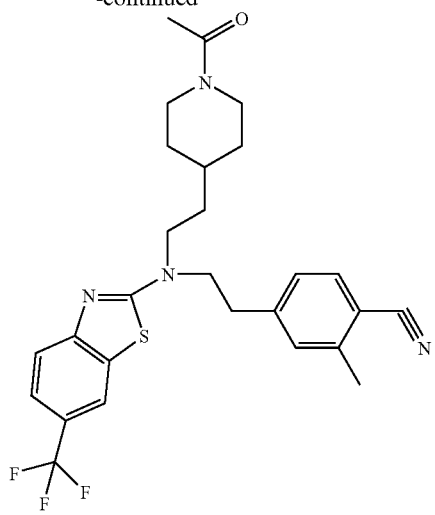

160 mg 4-{2-[[2-(1-Acetyl-piperidin-4-yl)-ethyl]-(6-trifluoromethyl-benzothiazol-2-yl)-amino]-ethyl}-2-methyl-benzonitrile were dissolved in 2.5 ml dimethylformamide. 5 ml pyridine and 26 µl acetic acid anhydride were added. After being stirred at room temperature for thirty minutes, the reaction mixture was evaporated in vacuo to obtain 140 mg crude 4-{2-[[2-(1-Acetyl-piperidin-4-yl)-ethyl]-(6-trifluoromethyl-benzothiazol-2-yl)-amino]-ethyl}-2-methyl-benzonitrile which was used in the next step without further purification.

C27H29F3N4OS (514.62), MS (ESI): 515.2 (M+H$^+$).

3-(4-{2-[[2-(1-Acetyl-piperidin-4-yl)-ethyl]-(6-trifluoromethyl-benzothiazol-2-yl)-amino]-ethyl}-2-methyl-phenyl)-4H-[1,2,4]oxadiazol-5-one

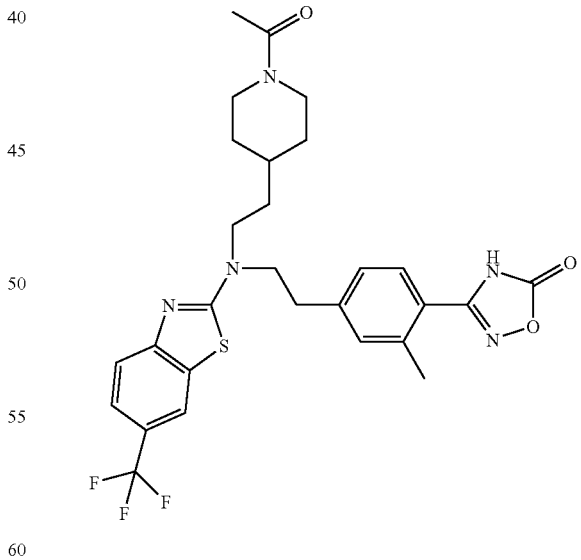

According to the method described in Example 1 3-(4-{2-[[2-(1-Acetyl-piperidin-4-yl)-ethyl]-(6-trifluoromethyl-benzothiazol-2-yl)-amino]-ethyl}-2-methyl-phenyl)-4H-[1,2,4]oxadiazol-5-one was obtained from 4-{2-[[2-(1-Acetyl-piperidin-4-yl)-ethyl]-(6-trifluoromethyl-benzothiazol-2-yl)-amino]-ethyl}-2-methyl-benzonitrile.

C28H30F3N5O3S (573.64), MS (ESI): 574.2 (M+H$^+$).

EXAMPLE 11

3-{4-[(Benzooxazol-2-yl-butyl-amino)-methyl]-phenyl}-4H-[1,2,4]oxadiazol-5-one

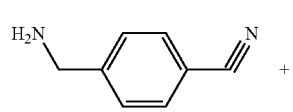

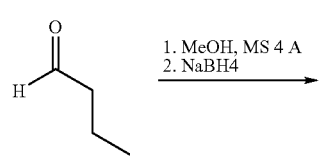

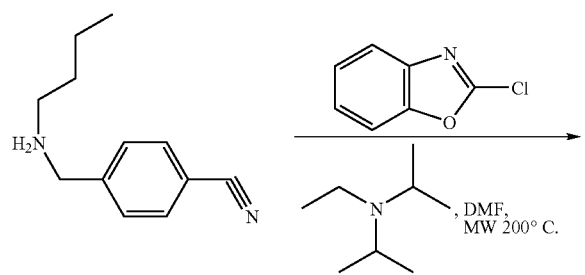

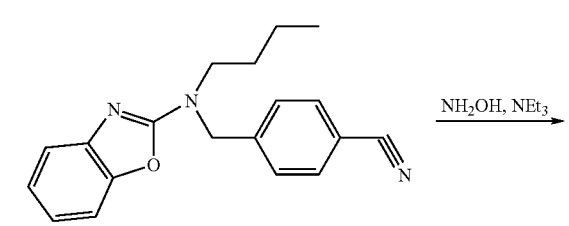

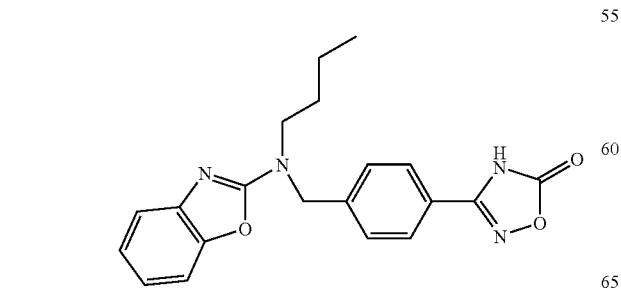

4-Butylaminomethyl-benzonitrile

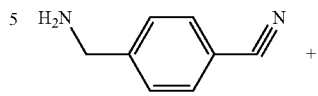

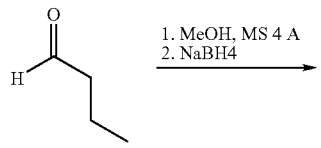

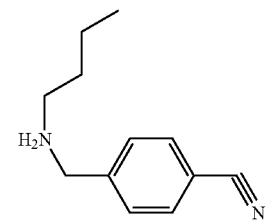

5.0 g 4-Aminomethyl-benzonitrile and 3.75 ml Butyraldehyde were dissolved in 40 ml methanol. 3.0 g molecular sieves 4 Angström were added and the mixture was stirred at room temperature for two hours. Then 2.2 g sodium borohydride were added and the mixture was stirred for an additional hour at room temperature. 250 ml ethyl acetate were added, and the reaction was quenched by addition of 4 ml water. The reaction mixture was filtered through a pad of celite and MgSO4. The filtrate was evaporated in vacuo to provide 3.7 g crude 4-Butylaminomethyl-benzonitrile. This material was used without further purification.

C12H16N2 (188.27), MS (ESI): 189.2 (M+H$^+$).

3-{4-[(Benzooxazol-2-yl-butyl-amino)-methyl]-phenyl}-4H-[1,2,4]oxadiazol-5-one According to the method described in Example 1 3-{4-[(Benzooxazol-2-yl-butyl-amino)-methyl]-phenyl}-4H-[1,2,4]oxadiazol-5-one was obtained from 4-butylaminomethyl-benzonitrile and 2-chlorobenzoxazole.

C20H20N4O3 (364.41), MS (ESI): 365.2 (M+H⁺).

EXAMPLE 12

3-{4-[(Benzothiazol-2-yl-butyl-amino)-methyl]-phenyl}-4H-[1,2,4]oxadiazol-5-one

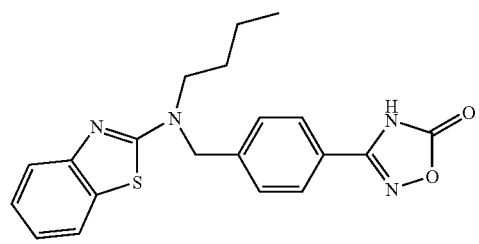

According to the method described in Example 1 3-{4-[(Benzothiazol-2-yl-butyl-amino)-methyl]-phenyl}-4H-[1,2,4]oxadiazol-5-one was obtained from 4-butylaminomethyl-benzonitrile and 2-chlorobenzothiazole.

C20H20N4O2S (380.47), MS (ESI): 381.2 (M+H⁺).

EXAMPLE 13

3-(4-{[Butyl-(6-chloro-benzothiazol-2-yl)-amino]-methyl}-phenyl)-4H-[1,2,4]oxadiazol-5-one

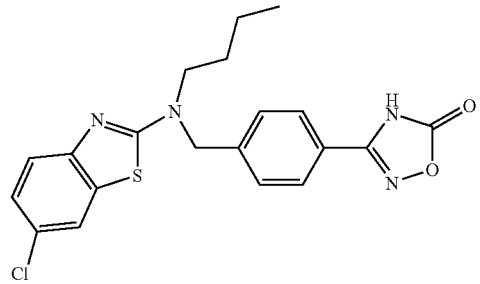

According to the method described in Example 1 3-(4-{[Butyl-(6-chloro-benzothiazol-2-yl)-amino]-methyl}-phenyl)-4H-[1,2,4]oxadiazol-5-one was obtained from 4-butylaminomethyl-benzonitrile and 2,6-dichlorobenzothiazole.

C20H19ClN4O2S (414.92), MS (ESI): 415.1 (M+H⁺).

EXAMPLE 14

3-(4-{2-[(3-Methoxy-propyl)-(6-trifluoromethyl-benzothiazol-2-yl)-amino]-ethyl}-2-methyl-phenyl)-4H-[1,2,4]oxadiazol-5-one

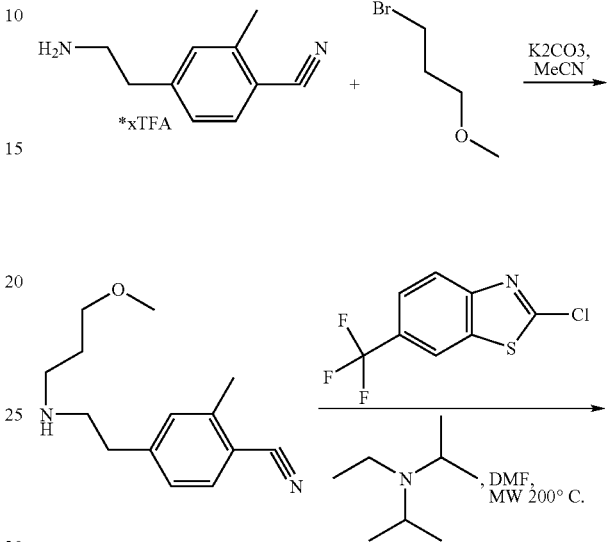

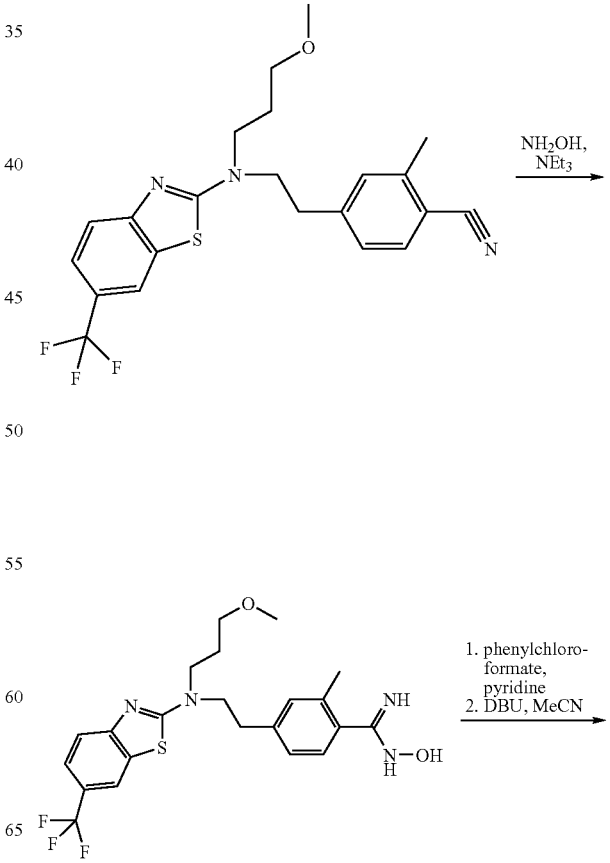

79

-continued

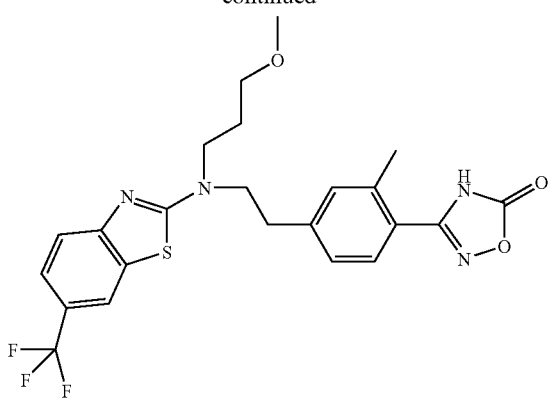

4-[2-(3-Methoxy-propylamino)-ethyl]-2-methyl-benzonitrile

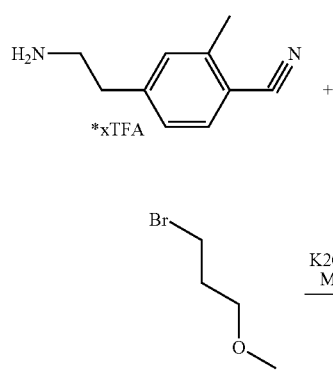

A mixture of 500 mg 4-(2-Amino-ethyl)-2-methyl-benzonitrile trifluoro acetate and 756 mg potassium carbonate were stirred in 10 ml acetonitrile at 80° C. for fifteen minutes. Then 279 mg 1-bromo-3-methoxypropane, dissolved in 5 ml acetonitrile, were added dropwise at 80° C. The reaction mixture was stirred under micro wave irradiation at 120° C. for one hour. The cooled reaction mixture was filtered through a pad of celite to remove the salt. Then the solvent was removed in vacuo. The residue was purified by RP-HPLC to obtain 268 mg 4-[2-(3-Methoxy-propylamino)-ethyl]-2-methyl-benzonitrile as its trifluoroacetate salt.

C14H20N2O .xTFA (232.16+xTFA), MS (ESI): 233.2 (M+H+).

80

3-(4-{2-[(3-Methoxy-propyl)-(6-trifluoromethyl-benzothiazol-2-yl)-amino]-ethyl}-2-methyl-phenyl)-4H-[1,2,4]oxadiazol-5-one

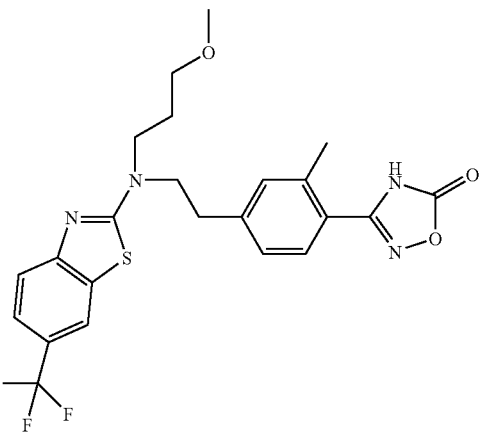

According to the method described in Example 1 3-(4-{2-[(3-Methoxy-propyl)-(6-trifluoromethyl-benzothiazol-2-yl)-amino]-ethyl}-2-methyl-phenyl)-4H-[1,2,4]oxadiazol-5-one was obtained from 4-[2-(3-Methoxy-propylamino)-ethyl]-2-methyl-benzonitrile trifluoroacetate and 2-Chloro-6-trifluoromethyl-benzothiazole.

C23H23F3N4O3S (492.52), MS (ESI): 493.0 (M+H+).

EXAMPLE 15

3-(4-{2-[[2-(2-Methoxy-ethoxy)-ethyl]-(6-trifluoromethyl-benzothiazol-2-yl)-amino]-ethyl}-2-methyl-phenyl)-4H-[1,2,4]oxadiazol-5-one

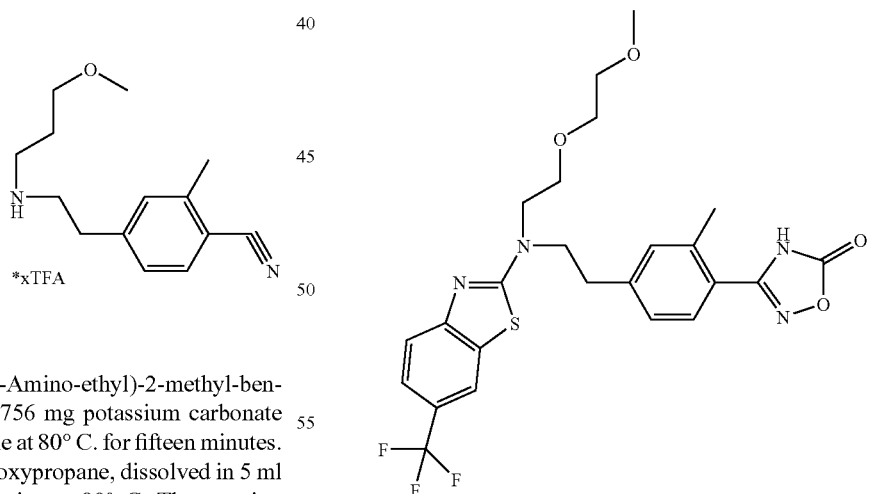

According to the method described in Example 1 and 14 3-(4-{2-[[2-(2-Methoxy-ethoxy)-ethyl]-(6-trifluoromethyl-benzothiazol-2-yl)-amino]-ethyl}-2-methyl-phenyl)-4H-[1,2,4]oxadiazol-5-one was obtained from 4-(2-Amino-ethyl)-2-methyl-benzonitrile trifluoro acetate, 1-bromo-2-(2-methoxyethoxy)ethane and 2-Chloro-6-trifluoromethyl-benzothiazole.

C24H25F3N4O4S (522.55), MS (ESI): 523.0 (M+H+).

EXAMPLE 16

3-(4-{2-[(2-Benzyloxy-ethyl)-(6-trifluoromethyl-benzothiazol-2-yl)-amino]-ethyl}-2-methyl-phenyl)-4H-[1,2,4]oxadiazol-5-one

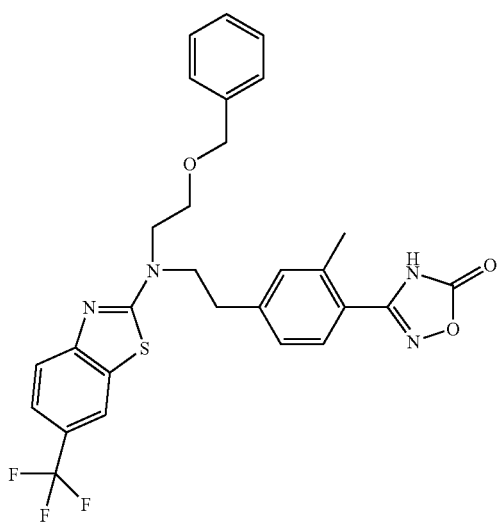

According to the method described in Example 1 and 14 3-(4-{2-[(2-Benzyloxy-ethyl)-(6-trifluoromethyl-benzothiazol-2-yl)-amino]-ethyl}-2-methyl-phenyl)-4H-[1,2,4]oxadiazol-5-one was obtained from 4-(2-Amino-ethyl)-2-methyl-benzonitrile trifluoro acetate, benzyl 2-bromoethylether and 2-Chloro-6-trifluoromethyl-benzothiazole.

$C_{28}H_{25}F_3N_4O_3S$ (554.60), MS (ESI): 555.0 (M+H$^+$).

EXAMPLE 17

3-(4-{2-[(2-Methoxy-ethyl)-(6-trifluoromethyl-benzothiazol-2-yl)-amino]-ethyl}-2-methyl-phenyl)-4H-[1,2,4]oxadiazol-5-one

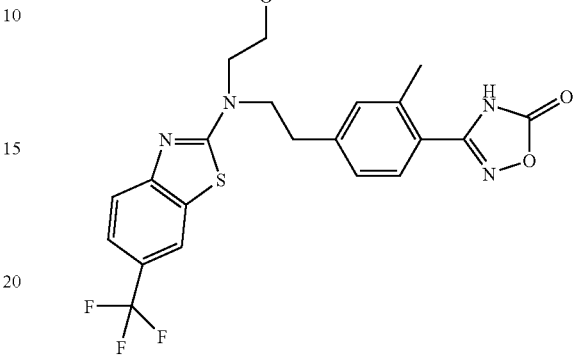

According to the method described in Example 1 and 14 3-(4-{2-[(2-Methoxy-ethyl)-(6-trifluoromethyl-benzothiazol-2-yl)-amino]-ethyl}-2-methyl-phenyl)-4H-[1,2,4]oxadiazol-5-one was obtained from 4-(2-Amino-ethyl)-2-methyl-benzonitrile trifluoro acetate, 2-bromoethyl methylether and 2-Chloro-6-trifluoromethyl-benzothiazole.

$C_{22}H_{21}F_3N_4O_3S$ (478.50), MS (ESI): 479.0 (M+H$^+$).

The following examples were prepared according to process B:

EXAMPLE 18

3-[4-(2-{Butyl-[4-(4-methoxy-phenyl)-thiazol-2-yl]-amino}-ethyl)-phenyl]-4H-[1,2,4]oxadiazol-5-one

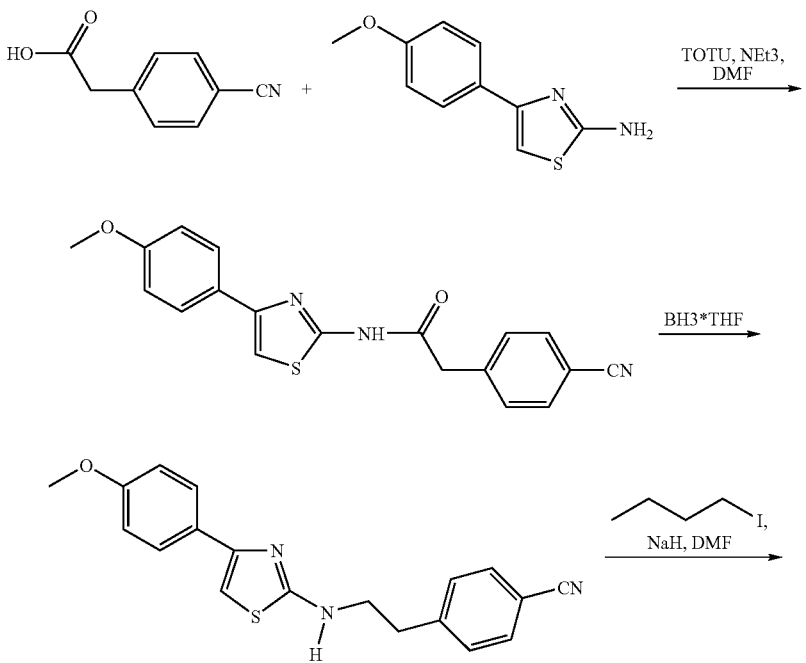

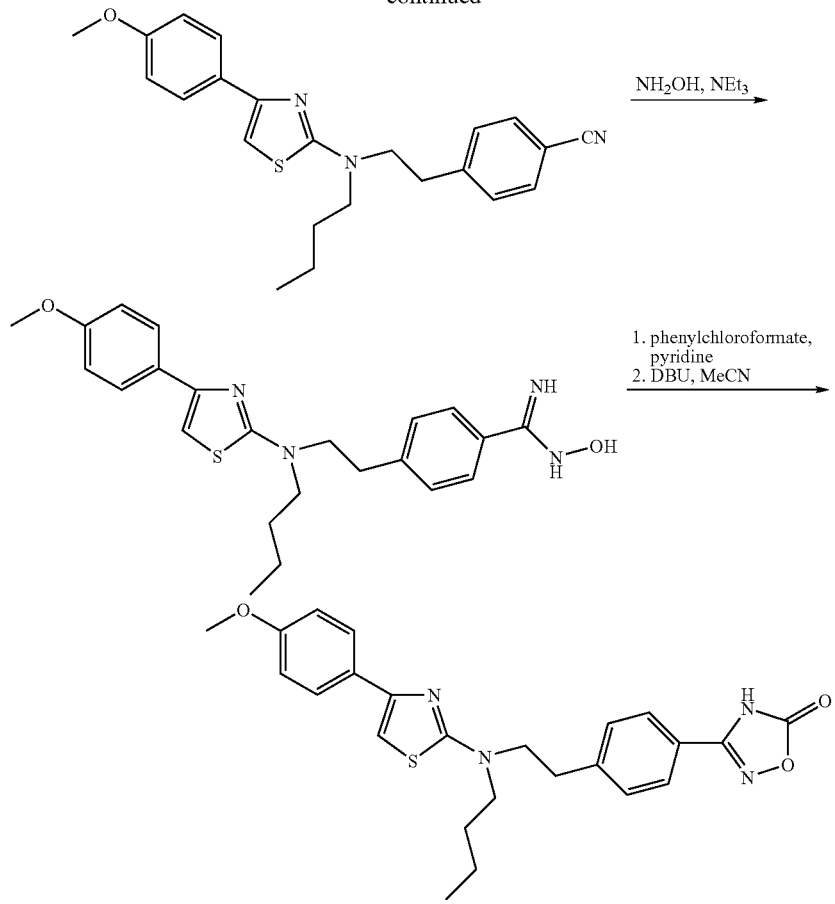

2-(4-Cyano-phenyl)-N-[4-(4-methoxy-phenyl)-thiazol-2-yl]-acetamide

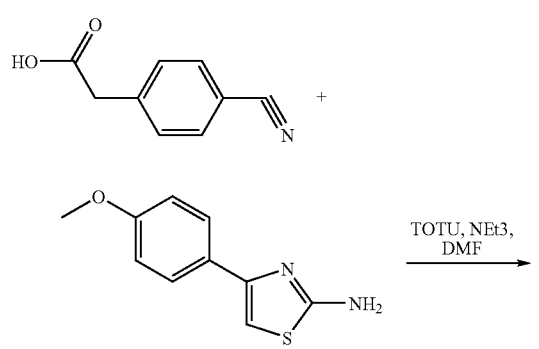

1.41 g 4-(4-Methoxyphenyl)-1,3-thiazol-2-amine was dissolved in 2 ml dimethylformamide. 3.0 ml N,N-Diisopropylethylamine, 1.0 g commercially available (4-Cyano-phenyl)-acetic acid and 2.25 g O-((Ethoxycarbonyl)cyanomethyleneamino)-N,N,N',N'-tetramethyluronium tetrafluoroborate were added. The reaction mixture was stirred at room temperature overnight. Then 200 ml ethyl acetate were added and the mixture was washed three times with portions of 50 ml saturated NaHCO3 solution and then dried over MgSO4. The solvents were removed in vacuo and the residue purified by RP-HPLC to obtain 610 mg 2-(4-Cyano-phenyl)-N-[4-(4-methoxy-phenyl)-thiazol-2-yl]-acetamide as yellow solid.

C19H15N3O2S (349.41), MS (ESI): 350.1 (M+H$^+$).

4-{2-[4-(4-Methoxy-phenyl)-thiazol-2-ylamino]-ethyl}-benzonitrile

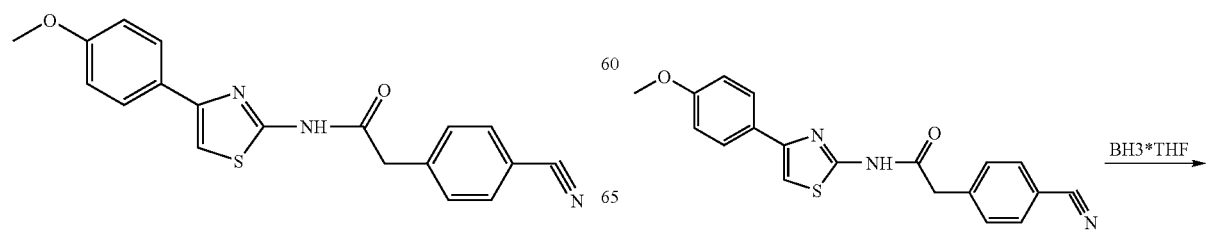

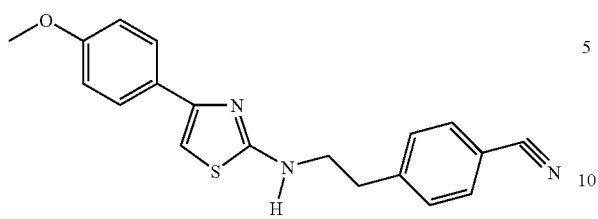

610 mg 2-(4-Cyano-phenyl)-N-[4-(4-methoxy-phenyl)-thiazol-2-yl]-acetamide were suspended in 20 ml tetrahydrofuran. 2.1 ml of a one molar solution of borane tetrahydrofuran complex were added at room temperature. The reaction mixture was stirred at room temperature for two hours and then at 50° C. for two hours. The cooled reaction mixture was poured on 50 ml water and extracted five times with portions of 50 ml ethyl acetate. The combined organic layers were dried over MgSO4. Then the solvents were removed in vacuo to obtain 600 mg 4-{2-[4-(4-Methoxy-phenyl)-thiazol-2-ylamino]-ethyl}-benzonitrile.

C19H17N3OS (335.43), MS (ESI): 336.2 (M+H$^+$).

4-(2-{Butyl-[4-(4-methoxy-phenyl)-thiazol-2-yl]-amino}-ethyl)-benzonitrile

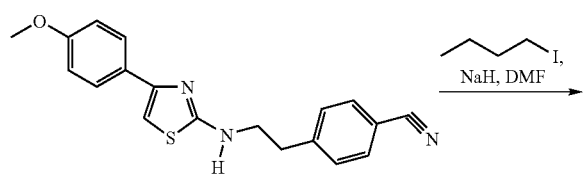

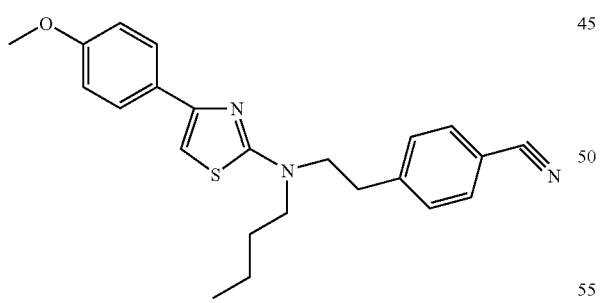

600 mg 4-{2-[4-(4-Methoxy-phenyl)-thiazol-2-ylamino]-ethyl}-benzonitrile were dissolved in 30 ml dimethylformamide. 85.9 mg sodium hydride (24% in mineral oil) were added and the reaction mixture stirred at room temperature for thirty minutes. Then 245 µl 1-Iodobutane were added and the reaction mixture stirred at room temperature for two hours. Then 100 ml ethyl acetate were added and the mixture was washed three times with portions of 50 ml water and then dried over MgSO4. The solvents were removed in vacuo and the residue purified by RP-HPLC to obtain 279 mg 4-(2-{Butyl-[4-(4-methoxy-phenyl)-thiazol-2-yl]-amino}-ethyl)-benzonitrile.

C23H25N3OS (391.54), MS (ESI): 392.2 (M+H$^+$).

3-[4-(2-{Butyl-[4-(4-methoxy-phenyl)-thiazol-2-yl]-amino}-ethyl)-phenyl]-4H-[1,2,4]oxadiazol-5-one

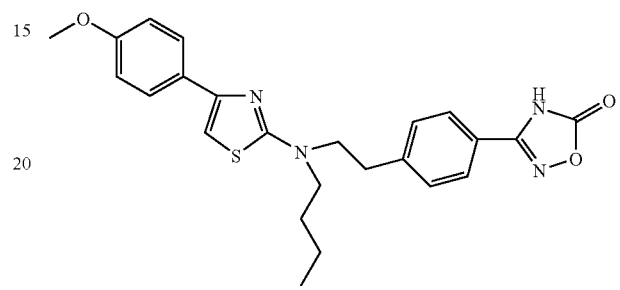

According to the method described in Example 1 3-[4-(2-{Butyl-[4-(4-methoxy-phenyl)-thiazol-2-yl]-amino}-ethyl)-phenyl]-4H-[1,2,4]oxadiazol-5-one was obtained from 4-(2-{Butyl-[4-(4-methoxy-phenyl)-thiazol-2-yl]-amino}-ethyl)-benzonitrile.

C24H26N4O3S (450.56), MS (ESI): 451.2 (M+H$^+$).

EXAMPLE 19

3-[4-(2-{Butyl-[4-(4-chloro-phenyl)-thiazol-2-yl]-amino}-ethyl)-phenyl]-4H-[1,2,4]oxadiazol-5-one

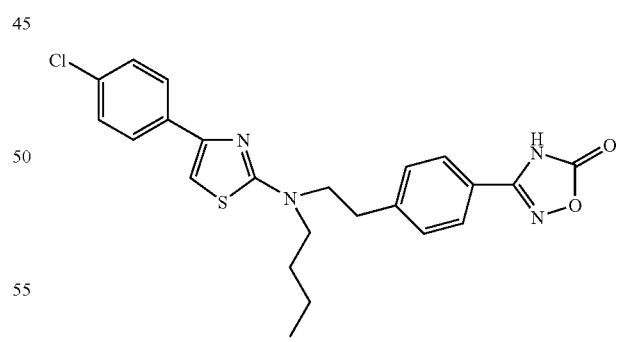

According to the method described in Example 1 and 18 3-[4-(2-{Butyl-[4-(4-chloro-phenyl)-thiazol-2-yl]-amino}-ethyl)-phenyl]-4H-[1,2,4]oxadiazol-5-one was obtained from (4-Cyano-phenyl)-acetic acid, 4-(4-Chloro-phenyl)-thiazol-2-ylamine and 1-Iodobutane.

C23H23ClN4O2S (454.98), MS (ESI): 455.0 (M+H$^+$).

EXAMPLE 20

3-(4-{2-[[4-(4-Chloro-phenyl)-thiazol-2-yl]-(3-methoxy-propyl)-amino]-ethyl}-phenyl)-4H-[1,2,4]oxadiazol-5-one

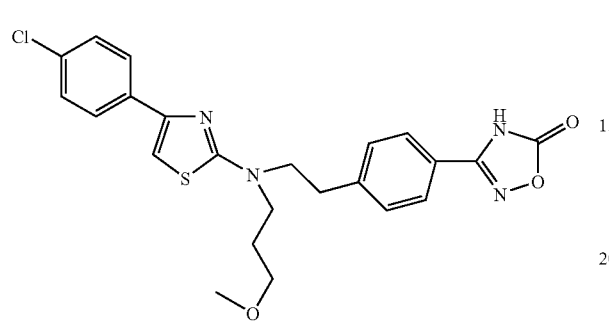

According to the method described in Example 1 and 18 3-(4-{2-[[4-(4-Chloro-phenyl)-thiazol-2-yl]-(3-methoxy-propyl)-amino]-ethyl}-phenyl)-4H-[1,2,4]oxadiazol-5-one was obtained from (4-Cyano-phenyl)-acetic acid, 4-(4-Chloro-phenyl)-thiazol-2-ylamine and 1-bromo-3-methoxypropane.

C23H23ClN4O3S (470.98), MS (ESI): 471.0 (M+H$^+$).

EXAMPLE 21

3-[4-(2-{[4-(4-Chloro-phenyl)-thiazol-2-yl]-[2-(2-methoxy-ethoxy)-ethyl]-amino}-ethyl)-phenyl]-4H-[1,2,4]oxadiazol-5-one

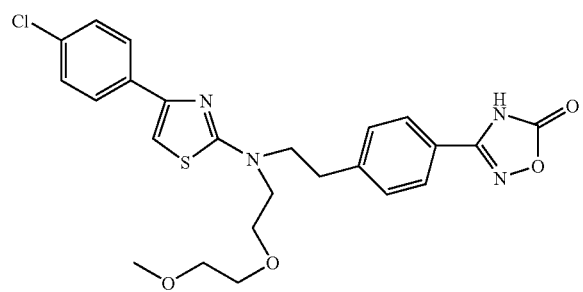

According to the method described in Example 1 and 18 3-[4-(2-{[4-(4-Chloro-phenyl)-thiazol-2-yl]-[2-(2-methoxy-ethoxy)-ethyl]-amino}-ethyl)-phenyl]-4H-[1,2,4]oxadiazol-5-one was obtained from (4-Cyano-phenyl)-acetic acid, 4-(4-Chloro-phenyl)-thiazol-2-ylamine and 1-bromo-2-(methoxyethoxy)ethane.

C24H25ClN4O4S (501.01), MS (ESI): 501.0 (M+H$^+$).

EXAMPLE 22

3-[4-(2-{(2-Benzyloxy-ethyl)-[4-(4-chloro-phenyl)-thiazol-2-yl]-amino}-ethyl)-phenyl]-4H-[1,2,4]oxadiazol-5-one

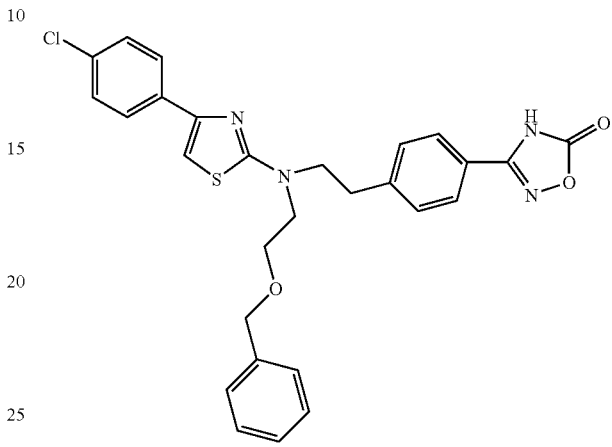

According to the method described in Example 1 and 18 3-[4-(2-{(2-Benzyloxy-ethyl)-[4-(4-chloro-phenyl)-thiazol-2-yl]-amino}-ethyl)-phenyl]-4H-[1,2,4]oxadiazol-5-one was obtained from (4-Cyano-phenyl)-acetic acid, 4-(4-Chloro-phenyl)-thiazol-2-ylamine and benzyl 2-bromoethyl-ether.

C28H25ClN4O3S (533.05), MS (ESI): 533.1 (M+H$^+$).

EXAMPLE 23

3-(4-{2-[[4-(4-Chloro-phenyl)-thiazol-2-yl]-(2-methoxy-ethyl)-amino]-ethyl}-phenyl)-4H-[1,2,4]oxadiazol-5-one

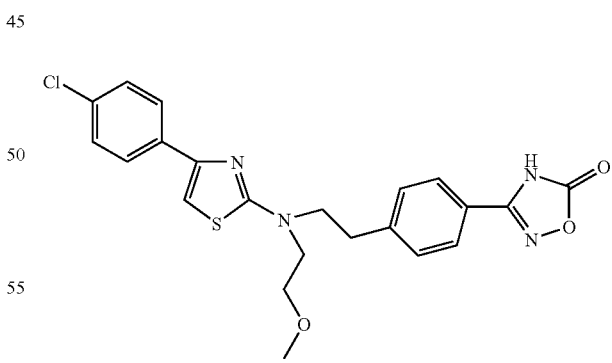

According to the method described in Example 1 and 18 3-(4-{2-[[4-(4-Chloro-phenyl)-thiazol-2-yl]-(2-methoxy-ethyl)-amino]-ethyl}-phenyl)-4H-[1,2,4]oxadiazol-5-one was obtained from (4-Cyano-phenyl)-acetic acid, 4-(4-Chloro-phenyl)-thiazol-2-ylamine and 2-bromoethylmethyl-ether.

C22H21ClN4O3S (456.95), MS (ESI): 457.0 (M+H$^+$).

The following examples were prepared according to process C:
EXAMPLE 24
3-(4-{[Butyl-(6-trifluoromethyl-benzothiazol-2-yl)-amino]-methyl}-2-fluoro-phenyl)-4H-[1,2,4]oxadiazol-5-one
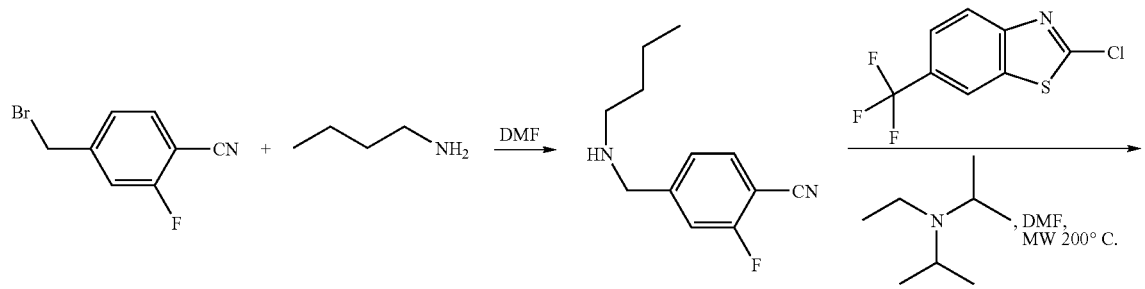
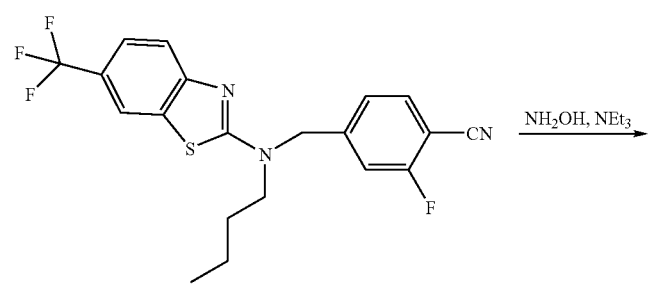
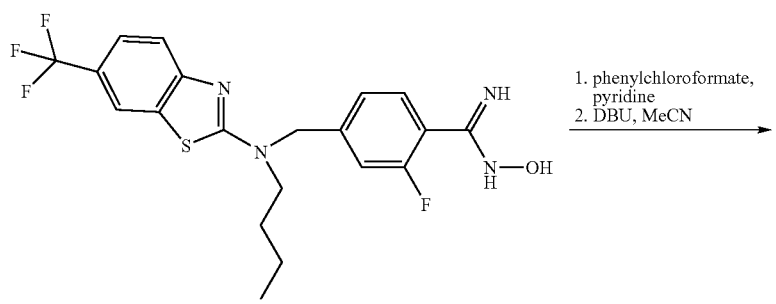
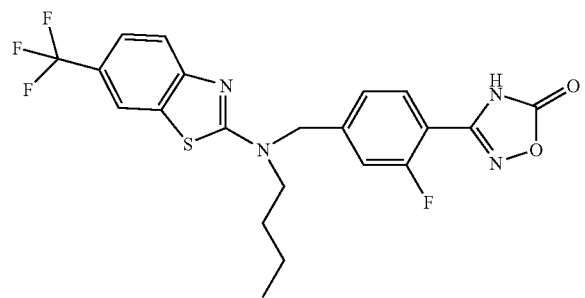

4-Butylaminomethyl-2-fluoro-benzonitrile

EXAMPLE 25

3-(4-{[Butyl-(6-chloro-benzothiazol-2-yl)-amino]-methyl}-2-fluoro-phenyl)-4H-[1,2,4]oxadiazol-5-one

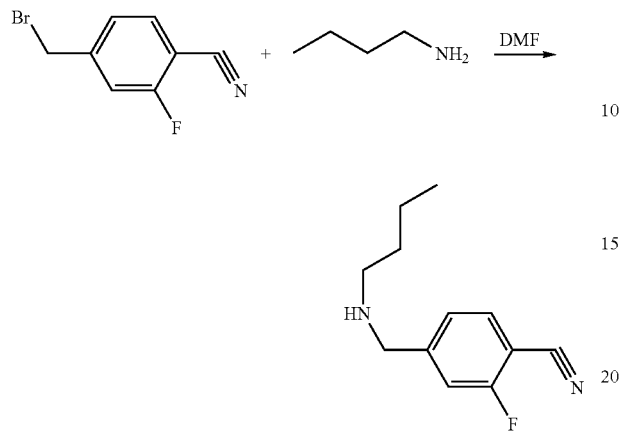

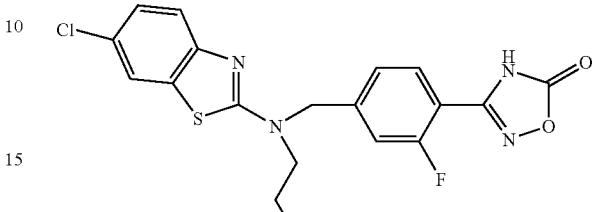

4.64 ml n-butylamine was dissolved in 30 ml dimethylformamide. 667 mg commercially available 4-cyano-3-fluorobenzylbromide, dissolved in 10 ml dimethylformamide was added dropwise. The reaction mixture was stirred at room temperature for thirty minutes. The solvent was removed in vacuo and the residue purified by chromatography on silica gel with the eluent n-heptane:ethyl acetate=1:4=>ethyl acetate:methanol=4:1 to obtain 360 mg 4-Butylaminomethyl-2-fluoro-benzonitrile.

C12H15FN2 (206.27), MS (ESI): 207.2 (M+H$^+$), Rf(ethyl acetate:methanol=9:1)=0.29.

3-(4-{[Butyl-(6-trifluoromethyl-benzothiazol-2-yl)-amino]-methyl}-2-fluoro-phenyl)-4H-[1,2,4]oxadiazol-5-one According to the method described in Example 1 3-(4-{[Butyl-(6-chloro-benzothiazol-2-yl)-amino]-methyl}-2-fluoro-phenyl)-4H-[1,2,4]oxadiazol-5-one was obtained from 4-Butylaminomethyl-2-fluoro-benzonitrile and 2,6-dichloro-benzothiazole.

C20H18ClFN4O2S (432.91), MS (ESI): 433.0 (M+H$^+$).

EXAMPLE 26

3-(2-Fluoro-4-{[(2-pyrrolidin-1-yl-ethyl)-(6-trifluoromethyl-benzothiazol-2-yl)-amino]-methyl}-phenyl)-4H-[1,2,4]oxadiazol-5-one trifluoroacetate

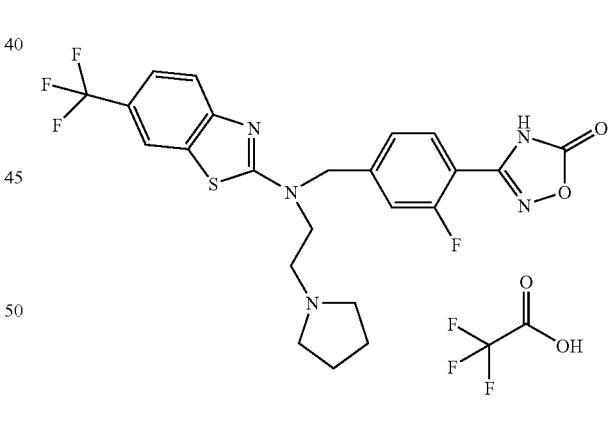

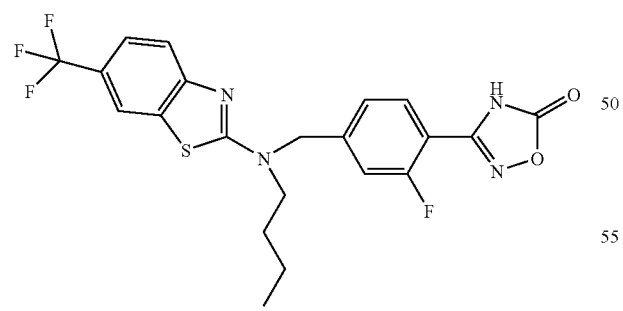

According to the method described in Example 1 3-(4-{[Butyl-(6-trifluoromethyl-benzothiazol-2-yl)-amino]-methyl}-2-fluoro-phenyl)-4H-[1,2,4]oxadiazol-5-one was obtained from 4-Butylaminomethyl-2-fluoro-benzonitrile and 2-Chloro-6-trifluoromethyl-benzothiazole.

C21H18F4N4O2S (466.46), MS (ESI): 467.0 (M+H$^+$).

According to the method described in Example 1 3-(2-Fluoro-4-{[(2-pyrrolidin-1-yl-ethyl)-(6-trifluoromethyl-benzothiazol-2-yl)-amino]-methyl}-phenyl)-4H-[1,2,4]oxadiazol-5-one was obtained from commercially available 4-cyano-3-fluorobenzylbromide, N-(2-5 aminoethyl)pyrrolidine and 2-Chloro-6-trifluoromethyl-benzothiazole. After RP-HPLC the compound was obtained as its trifluoroacetate salt.

C23H21F4N5O2S*C2HF3O2 (507.51+114.02), MS (ESI): 508.2 (M+H$^+$).

EXAMPLE 27

3-(4-{[(2-Dimethylamino-ethyl)-(6-trifluoromethyl-benzothiazol-2-yl)-amino]-methyl}-2-fluoro-phenyl)-4H-[1,2,4]oxadiazol-5-one trifluoroacetate

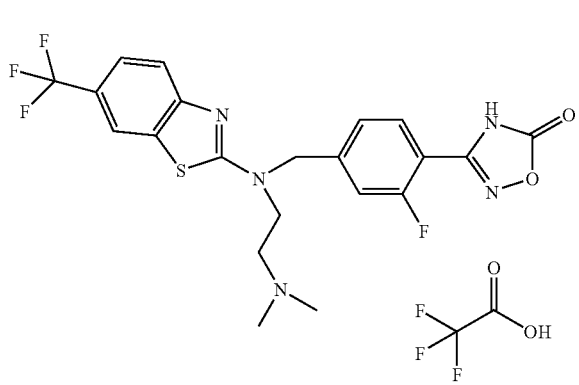

According to the method described in Example 1 3-(4-{[(2-Dimethylamino-ethyl)-(6-trifluoromethyl-benzothiazol-2-yl)-amino]-methyl}-2-fluoro-phenyl)-4H-[1,2,4]oxadiazol-5-one was obtained from commercially available 4-cyano-3-fluorobenzylbromide, N,N-dimethylethylenediamine and 2-Chloro-6-trifluoromethyl-benzothiazole. After RP-HPLC the compound was obtained as its trifluoroacetate salt.

C21H19F4N5O2S*C2HF3O2 (481.48+114.02), MS (ESI): 482.2 (M+H+).

EXAMPLE 28

3-(2-Fluoro-4-{[(2-methoxy-ethyl)-(6-trifluoromethyl-benzothiazol-2-yl)-amino]-methyl}-phenyl)-4H-[1,2,4]oxadiazol-5-one

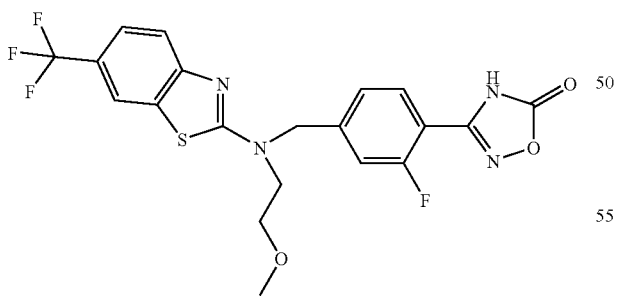

According to the method described in Example 1 3-(2-Fluoro-4-{[(2-methoxy-ethyl)-(6-trifluoromethyl-benzothiazol-2-yl)-amino]-methyl}-phenyl)-4H-[1,2,4]oxadiazol-5-one was obtained from commercially available 4-cyano-3-fluorobenzylbromide, 2-methoxyethylamine and 2-Chloro-6-trifluoromethyl-benzothiazole.

C20H16F4N4O3S (468.43), MS (ESI): 469.1 (M+H+).

EXAMPLE 29

3-(2-Fluoro-4-{[(2-piperidin-1-yl-ethyl)-(6-trifluoromethyl-benzothiazol-2-yl)-amino]-methyl}-phenyl)-4H-[1,2,4]oxadiazol-5-one trifluoroacetate

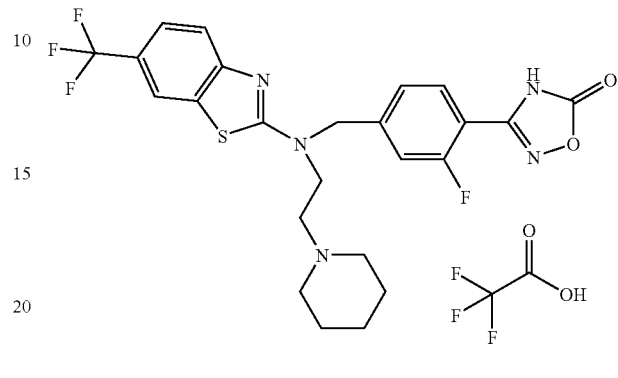

According to the method described in Example 1 3-(2-Fluoro-4-{[(2-piperidin-1-yl-ethyl)-(6-trifluoromethyl-benzothiazol-2-yl)-amino]-methyl}-phenyl)-4H-[1,2,4]oxadiazol-5-one was obtained from commercially available 4-cyano-3-fluorobenzylbromide, 1-(2-aminoethyl)piperidine and 2-Chloro-6-trifluoromethyl-benzothiazole. After RP-HPLC the compound was obtained as its trifluoroacetate salt.

C24H23F4N5O2S*C2HF3O2 (521.54+114.02), MS (ESI): 522.2 (M+H+).

EXAMPLE 30

3-(2-Fluoro-4-{[(2-morpholin-4-yl-ethyl)-(6-trifluoromethyl-benzothiazol-2-yl)-amino]-methyl}-phenyl)-4H-[1,2,4]oxadiazol-5-one trifluoroacetate

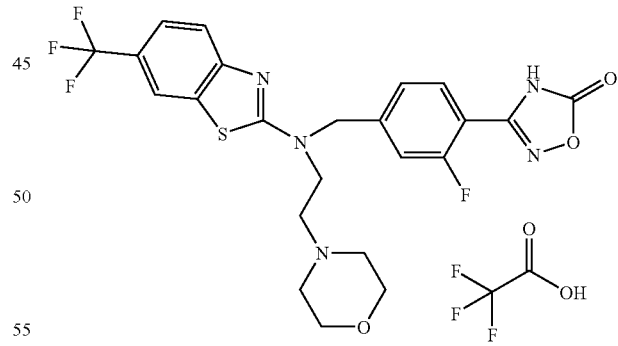

According to the method described in Example 1 3-(2-Fluoro-4-{[(2-morpholin-4-yl-ethyl)-(6-trifluoromethyl-benzothiazol-2-yl)-amino]-methyl}-phenyl)-4H-[1,2,4]oxadiazol-5-one was obtained from commercially available 4-cyano-3-fluorobenzylbromide, N-(2-aminoethyl)morpholine and 2-Chloro-6-trifluoromethyl-benzothiazole. After RP-HPLC the compound was obtained as its trifluoroacetate salt.

C23H21F4N5O3S*C2HF3O2 (523.51+114.02), MS (ESI): 524.2 (M+H+).

EXAMPLE 31

3-(2-Fluoro-4-{[[2-(1-methyl-pyrrolidin-2-yl)-ethyl]-(6-trifluoromethyl-benzothiazol-2-yl)-amino]-methyl}-phenyl)-4H-[1,2,4]oxadiazol-5-one trifluoroacetate

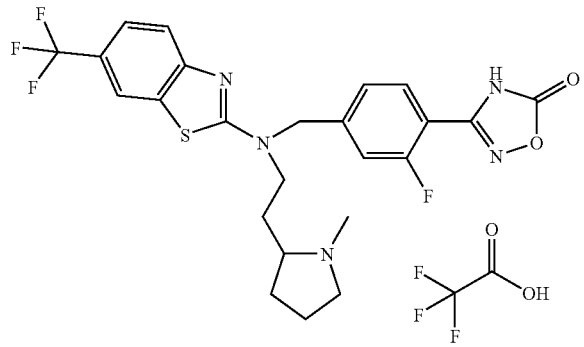

According to the method described in Example 1 3-(2-Fluoro-4-{[[2-(1-methyl-pyrrolidin-2-yl)-ethyl]-(6-trifluoromethyl-benzothiazol-2-yl)-amino]-methyl}-phenyl)-4H-[1,2,4]oxadiazol-5-one was obtained from commercially available 4-cyano-3-fluorobenzylbromide, 2-(2-aminoethyl)-1-methylpyrrolidine and 2-Chloro-6-trifluoromethyl-benzothiazole. After RP-HPLC the compound was obtained as its trifluoroacetate salt.

C24H23F4N5O2S*C2HF3O2 (521.54+114.02), MS (ESI): 522.2 (M+H$^+$).

EXAMPLE 32

3-(4-{[(2-Pyrrolidin-1-yl-ethyl)-(6-trifluoromethyl-benzothiazol-2-yl)-amino]-methyl}-2-trifluoromethyl-phenyl)-4H-[1,2,4]oxadiazol-5-one

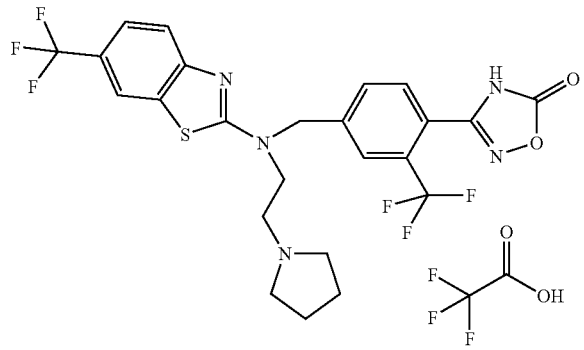

According to the method described in Example 1 3-(4-{[(2-Pyrrolidin-1-yl-ethyl)-(6-trifluoromethyl-benzothiazol-2-yl)-amino]-methyl}-2-trifluoromethyl-phenyl)-4H-[1,2,4]oxadiazol-5-one was obtained from 4-Bromomethyl-2-trifluoromethyl-benzonitrile, N-(2-aminoethyl)pyrrolidine and 2-Chloro-6-trifluoromethyl-benzothiazole. After RP-HPLC the compound was obtained as its trifluoroacetate salt.

C24H21F6N5O2S*C2HF3O2 (557.52+114.02), MS (ESI): 558.0 (M+H$^+$).

EXAMPLE 33

3-(4-{[(2-Dimethylamino-ethyl)-(6-trifluoromethyl-benzothiazol-2-yl)-amino]-methyl}-2-trifluoromethyl-phenyl)-4H-[1,2,4]oxadiazol-5-one trifluoroacetate

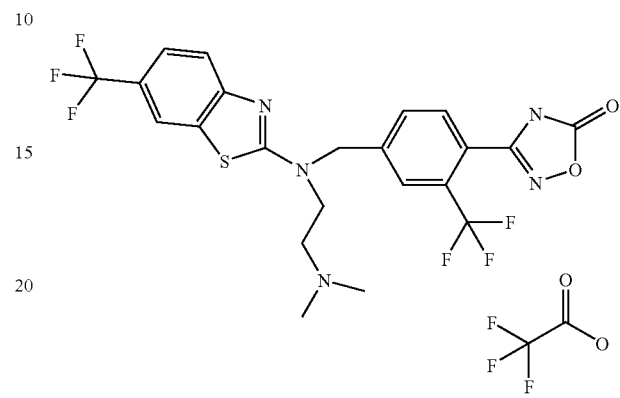

According to the method described in Example 1 3-(4-{[(2-Dimethylamino-ethyl)-(6-trifluoromethyl-benzothiazol-2-yl)-amino]-methyl}-2-trifluoromethyl-phenyl)-4H-[1,2,4]oxadiazol-5-one was obtained from 4-Bromomethyl-2-trifluoromethyl-benzonitrile, N,N-dimethylethylenediamine and 2-Chloro-6-trifluoromethyl-benzothiazole. After RP-HPLC the compound was obtained as its trifluoroacetate salt.

C22H19F6N5O2S*C2HF3O2 (531.48+114.02), MS (ESI): 532.1 (M+H$^+$).

EXAMPLE 34

3-(4-{[(2-Methoxy-ethyl)-(6-trifluoromethyl-benzothiazol-2-yl)-amino]-methyl}-2-trifluoromethyl-phenyl)-4H-[1,2,4]oxadiazol-5-one

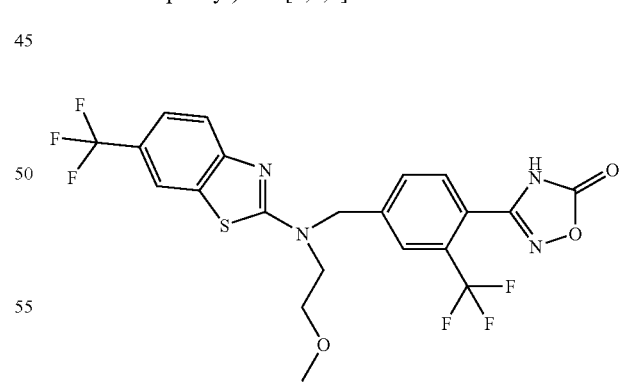

According to the method described in Example 1 3-(4-{[(2-Methoxy-ethyl)-(6-trifluoromethyl-benzothiazol-2-yl)-amino]-methyl}-2-trifluoromethyl-phenyl)-4H-[1,2,4]oxadiazol-5-one was obtained from 4-Bromomethyl-2-trifluoromethyl-benzonitrile, 2-methoxyethylamine and 2-Chloro-6-trifluoromethyl-benzothiazole.

C21H16F6N4O3S (518.44), MS (ESI): 519.2 (M+H$^+$).

EXAMPLE 35

3-(4-{[(2-Piperidin-1-yl-ethyl)-(6-trifluoromethyl-benzothiazol-2-yl)-amino]-methyl}-2-trifluoromethyl-phenyl)-4H-[1,2,4]oxadiazol-5-one trifluoroacetate

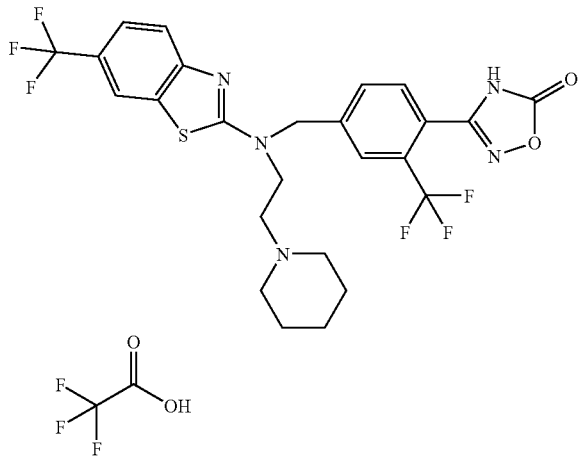

According to the method described in Example 1 3-(4-{[(2-Piperidin-1-yl-ethyl)-(6-trifluoromethyl-benzothiazol-2-yl)-amino]-methyl}-2-trifluoromethyl-phenyl)-4H-[1,2,4]oxadiazol-5-one was obtained from 4-Bromomethyl-2-trifluoromethyl-benzonitrile, 1-(2-aminoethyl)piperidine and 2-Chloro-6-trifluoromethyl-benzothiazole. After RP-HPLC the compound was obtained as its trifluoroacetate salt.

C25H23F6N5O2S*C2HF3O2 (571.55+114.02), MS (ESI): 572.2 (M+H$^+$).

EXAMPLE 36

3-(4-{[(2-Morpholin-4-yl-ethyl)-(6-trifluoromethyl-benzothiazol-2-yl)-amino]-methyl}-2-trifluoromethyl-phenyl)-4H-[1,2,4]oxadiazol-5-one trifluoroacetate

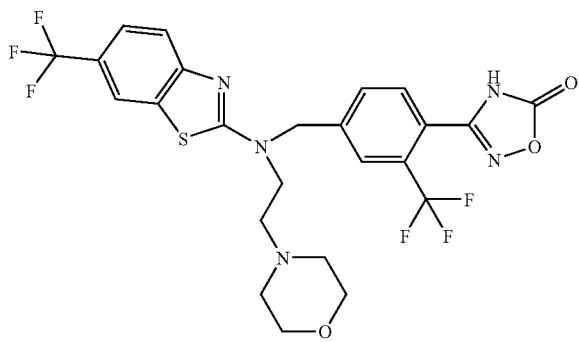

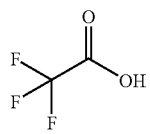

According to the method described in Example 1 3-(4-{[(2-Morpholin-4-yl-ethyl)-(6-trifluoromethyl-benzothiazol-2-yl)-amino]-methyl}-2-trifluoromethyl-phenyl)-4H-[1,2,4]oxadiazol-5-one was obtained from 4-Bromomethyl-2-trifluoromethyl-benzonitrile, N-(2-aminoethyl)morpholine and 2-Chloro-6-trifluoromethyl-benzothiazole. After RP-HPLC the compound was obtained as its trifluoroacetate salt.

C24H21F6N5O3S*C2HF3O2 (573.52+114.02), MS (ESI): 574.2 (M+H$^+$).

EXAMPLE 37

3-(4-{[[2-(1-Methyl-pyrrolidin-2-yl)-ethyl]-(6-trifluoromethyl-benzothiazol-2-yl)-amino]-methyl}-2-trifluoromethyl-phenyl)-4H-[1,2,4]oxadiazol-5-one trifluoroacetate

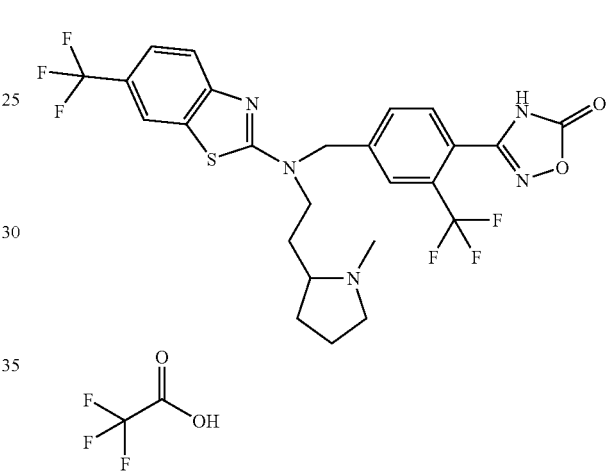

According to the method described in Example 1 3-(4-{[[2-(1-Methyl-pyrrolidin-2-yl)-ethyl]-(6-trifluoromethyl-benzothiazol-2-yl)-amino]-methyl}-2-trifluoromethyl-phenyl)-4H-[1,2,4]oxadiazol-5-one was obtained from 4-Bromomethyl-2-trifluoromethyl-benzonitrile, 2-(2-aminoethyl)-1-methylpyrrolidine and 2-Chloro-6-trifluoromethyl-benzothiazole. After RP-HPLC the compound was obtained as its trifluoroacetate salt.

C25H23F6N5O2S*C2HF3O2 (571.55+114.02), MS (ESI): 572.2 (M+H$^+$).

The following examples were prepared according to process D:

EXAMPLE 38

3-[4-({Butyl-[4-(4-methoxy-phenyl)-thiazol-2-yl]-amino}-methyl)-phenyl]-4H-[1,2,4]oxadiazol-5-one

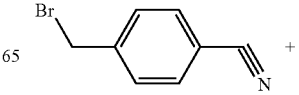

-continued

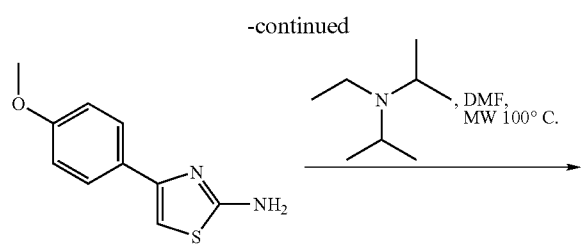

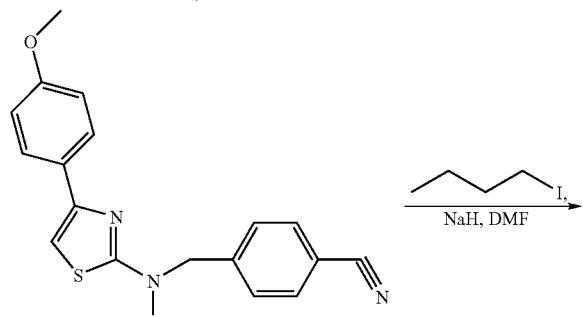

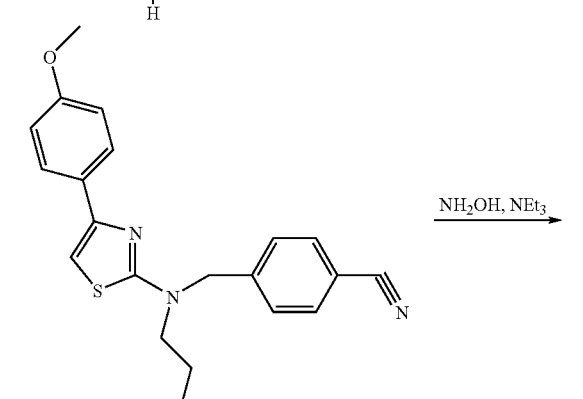

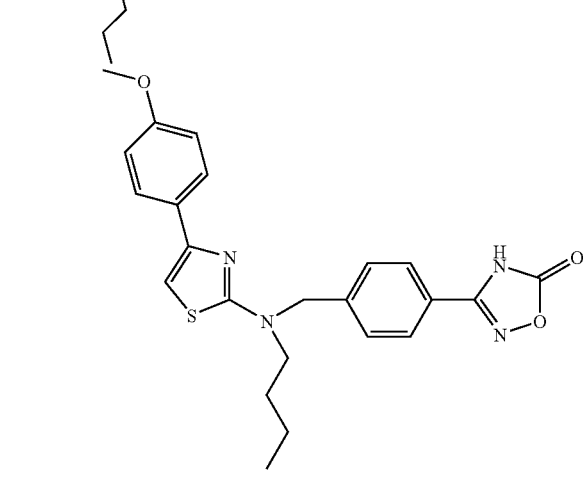

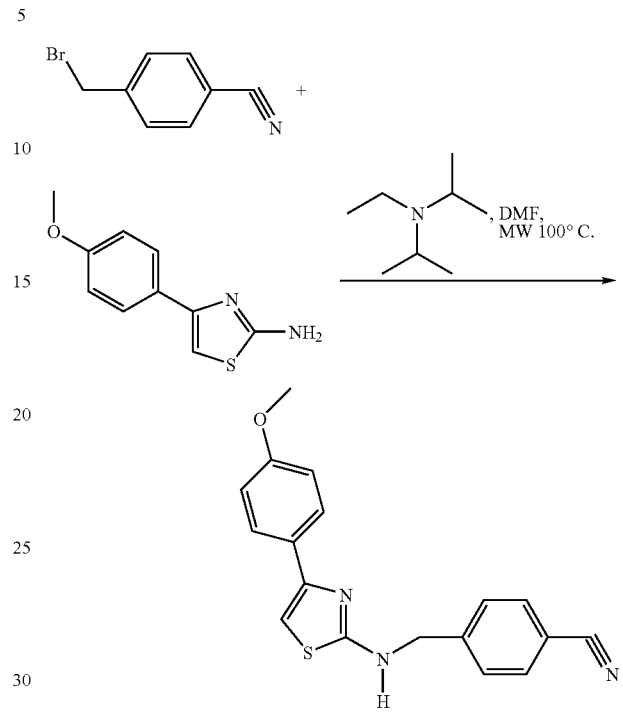

4-{[4-(4-Methoxy-phenyl)-thiazol-2-ylamino]-methyl}-benzonitrile 5.0 g 4-(4-Methoxyphenyl)-1,3-thiazol-2-amine, 4.29 g 4-bromomethyl-benzonitrile and 6.0 ml N,N-Diisopropyl-ethylamine were suspended in 20 ml dimethylformamide. The reaction mixture was stirred under microwave irradiation at 100° C. for thirty minutes. The cooled reaction mixture was diluted by the addition of 100 ml ethyl acetate and washed 50 ml saturated NaHCO3 solution and the dried over MgSO4. The solvent was removed in vacuo and the resulting residue was purified by chromatography on silica gel with the eluent petroleum ether: ethyl acetate=3:2 to obtain 2.41 g 4-{[4-(4-Methoxy-phenyl)-thiazol-2-ylamino]-methyl}-benzonitrile.

C18H15N3OS (321.40), MS (ESI): 322.1 (M+H$^+$), Rf(n-heptane:ethyl acetate=1:1)=0.29.

4-({Butyl-[4-(4-methoxy-phenyl)-thiazol-2-yl]-amino}-methyl)-benzonitrile

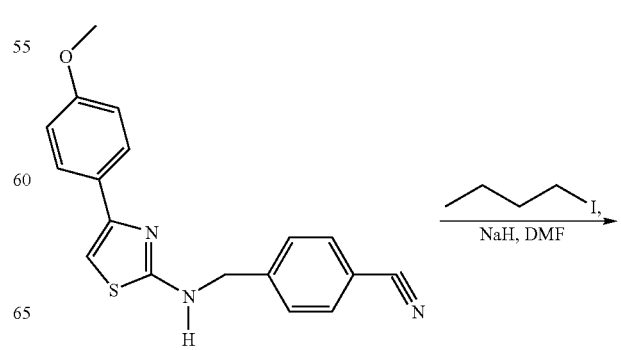

-continued

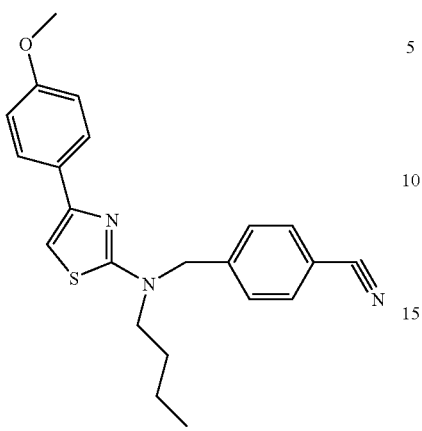

1.0 g 4-{[4-(4-Methoxy-phenyl)-thiazol-2-ylamino]-methyl}-benzonitrile was dissolved in 150 ml dimethylformamide. 150 mg sodium hydride (24% in mineral oil) were added and the reaction mixture stirred at room temperature for thirty minutes. Then 0.43 ml 1-Iodobutane were added and the reaction mixture stirred at room temperature for two hours. Then 100 ml ethyl acetate were added and the mixture was washed three times with portions of 50 ml water and then dried over MgSO4. The solvents were removed in vacuo to obtain 1.2 g 4-({Butyl-[4-(4-methoxy-phenyl)-thiazol-2-yl]-amino}-methyl)-benzonitrile.

C22H23N3OS (377.51), MS (ESI): 378.2 (M+H$^+$).

3-[4-({Butyl-[4-(4-methoxy-phenyl)-thiazol-2-yl]-amino}-methyl)-phenyl]-4H-[1,2,4]oxadiazol-5-one

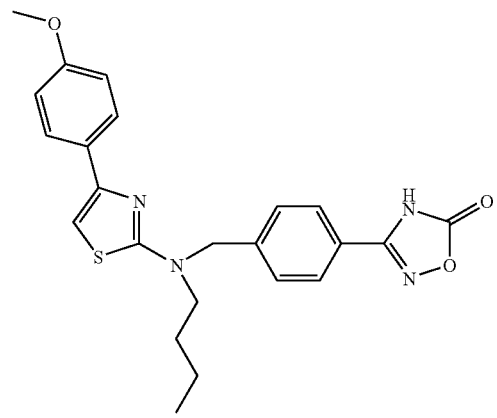

According to the method described in Example 1 3-[4-({Butyl-[4-(4-methoxy-phenyl)-thiazol-2-yl]-amino}-methyl)-phenyl]-4H-[1,2,4]oxadiazol-5-one was obtained from 4-({Butyl-[4-(4-methoxy-phenyl)-thiazol-2-yl]-amino}-methyl)-benzonitrile.

C23H24N4O3S (436.54), MS (ESI): 437.4 (M+H$^+$).

EXAMPLE 39

3-(4-{[[4-(4-Chloro-phenyl)-thiazol-2-yl]-(3-methoxy-propyl)-amino]-methyl}-2-fluoro-phenyl) -4H-[1,2,4]oxadiazol-5-one

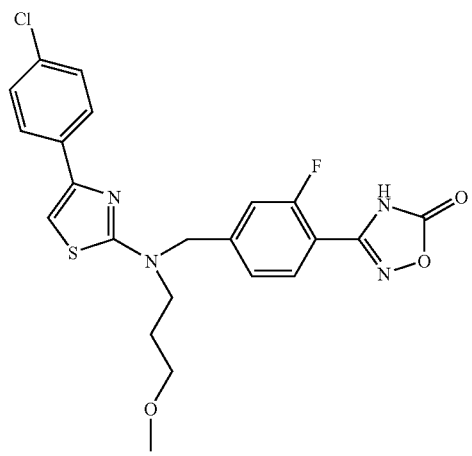

According to the method described in Example 1 and 38 3-(4-{[[4-(4-Chloro-phenyl)-thiazol-2-yl]-(3-methoxy-propyl)-amino]-methyl}-2-fluoro-phenyl)-4H-[1,2,4]oxadiazol-5-one was obtained from 2-amino-4-(4-chlorophenyl) thiazole, 4-cyano-3-fluorobenzylbromide and 1-bromo-3-methoxypropane.

C22H20ClFN4O3S (474.95), MS (ESI): 475.0 (M+H$^+$).

EXAMPLE 40

3-(4-{[[4-(4-Chloro-phenyl)-thiazol-2-yl]-(2-methoxy-ethyl)-amino]-methyl}-2-fluoro-phenyl)-4H-[1,2,4]oxadiazol-5-one

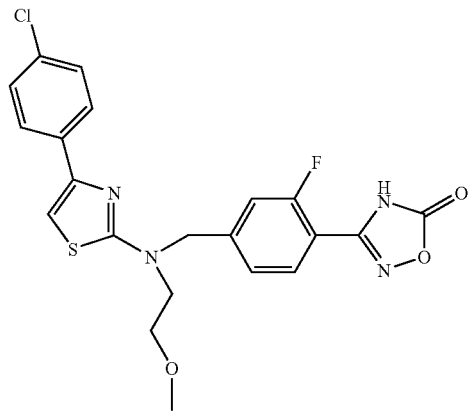

According to the method described in Example 1 and 38 3-(4-{[[4-(4-Chloro-phenyl)-thiazol-2-yl]-(2-methoxy-ethyl)-amino]-methyl}-2-fluoro-phenyl)-4H-[1,2,4]oxadiazol-5-one was obtained from 2-amino-4-(4-chlorophenyl) thiazole, 4-cyano-3-fluorobenzylbromide and 2-bromoethylmethylether.

C21H18ClFN4O3S (460.92), MS (ESI): 461.0 (M+H$^+$).

EXAMPLE 41

3-[4-({[4-(4-Chloro-phenyl)-thiazol-2-yl]-[2-(2-methoxy-ethoxy)-ethyl]-amino}-methyl)-2-fluoro-phenyl]-4H-[1,2,4]oxadiazol-5-one

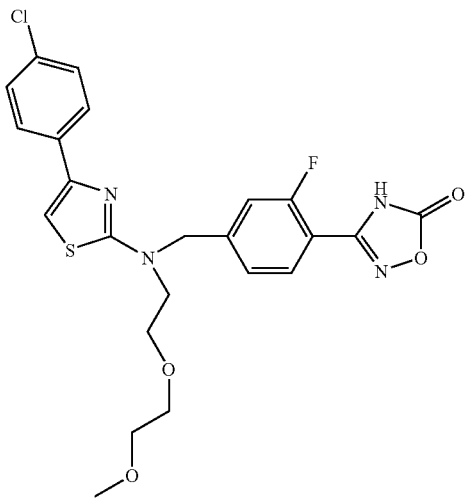

According to the method described in Example 1 and 38 3-[4-({[4-(4-Chloro-phenyl)-thiazol-2-yl]-[2-(2-methoxy-ethoxy)-ethyl]-amino}-methyl)-2-fluoro-phenyl]-4H-[1,2,4]oxadiazol-5-one was obtained from 2-amino-4-(4-chlorophenyl)thiazole, 4-cyano-3-fluorobenzylbromide and 1-bromo-2-(2-methoxyethoxy)ethane. C23H22ClFN4O4S (504.97), MS (ESI): 505.1 (M+H$^+$).

What is claimed is:

1. A compound of formula I

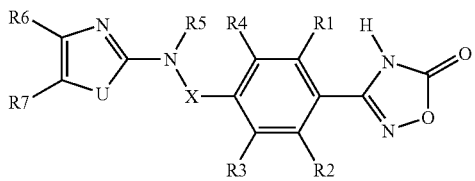

Formula I wherein:
R1 is selected from the group consisting of H, halogen, (C1-C8) alkyl, (C1-C4) alkylene-O—(C1-C4) alkylene-H, SCH$_3$, and CN, wherein the alkyl and alkylene groups are unsubstituted or optionally mono, di- or tri-substituted by F;
R2, R3 and R4 are independently selected from the group consisting of H, halogen, (C1-C8) alkyl, (C1-C4) alkylene-O—(C1-C4) alkylene-H, SCH$_3$, and CN, wherein the alkyl and alkylene are unsubstituted or mono, di- or tri-substituted by F;
X is —CH2— or —CH2—CH2—;
U is S or O;
R5 is selected from the group consisting of H, (C1-C8) alkyl, (C1-C4) alkylene-O—(C1-C4) alkyl, (C1-C4) alkylene-O—(C1-C4) alkylene-(C6-C10) aryl, (C1-C4) alkylene-(C3-C12) cycloalkyl, (C2-C8) alkenyl, (C1-C4) alkylene-(C3-C15) heterocycloalkyl, (C1-C4) alkylene-(C3-C15) heterocycloalkenyl, and (C1-C4) alkylene-(C5-C15) heteroaryl, wherein the alkyl and alkylene are unsubstituted or mono-, di- or tri-substituted by F, N((C1-C4) alkylene-H)—(C1-C4) alkylene-H or O—(C1-C4) alkylene-H, and wherein the cycloalkyl, aryl, heterocycloalkyl, heterocycloalkenyl and heteroaryl are unsubstituted or mono-, di- or tri-substituted by a moiety selected from the group consisting of F, Cl, Br, CF$_3$, (C1-C4) alkyl, CO—(C1-C4) alkyl and (C1-C4)-alkylene-O—(C1-C4) alkylene-H; and
R6 and R7 are is selected from the group consisting of H and (C6-C14) aryl which may be unsubstituted or mono-, di- or tri-substituted by a moiety selected from the group consisting of F, Cl, Br, CF$_3$, (C1-C4) alkyl and (C1-C4)-alkylen-O—(C1-C4) alkylene-H;

or

R6 and R7 together with the oxazole or thiazole ring form a benzothiazole or benzoxazole ring, which is unsubstituted or mono-, di- or tri-substituted by F, Cl, Br, CF$_3$, (C1-C4) alkyl or (C1-C4)-alkylen-O—(C1-C4) alkylene-H;

or a stereoisomeric form thereof, an enantiomeric form thereof or a mixture in any ratio thereof, or a physiologically acceptable salt or a tautomeric form thereof.

2. The compound according to claim 1, wherein
R1 is halogen, (C1-C8) alkyl, (C1-C4) alkylene-O—(C1-C4) alkylene-H, SCH$_3$, or CN, wherein alkyl and alkylene are unsubstituted or mono, bi- or tri-substituted by F;
R2, R3 and R4 are H;
X is —CH2—CH2—;
U is S;
R5 is selected from the group consisting of (C1-C4) alkyl, (C1-C4) alkylene-O—(C1-C4) alkyl, (C1-C4) alkylene-O—CH2-phenyl, and (C1-C4) alkylene-(C5-C6) heterocycloalkyl, wherein the alkyl and alkylene are unsubstituted or mono-, di- or tri- substituted by N((C1-C4) alkyl)-(C1-C4) alkyl, and wherein the heterocycloalkyl is unsubstituted or mono-substituted by (C1-C4) alkyl or CO—(C1-C4) alkyl; and
R6 is phenyl which is optionally mono-substituted by Cl or methoxy;

or

R6 and R7 together with the oxazole or thiazole group to which they are attached form a benzothiazole ring optionally substituted by —CF$_3$;

or a stereoisomeric form thereof, an enantiomeric form thereof or a mixture in any ratio thereof, or a physiologically acceptable salt or a tautomeric form thereof.

3. The compound according to claim 1, wherein
R1 is selected from the group consisting of halogen, (C1-C8) alkyl, (C1-C4) alkylene-O—(C1-C4) alkylene-H, SCH$_3$, and CN, wherein alkyl and alkylene are unsubstituted or optionally mono, di- or tri-substituted by F;
R2, R3 and R4 are H;
X is —CH2—;
U is S;
R5 is selected from the group consisting of (C1-C4) alkyl, (C1-C4) alkylene-O—(C1-C4) alkyl, (C1-C4) alkylene-O—CH2-phenyl and (C1-C4) alkylene-(C5-C6) heterocycloalkyl, wherein the alkyl and alkylene groups are unsubstituted or mono-, di- or tri-substituted by N((C1-C4) alkyl)-(C1-C4) alkyl, and wherein the heterocycloalkyl is unsubstituted or mono-substituted by (C1-C4) alkyl or CO—(C1-C4) alkyl; and R6 is a phenyl group that is mono-substituted by Cl or methoxy;

or

R6 and R7 together with the oxazole or thiazole ring to which they are attached form a benzothiazole ring that is optionally substituted by CF$_3$;

or a stereoisomeric form thereof, an enantiomeric form thereof or a mixture in any ratio thereof, or a physiologically acceptable salt or a tautomeric form thereof.

4. The compound according to claim 1, wherein

R1 is selected from the group consisting of H, F, Cl and (C1-C4) alkyl which is un-substituted or mono-, di- or tri-substituted by F;

or a stereoisomeric form thereof, an enantiomeric form thereof or a mixture in any ratio thereof, or a physiologically acceptable salt or a tautomeric form thereof.

5. The compound according to claim 1, wherein

R1 is selected from the group consisting of H, F and —CH$_3$;

or a stereoisomeric form thereof, an enantiomeric form thereof or a mixture in any ratio thereof, or a physiologically acceptable salt or a tautomeric form thereof.

6. The compound according to claim 1, wherein

R1 is F or CH$_3$;

or a stereoisomeric form thereof, an enantiomeric form thereof or a mixture in any ratio thereof, or a physiologically acceptable salt or a tautomeric form thereof.

7. The compound according to claim 1, wherein

R6 and R7 together with the thiazole ring to which they are attached form 6-trifluoromethyl-benzothiazole;

or a stereoisomeric form thereof, an enantiomeric form thereof or a mixture in any ratio thereof, or a physiologically acceptable salt or a tautomeric form thereof.

8. A pharmaceutical composition comprising at least one compound according to claim 1, or a stereoisomeric form thereof, an enantiomeric form thereof or a mixture in any ratio thereof, or a physiologically acceptable salt or a tautomeric form thereof, in combination with a pharmaceutically acceptable excipient.

9. A pharmaceutical composition according to claim 8 further comprising at least one therapeutically active antidiabetic compound.

10. A pharmaceutical composition according to claim 8 further comprising at least one therapeutically active lipid modulator compound.

* * * * *